Figure 1A:
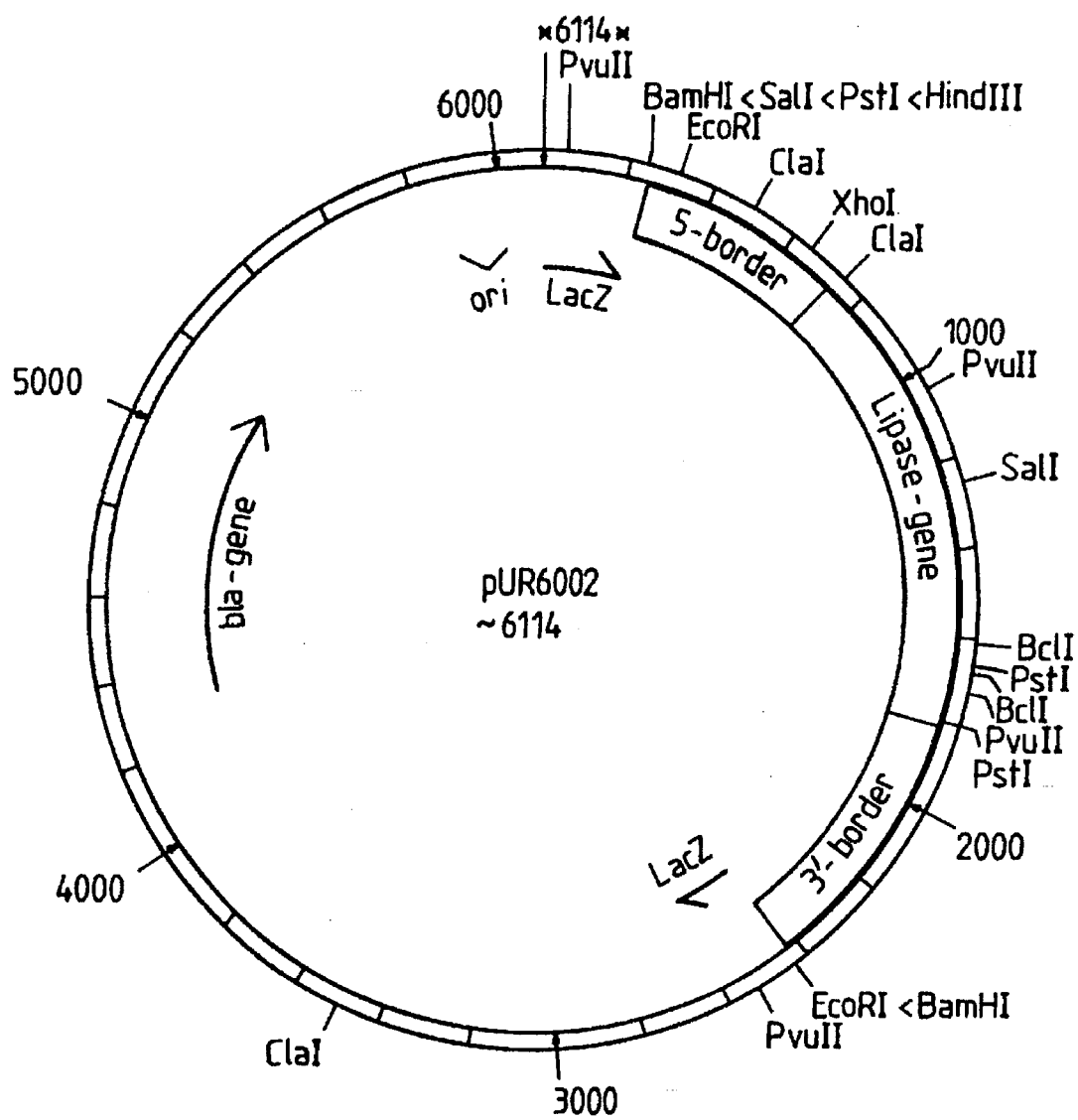
Figure 1B:
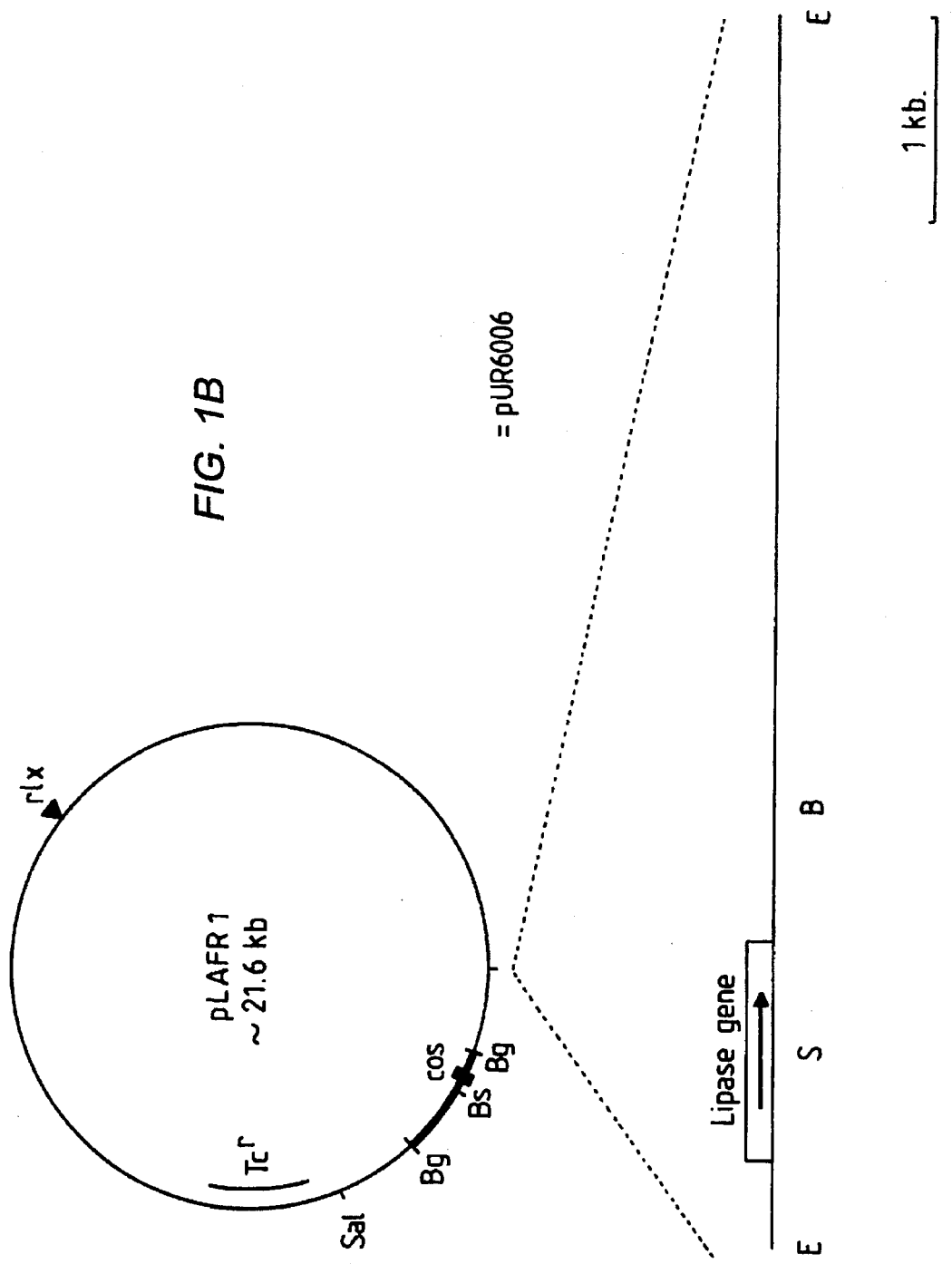

United States Patent [19]

Batenburg et al.

[11] Patent Number: 5,658,871
[45] Date of Patent: Aug. 19, 1997

[54] MICROBIAL LIPASE MUTEINS AND DETERGENT COMPOSITIONS COMPRISING SAME

[75] Inventors: Amir Maximiliaan Batenburg, Maassluis; Maarten Robert Egmond, Linschoten; Leon Gerardus Frenken, Rotterdam; Cornelis Theodorus Verrips, Maassluis, all of Netherlands

[73] Assignee: Lever Brothers Company, Division of Conopco, Inc., New York, N.Y.

[21] Appl. No.: 500,814

[22] Filed: Jul. 10, 1995

Related U.S. Application Data

[63] Continuation of Ser. No. 281,498, Jul. 27, 1994, abandoned, which is a continuation of Ser. No. 663,864, Mar. 7, 1991, abandoned.

[30] Foreign Application Priority Data

Jul. 7, 1989 [GB] United Kingdom ............... 8915658

[51] Int. Cl.⁶ .................................................. C11D 3/386
[52] U.S. Cl. .......................... 252/174.12; 252/DIG. 12; 435/196; 435/198; 435/69.1; 435/252.33; 435/320.1; 536/23.2
[58] Field of Search ............... 252/174.12, DIG. 12; 435/196, 198, 69.1, 252.33, 320.1; 536/23.2

[56] References Cited

U.S. PATENT DOCUMENTS

| | | | |
|---|---|---|---|
| 4,707,291 | 11/1987 | Thom et al. ............... | 252/174.12 |
| 4,760,025 | 7/1988 | Estell et al. ............... | 435/222 |
| 5,108,457 | 4/1992 | Poulouse et al. ............... | 8/11 |
| 5,133,893 | 7/1992 | Thom et al. ............... | 252/99 |

FOREIGN PATENT DOCUMENTS

| | | | |
|---|---|---|---|
| 0130756 | 1/1985 | European Pat. Off. ............... | 435/222 |
| 0157441 | 10/1985 | European Pat. Off. ............... | 435/320.1 |
| 0200451 | 11/1986 | European Pat. Off. ............... | 435/215 |
| 0206390 | 12/1986 | European Pat. Off. ............... | 252/174.12 |
| 0205208 | 12/1986 | European Pat. Off. ............... | 252/174.12 |
| 0208491 | 1/1987 | European Pat. Off. ............... | 435/172.3 |
| 0214761 | 3/1987 | European Pat. Off. ............... | 252/174.12 |
| 0214435 | 3/1987 | European Pat. Off. ............... | 435/222 |
| 0218272 | 8/1987 | European Pat. Off. ............... | 435/198 |
| 0243338 | 10/1987 | European Pat. Off. ............... | 536/23.2 |
| 0251446 | 1/1988 | European Pat. Off. ............... | 435/222 |
| 0258068 | 3/1988 | European Pat. Off. ............... | 252/174.12 |
| 0260105 | 3/1988 | European Pat. Off. ............... | 435/198 |
| 0268452 | 5/1988 | European Pat. Off. ............... | 435/198 |
| 0271153 | 6/1988 | European Pat. Off. ............... | 252/174.12 |
| 271154 | 6/1988 | European Pat. Off. ............... | 252/174.12 |
| 0290223 | 11/1988 | European Pat. Off. ............... | 252/174.12 |
| 0305216 | 3/1989 | European Pat. Off. ............... | 435/198 |
| 0331376 | 9/1989 | European Pat. Off. ............... | 536/23.2 |
| 8704461 | 7/1987 | WIPO ............... | 435/222 |
| 8705050 | 8/1987 | WIPO ............... | 435/222 |
| 8802775 | 4/1988 | WIPO ............... | 435/198 |
| 88-08033 | 10/1988 | WIPO ............... | 435/222 |
| 89-04361 | 5/1989 | WIPO ............... | 252/174.12 |
| 8906279 | 7/1989 | WIPO ............... | 435/221 |
| 8909263 | 10/1989 | WIPO ............... | 536/23.2 |

OTHER PUBLICATIONS

Svendsen, I., 1976, Carlsberg Research Communications, 41(5): 237–291.

Wells, J.A., et al., 1987, "Protein Engineering of Subtilisin", pp. 279–287, in *Protein Engineering*, Oxender, D.L., et al. Eds.

Wohlforth, S., et al., 1988, Journal of General Microbiology, 134: 433–440.

Poulouse, A.J., et al., 1988, Biological Abstracts Databank, Abstract 36061552.

*Primary Examiner*—Paul Lieberman
*Assistant Examiner*—Michael P. Tierney
*Attorney, Agent, or Firm*—Ronald A. Koatz

[57] ABSTRACT

Lipase enzymes including mutant lipase enzymes, e.g. from Pseudomonas species, are produced and modified by recombinant DNA technique. The enzymes are applicable in detergent and cleaning compositions, with advantages for example of improved stability to proteolytic digestion.

14 Claims, 59 Drawing Sheets

FIG. 2A

```
         C
         l
         a
         I
     ATGGTCAGATCGATGCGTTCCAGGGTGGCGGCGAGGGCGGTGGCATGGGCGTTGGCGGTG
  1  ---------+---------+---------+---------+---------+---------+  60
     TACCAGTCTAGCTACGCAAGGTCCCACCGCCGCTCCCGCCACCGTACCCGCAACCGCCAC

-39  M  V  R  S  M  R  S  R  V  A  A  R  A  V  A  W  A  L  A  V  -

ATGCCGCTGGCCGGCGCGGCCGGGTTGACGATGGCCGCGTCGCCCGCGGCCGTCGCGGCG
  61 ---------+---------+---------+---------+---------+---------+ 120
     TACGGCGACCGGCCGCGCCGGCCCAACTGCTACCGGCGCAGCGGGCGCCGGCAGCGCCGC

M  P  L  A  G  A  A  G  L  T  M  A  A  S  P  A  A  V  A  A  -
                              sig.seq.                    -1 ↑ 1

GACACCTACGCGGCGACGCGCTATCCGGTGATCCTCGTCCACGGCCTCGCGGGCACCGAC
 121 ---------+---------+---------+---------+---------+---------+ 180
     CTGTGGATGCGCCGCTGCGCGATAGGCCACTAGGAGCAGGTGCCGGAGCGCCCGTGGCTG

D  T  Y  A  A  T  R  Y  P  V  I  L  V  H  G  L  A  G  T  D  -
     mature lipase AAGTTCGCGAACGTGGTGGACTATTGGTACGGAATCCAGAGCGATCTGCAATCGCATGGC
 181 ---------+---------+---------+---------+---------+---------+ 240
     TTCAAGCGCTTGCACCACCTGATAACCATGCCTTAGGTCTCGCTAGACGTTAGCGTACCG

K  F  A  N  V  V  D  Y  W  Y  G  I  Q  S  D  L  Q  S  H  G  -

GCGAAGGTGTACGTCGCGAATCTCTCGGGATTCCAGAGCGACGACGGGCCGAACGGCCGC
 241 ---------+---------+---------+---------+---------+---------+ 300
     CGCTTCCACATGCAGCGCTTAGAGAGCCCTAAGGTCTCGCTGCTGCCCGGCTTGCCGGCG

A  K  V  Y  V  A  N  L  S  G  F  Q  S  D  D  G  P  N  G  R  -

P
                        v
                        u
                        I
                        I
     GGCGAGCAGCTGCTCGCCTACGTGAAGCAGGTGCTCGCGGCCACCGGCGCGACCAAGGTG
 301 ---------+---------+---------+---------+---------+---------+ 360
     CCGCTCGTCGACGAGCGGATGCACTTCGTCCACGAGCGCCGGTGGCCGCGCTGGTTCCAC

G  E  Q  L  L  A  Y  V  K  Q  V  L  A  A  T  G  A  T  K  V  -

AACCTGATCGGCCACAGCCAGGGCGGCCTGACCTCGCGCTACGTCGCGGCCGTCGCGCCG
 361 ---------+---------+---------+---------+---------+---------+ 420
     TTGGACTAGCCGGTGTCGGTCCCGCCGGACTGGAGCGCGATGCAGCGCCGGCAGCGCGGC

N  L  I  G  H  S  Q  G  G  L  T  S  R  Y  V  A  A  V  A  P  -

CAACTGGTGGCCTCGGTGACGACGATCGGCACGCCGCATCGCGGCTCCGAGTTCGCCGAC
 421 ---------+---------+---------+---------+---------+---------+ 480
     GTTGACCACCGGAGCCACTGCTGCTAGCCGTGCGGCGTAGCGCCGAGGCTCAAGCGGCTG

Q  L  V  A  S  V  T  T  I  G  T  P  H  R  G  S  E  F  A  D  -
```

FIG. 2B

```
                                                      S
                                                      a
                                                      l
                                                      I
     TTCGTGCAGGACGTGCTGAAGACCGATCCGACCGGGCTCTCGTCGACGGTGATCGCCGCC
481  ---------+---------+---------+---------+---------+---------+ 540
     AAGCACGTCCTGCACGACTTCTGGCTAGGCTGGCCCGAGAGCAGCTGCCACTAGCGGCGG

F  V  Q  D  V  L  K  T  D  P  T  G  L  S  S  T  V  I  A  A  -

TTCGTCAACGTGTTCGGCACGCTCGTCAGCAGCTCGCACAACACCGACCAGGACGCGCTC
541  ---------+---------+---------+---------+---------+---------+ 600
     AAGCAGTTGCACAAGCCGTGCGAGCAGTCGTCGAGCGTGTTGTGGCTGGTCCTGCGCGAG

F  V  N  V  F  G  T  L  V  S  S  S  H  N  T  D  Q  D  A  L  -

GCGGCGCTGCGCACGCTCACCACCGCGCAGACCGCCACCTACAACCGGAACTTCCCGAGC
601  ---------+---------+---------+---------+---------+---------+ 660
     CGCCGCGACGCGTGCGAGTGGTGGCGCGTCTGGCGGTGGATGTTGGCCTTGAAGGGCTCG

A  A  L  R  T  L  T  T  A  Q  T  A  T  Y  N  R  N  F  P  S  -

GCGGGCCTGGGCGCGCCCGGTTCGTGCCAGACGGGCGCCGCGACCGAAACCGTCGGCGGC
661  ---------+---------+---------+---------+---------+---------+ 720
     CGCCCGGACCCGCGCGGGCCAAGCACGGTCTGCCCGCGGCGCTGGCTTTGGCAGCCGCCG

A  G  L  G  A  P  G  S  C  Q  T  G  A  A  T  E  T  V  G  G  -

AGCCAGCACCTGCTCTATTCGTGGGGCGGCACCGCGATCCAGCCCACCTCCACCGTGCTC
721  ---------+---------+---------+---------+---------+---------+ 780
     TCGGTCGTGGACGAGATAAGCACCCCGCCGTGGCGCTAGGTCGGGTGGAGGTGGCACGAG

S  Q  H  L  L  Y  S  W  G  G  T  A  I  Q  P  T  S  T  V  L  -

GGCGTGACCGGCGCGACCGACACCAGCACCGGCACGCTCGACGTCGCGAACGTGACCGAC
781  ---------+---------+---------+---------+---------+---------+ 840
     CCGCACTGGCCGCGCTGGCTGTGGTCGTGGCCGTGCGAGCTGCAGCGCTTGCACTGGCTG

G  V  T  G  A  T  D  T  S  T  G  T  L  D  V  A  N  V  T  D  -

CCGTCCACGCTCGCGCTGCTCGCCACCGGCGCGGTGATGATCAATCGCGCCTCGGGGCAG
841  ---------+---------+---------+---------+---------+---------+ 900
     GGCAGGTGCGAGCGCGACGAGCGGTGGCCGCGCCACTACTAGTTAGCGCGGAGCCCCGTC

P  S  T  L  A  L  L  A  T  G  A  V  M  I  N  R  A  S  G  Q  -

P
                                         s
                                         t
                                         I
     AACGACGGGCTCGTCTCGCGCTGCAGCTCGCTGTTCGGGCAGGTGATCAGCACCAGCTAC
901  ---------+---------+---------+---------+---------+---------+ 960
     TTGCTGCCCGAGCAGAGCGCGACGTCGAGCGACAAGCCCGTCCACTAGTCGTGGTCGATG

N  D  G  L  V  S  R  C  S  S  L  F  G  Q  V  I  S  T  S  Y  -
```

FIG. 2C

```
                             P
                             v
                             u
                             I
                             I
       CACTGGAACCATCTCGACGAGATCAACCAGCTGCTCGGCGTGCGCGGCGCCAACGCGGAA
961    ---------+---------+---------+---------+---------+---------+ 1020
       GTGACCTTGGTAGAGCTGCTCTAGTTGGTCGACGAGCCGCACGCGCCGCGGTTGCGCCTT

H   W   N   H   L   D   E   I   N   Q   L   L   G   V   R   G   A   N   A   E   -

P
                                                          s
                                                          t
                                                          I
       GATCCGGTCGCGGTGATCCGCACGCACGTGAACCGGCTCAAGCTGCAGGGCGTGTGA
1021   ---------+---------+---------+---------+---------+------- 1077
       CTAGGCCAGCGCCACTAGGCGTGCGTGCACTTGGCCGAGTTCGACGTCCCGCACACT

D   P   V   A   V   I   R   T   H   V   N   R   L   K   L   Q   G   V   *   -
```

FIG. 5A

A. DNA sequence of synthetic lipase gene in pUR6038.

```
    E
    c                   C
    o                   l
    R                   a
    I                   I
    GAATTCATGGTTAGATCGATGCGTAGCCGTGTTGCAGCTAGAGCGGTCGCATGGGCATTA
 1  ---------+---------+---------+---------+---------+---------+  60
    CTTAAGTACCAATCTAGCTACGCATCGGCACAACGTCGATCTCGCCAGCGTACCCGTAAT

E  F  M  V  R  S  M  R  S  R  V  A  A  R  A  V  A  W  A  L  -
                                                 P
                                                 s
                                                 t
                                                 I
    GCTGTTATGCCATTAGCTGGAGCAGCAGGATTAACAATGGCTGCGTCTCCTGCAGCGGTC
 61 ---------+---------+---------+---------+---------+---------+ 120
    CGACAATACGGTAATCGACCTCGTCGTCCTAATTGTTACCGACGCAGAGGACGTCGCCAG

A  V  M  P  L  A  G  A  A  G  L  T  M  A  A  S  P  A  A  V  -
                                                 E
                                                 c
                                                 o
                                                 R
                                                 V
    GCTGCTGACACATATGCAGCTACGAGATATCCTGTGATCTTGGTTCACGGTTTGGCAGGA
121 ---------+---------+---------+---------+---------+---------+ 180
    CGACGACTGTGTATACGTCGATGCTCTATAGGACACTAGAACCAAGTGCCAAACCGTCCT

A  A  D  T  Y  A  A  T  R  Y  P  V  I  L  V  H  G  L  A  G  -

ACGGACAAGTTTGCCAATGTCGTTGACTACTGGTATGGTATCCAGTCAGATCTTCAATCT
181 ---------+---------+---------+---------+---------+---------+ 240
    TGCCTGTTCAAACGGTTACAGCAACTGATGACCATACCATAGGTCAGTCTAGAAGTTAGA

T  D  K  F  A  N  V  V  D  Y  W  Y  G  I  Q  S  D  L  Q  S  -

CACGGAGCTAAGGTTTACGTGGCCAATTTGAGCGGATTCCAGTCTGACGATGGCCCAAAC
241 ---------+---------+---------+---------+---------+---------+ 300
    GTGCCTCGATTCCAAATGCACCGGTTAAACTCGCCTAAGGTCAGACTGCTACCGGGTTTG

H  G  A  K  V  Y  V  A  N  L  S  G  F  Q  S  D  D  G  P  N  -
```

FIG. 5B

```
                P
                v
                u
                I
                I
     GGCCGCGGTGAACAGCTGCTTGCGTACGTCAAACAAGTACTTGCAGCTACGGGAGCTACG
301  ---------+---------+---------+---------+---------+---------+ 360
     CCGGCGCCACTTGTCGACGAACGCATGCAGTTTGTTCATGAACGTCGATGCCCTCGATGC

G  R  G  E  Q  L  L  A  Y  V  K  Q  V  L  A  A  T  G  A  T  -

AAGGTCAACTTGATCGGCCACTCTCAAGGTGGCCTTACATCTAGATACGTTGCTGCCGTG
361  ---------+---------+---------+---------+---------+---------+ 420
     TTCCAGTTGAACTAGCCGGTGAGAGTTCCACCGGAATGTAGATCTATGCAACGACGGCAC

K  V  N  L  I  G  H  S  Q  G  G  L  T  S  R  Y  V  A  A  V  -

GCTCCTCAGTTGGTCGCCAGCGTTACTACGATCGGTACGCCTCACAGAGGCTCTGAGTTC
421  ---------+---------+---------+---------+---------+---------+ 480
     CGAGGAGTCAACCAGCGGTCGCAATGATGCTAGCCATGCGGAGTGTCTCCGAGACTCAAG

A  P  Q  L  V  A  S  V  T  T  I  G  T  P  H  R  G  S  E  F  -

S
                                                              a
                                                              l
                                                              I
     GCTGACTTTGTGCAAGACGTCTTGAAGACTGACCCAACAGGACTTTCGTCGACGGTTATT
481  ---------+---------+---------+---------+---------+---------+ 540
     CGACTGAAACACGTTCTGCAGAACTTCTGACTGGGTTGTCCTGAAAGCAGCTGCCAATAA

A  D  F  V  Q  D  V  L  K  T  D  P  T  G  L  S  S  T  V  I  -

GCGGCTTTCGTTAACGTTTTCGGCACATTGGTTTCTAGCTCTCACAATACGGATCAGGAC
541  ---------+---------+---------+---------+---------+---------+ 600
     CGCCGAAAGCAATTGCAAAAGCCGTGTAACCAAAGATCGAGAGTGTTATGCCTAGTCCTG

A  A  F  V  N  V  F  G  T  L  V  S  S  H  N  T  D  Q  D  -

GCCCTTGCTGCATTGCGCACGCTTACAACGGCTCAGACTGCCACGTATAATAGAAACTTT
601  ---------+---------+---------+---------+---------+---------+ 660
     CGGGAACGACGTAACGCGTGCGAATGTTGCCGAGTCTGACGGTGCATATTATCTTTGAAA

A  L  A  A  L  R  T  L  T  T  A  Q  T  A  T  Y  N  R  N  F  -

CCAAGCGCTGGCTTGGGAGCTCCTGGTTCTTGTCAGACGGGCGCAGCTACAGAGACGGTT
661  ---------+---------+---------+---------+---------+---------+ 720
     GGTTCGCGACCGAACCCTCGAGGACCAAGAACAGTCTGCCCGCGTCGATGTCTCTGCCAA

P  S  A  G  L  G  A  P  G  S  C  Q  T  G  A  A  T  E  T  V  -
```

FIG. 5C

```
                                P
                                v
                                u
                                I
                                I
     GGAGGCTCTCAGCACTTGCTTTACAGCTGGGGAGGTACCGCAATTCAACCAACGTCTACT
721  ---------+---------+---------+---------+---------+---------+  780
     CCTCCGAGAGTCGTGAACGAAATGTCGACCCCTCCATGGCGTTAAGTTGGTTGCAGATGA

G  G  S  Q  H  L  L  Y  S  W  G  G  T  A  I  Q  P  T  S  T  -

GTGTTGGGCGTTACGGGAGCTACAGACACAAGCACTGGCACGCTTGATGTCGCGAATGTG
781  ---------+---------+---------+---------+---------+---------+  840
     CACAACCCGCAATGCCCTCGATGTCTGTGTTCGTGACCGTGCGAACTACAGCGCTTACAC

V  L  G  V  T  G  A  T  D  T  S  T  G  T  L  D  V  A  N  V  -

ACGGACCCTTCTACGTTGGCTCTTTTGGCTACGGGAGCGGTTATGATCAACCGTGCTTCT
841  ---------+---------+---------+---------+---------+---------+  900
     TGCCTGGGAAGATGCAACCGAGAAAACCGATGCCCTCGCCAATACTAGTTGGCACGAAGA

T  D  P  S  T  L  A  L  L  A  T  G  A  V  M  I  N  R  A  S  -
                                    X
                                    h
                                    o
                                    I
     GGACAGAATGACGGCCTTGTCTCGAGATGTAGCTCTTTGTTCGGCCAGGTTATTTCTACG
901  ---------+---------+---------+---------+---------+---------+  960
     CCTGTCTTACTGCCGGAACAGAGCTCTACATCGAGAAACAAGCCGGTCCAATAAAGATGC

G  Q  N  D  G  L  V  S  R  C  S  S  L  F  G  Q  V  I  S  T  -

TCTTACCACTGGAACCACTTGGATGAAATCAACCAACTTTTGGGTGTGAGAGGCGCCAAT
961  ---------+---------+---------+---------+---------+---------+  1020
     AGAATGGTGACCTTGGTGAACCTACTTTAGTTGGTTGAAAACCCACACTCTCCGCGGTTA

S  Y  H  W  N  H  L  D  E  I  N  Q  L  L  G  V  R  G  A  N  -

GCTGAGGACCCTGTTGCCGTCATTCGTACGCACGTCAACAGATTGAAACTTCAGGGAGTT
1021 ---------+---------+---------+---------+---------+---------+  1080
     CGACTCCTGGGACAACGGCAGTAAGCATGCGTGCAGTTGTCTAACTTTGAAGTCCCTCAA

A  E  D  P  V  A  V  I  R  T  H  V  N  R  L  K  L  Q  G  V  -
```

FIG. 5D

```
                              H
                              i
                    B         n
          P         a         d
          s         m         I
          t         H         I
          I         I         I
      TAATAGCTGCAGTTACTAGGATCCTCATTACAAGCTT
1081  ---------+---------+---------+------  1117
      ATTATCGACGTCAATGATCCTAGGAGTAATGTTCGAA

*
```

B. DNA sequence of 3'-end of synthetic lipase gene in pUR6600.

```
                                                              P
                                                              s
                                                              t
                                                              I
      GCTGAGGACCCTGTTGCCGTCATTCGTACGCACGTCAACAGATTGAAACTGCAGGGAGTT
1021  ---------+---------+---------+---------+---------+---------+ 1080
      CGACTCCTGGGACAACGGCAGTAAGCATGCGTGCAGTTGTCTAACTTTGACGTCCCTCAA

A  E  D  P  V  A  V  I  R  T  H  V  N  R  L  K  L  Q  G  V  -
```

```
      H
      i
      n
      d
      I
      I
      I
      TGAAGCTT
1081  --------  1088
      ACTTCGAA
      *
```

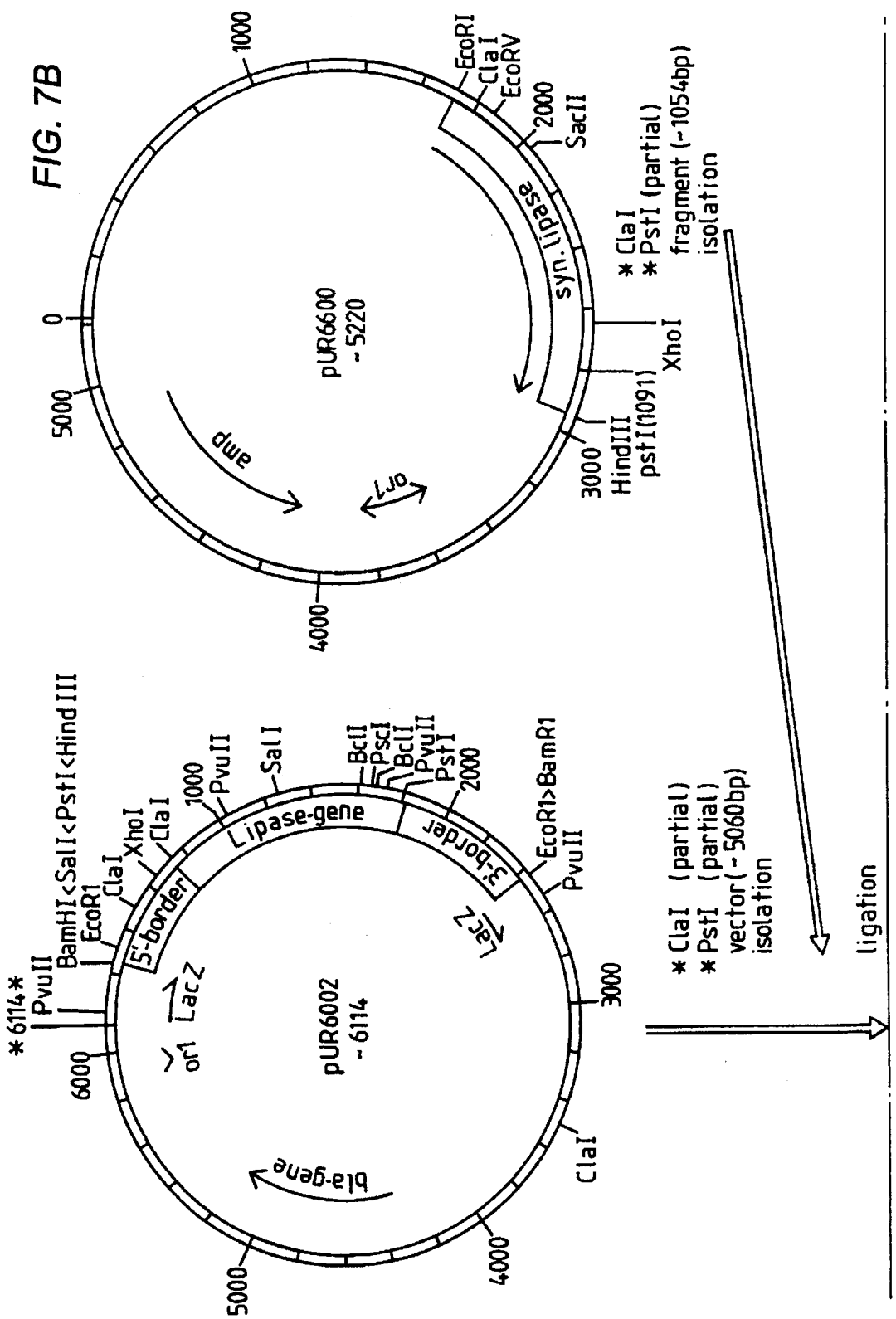

```
                    E
                    c
                    o
            S       R
         E  a       V
         c  c
         o  I
         R  I
         I  I
       1 aattcttccgcggatacatatgcagcaacaagat 34
         ----+----+----+----+----+----+----
         gaaggcgcctatgtatacgtcgttgttcta
         S  A D T Y  A A T R Y
``` pUR6038 → ligation → *3779* x EcoR1
x EcoR5
isolate vector pUR6752
-3779

Sac2
EcoR5
Sac2
synthetic
mature.lipase.gene
Hind 3
Amp

```
    E
    c
    o
    R
    I
    GAATTCGGTCTACTAAAATATTATTCCATACTATACAATTAATACACAGAATAATCTGTC
  1 ---------+---------+---------+---------+---------+---------+ 60
    CTTAAGCCAGATGATTTTATAATAAGGTATGATATGTTAATTATGTGTCTTATTAGACAG

TATTGGTTATTCTGCAAATGAAAAAAAGGAGAGGATAAAGAGTGAGAGGCAAAAAAGTAT
 61 ---------+---------+---------+---------+---------+---------+ 120
    ATAACCAATAAGACGTTTACTTTTTTTCCTCTCCTATTTCTCACTCTCCGTTTTTTCATA

M  R  G  K  K  V  W -

S
                                               a
                                               l
                                               I
    GGATCAGTTTGCTGTTTGCTTTAGCGTTAATCTTTACGATGGCGTTCGGGTCGACATCCT
121 ---------+---------+---------+---------+---------+---------+ 180
    CCTAGTCAAACGACAAACGAAATCGCAATTAGAAATGCTACCGCAAGCCCAGCTGTAGGA

I  S  L  L  F  A  L  A  L  I  F  T  M  A  F  G  S  T  S  S -

CTGCCCAGGCGGCAGGGAAATCAAACGGGGAAAAGAAATATATTGTCGGGTTTAAACAGA
181 ---------+---------+---------+---------+---------+---------+ 240
    GACGGGTCCGCCGTCCCTTTAGTTTGCCCCTTTTCTTTATATAACAGCCCAAATTTGTCT

A  Q  A  A  G  K  S  N  G  E  K  K  Y  I  V  G  F  K  Q  T -

CAATGAGCACGATGAGCGCCGCTAAGAAGAAAGACGTCATTTCTGAAAAAGGCGGGAAAG
241 ---------+---------+---------+---------+---------+---------+ 300
    GTTACTCGTGCTACTCGCGGCGATTCTTCTTTCTGCAGTAAAGACTTTTTCCGCCCTTTC

M  S  T  M  S  A  A  K  K  K  D  V  I  S  E  K  G  G  K  V -

TGCAAAAGCAATTCAAATATGTAGACGCAGCTTCAGCTACATTAAACGAAAAAGCTGTAA
301 ---------+---------+---------+---------+---------+---------+ 360
    ACGTTTTCGTTAAGTTTATACATCTGCGTCGAAGTCGATGTAATTTGCTTTTTCGACATT

Q  K  Q  F  K  Y  V  D  A  A  S  A  T  L  N  E  K  A  V  K -
```

FIG. 12B

```
         S
         a
         c
         I
    AAGAGCTCAAAAAAGACCCGAGCGTCGCTTACGTTGAAGAAGATCACGTAGCACATGCGT
361 ---------+---------+---------+---------+---------+---------+ 420
    TTCTCGAGTTTTTTCTGGGCTCGCAGCGAATGCAACTTCTTCTAGTGCATCGTGTACGCA

E  L  K  K  D  P  S  V  A  Y  V  E  E  D  H  V  A  H  A  Y -

ACGCGCAAACGGTACCTTATGGTATACCGTTGATTAAAGCGGATAAAGTGCAGGCGCAAG
421 ---------+---------+---------+---------+---------+---------+ 480
    TGCGCGTTTGCCATGGAATACCATATGGCAACTAATTTCGCCTATTTCACGTCCGCGTTC

A  Q  T  V  P  Y  G  I  P  L  I  K  A  D  K  V  Q  A  Q  G -

GTTTCAAAGGTGCAAACGTGAAAGTGGCAGTTCTAGACACAGGTATACAGGCCTCGCATC
481 ---------+---------+---------+---------+---------+---------+ 540
    CAAAGTTTCCACGTTTGCACTTTCACCGTCAAGATCTGTGTCCATATGTCCGGAGCGTAG

F  K  G  A  N  V  K  V  A  V  L  D  T  G  I  Q  A  S  H  P -

H
                                                              i
                                                              n
                                                              d
                                                              I
                                                              I
                                                              I
    CAGATCTCAATGTGGTCGGAGGTGCAAGCTT
541 ---------+---------+---------+- 571
    GTCTAGAGTTACACCAGCCTCCACGTTCGAA

D  L  N  V  V  G  G  A  S
```

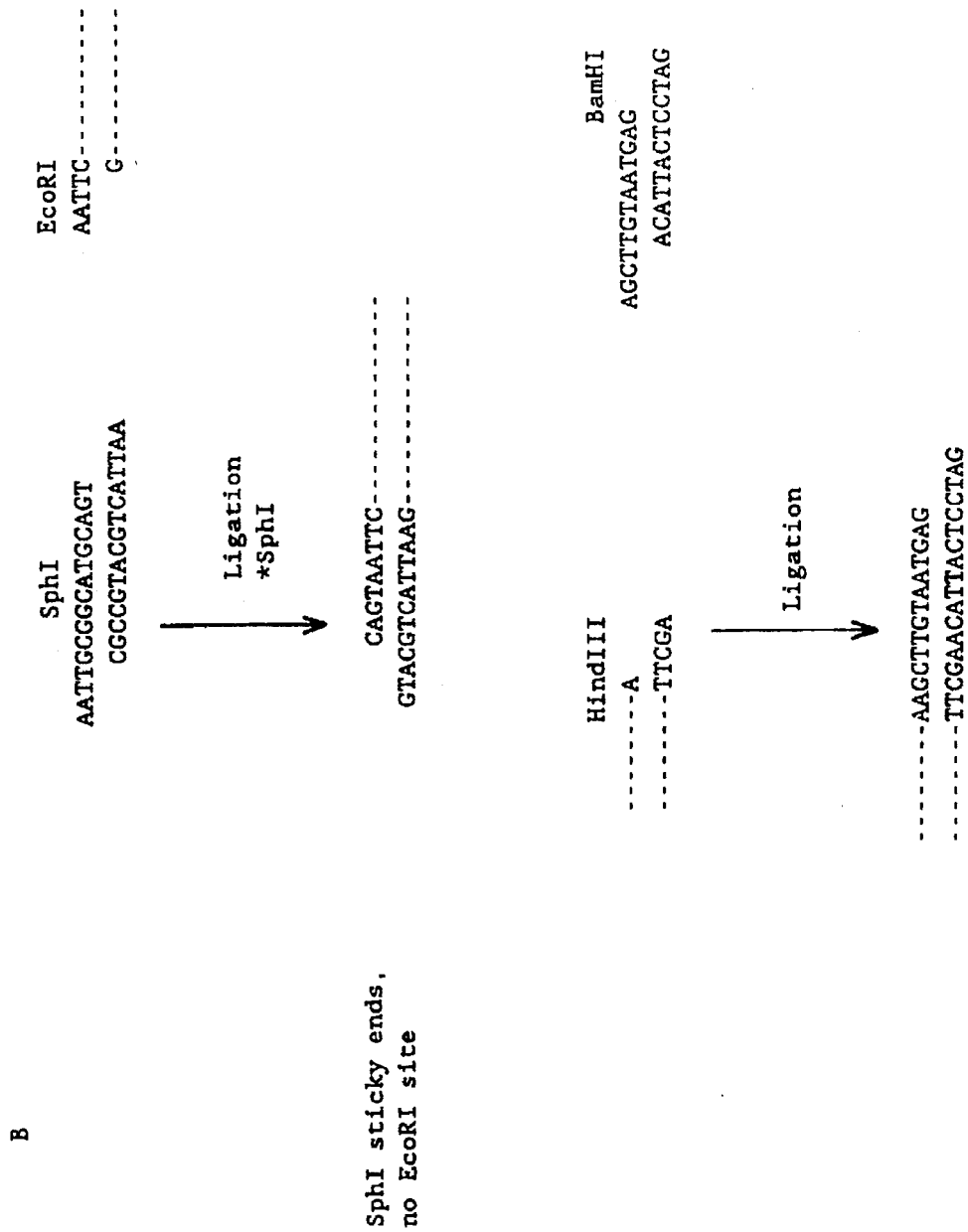

FIG. 16

Figure 16A:
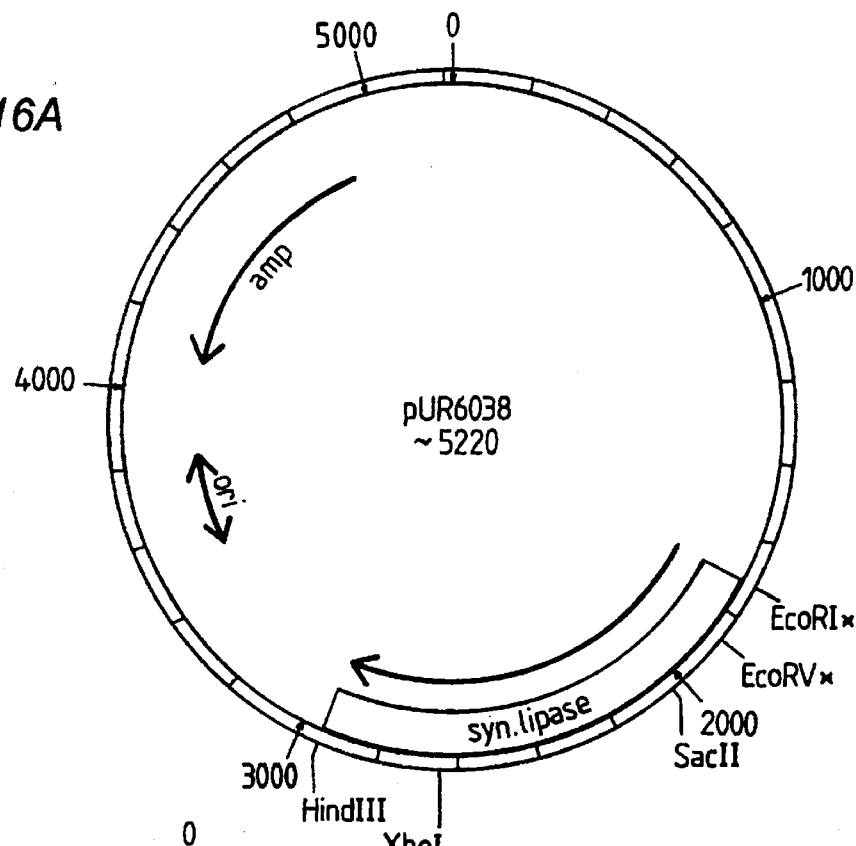
Figure 16B:
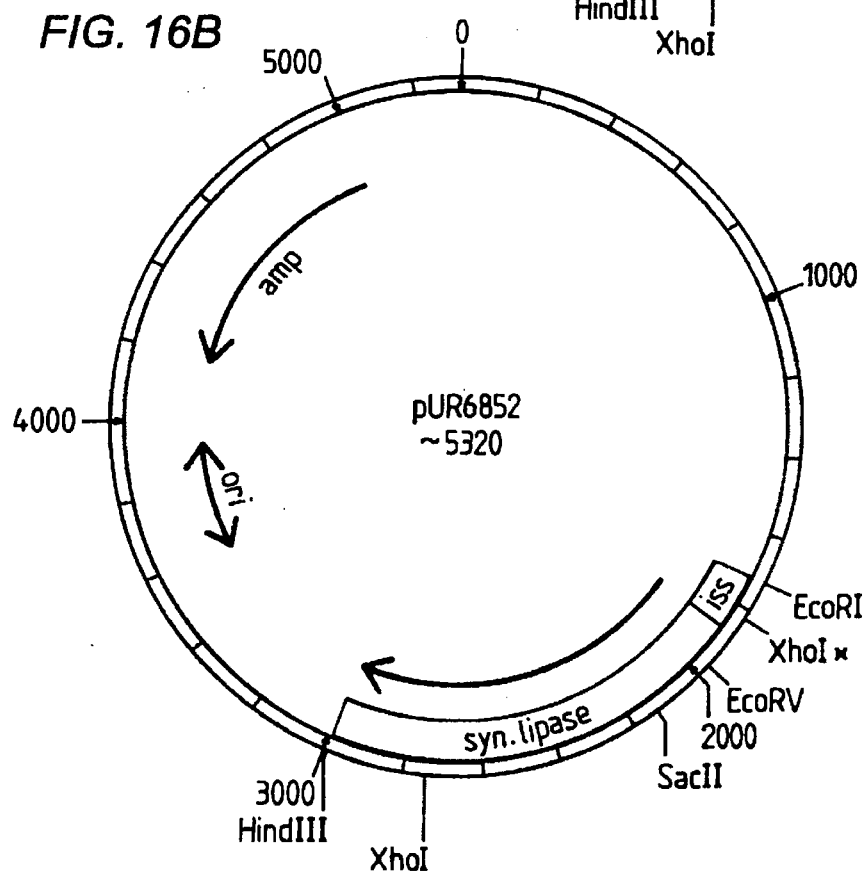
Figure 16C:
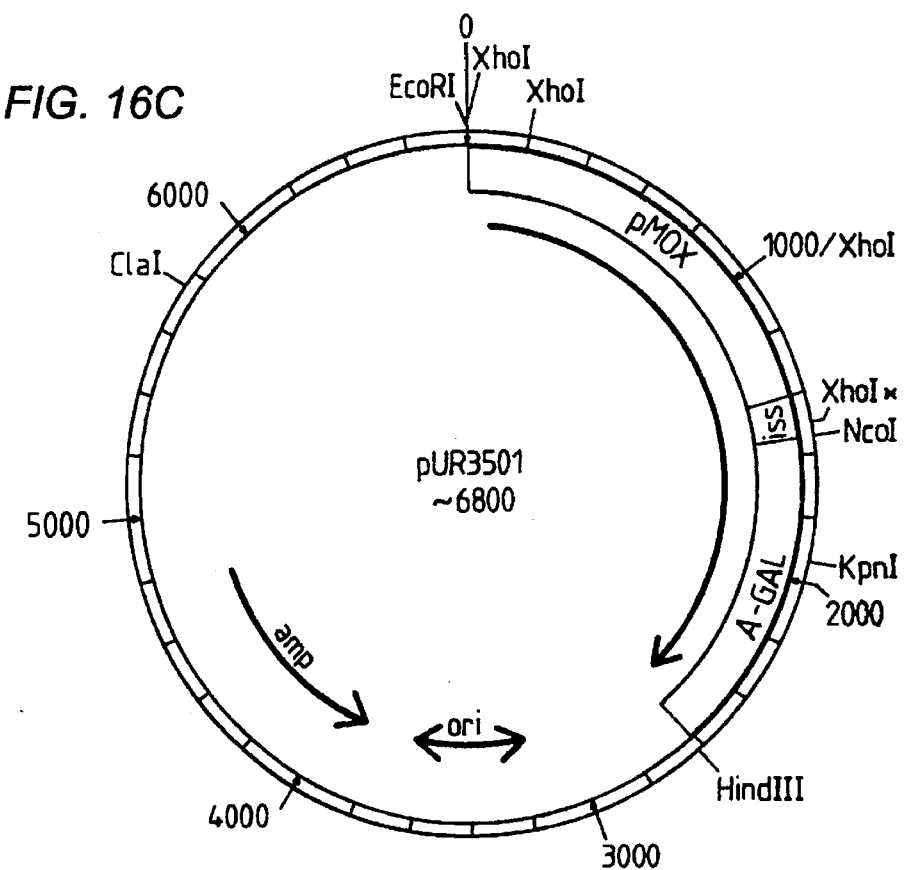
Figure 16D:
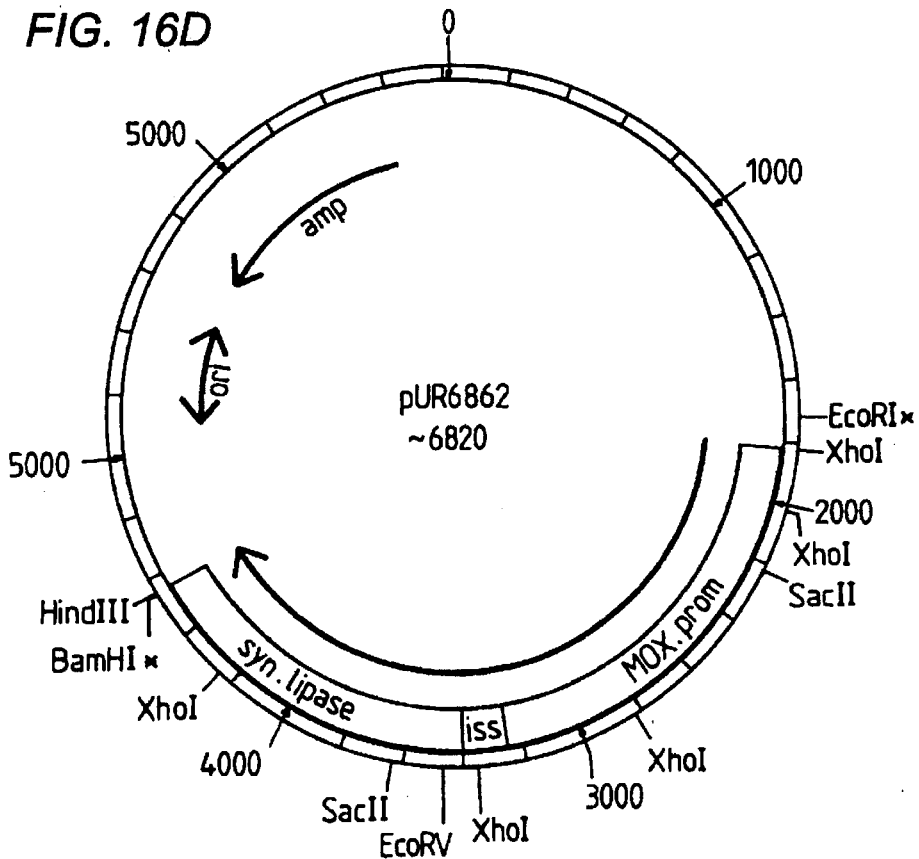
Figure 16E:
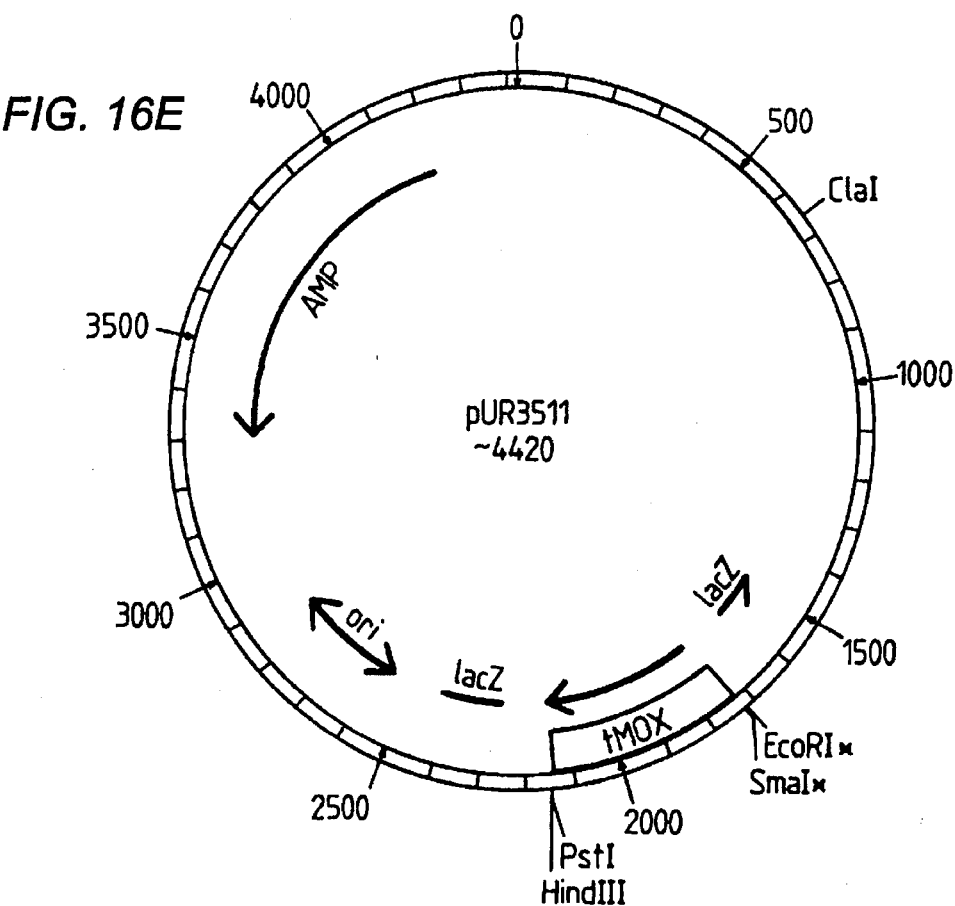

```
pUR6038 (fig. 16A)
     x EcoRI
     x EcoRV
     isolate vector fragment invertase signal sequence ———»  «——— lipase
                                       -13
                      K  I  S  A  A  G
     A: EcoRI-XhoI....AAGATCTCCGCCGCAGGG..........EcoRV
                                       -7
                      K  I  S  A  A  S
     B: EcoRI-XhoI....AAGATCTCCGCCGCATCT..........EcoRV
                                       +1
                      K  I  S  A  A  D
     C: EcoRI-XhoI....AAGATCTCCGCCGCAGAC..........EcoRV ligate EcoRI-EcoRV fragments pUR6850                                  pUR3501 (fig.16C)
pUR6851                                      x XhoI, partial,
pUR6852 (fig. 16B)                            isolate 1500 bp
                                              fragment.
     x XhoI, partial, isolate vector fragment pUR6860
pUR6861
pUR6862 (fig. 16D)                       pUR3511 (fig.16E)
                                             x SmaI
     x BamHI, Klenow filled in                x EcoRI
     x EcoRI                                   isolate
     isolate 2500 bp fragment              vector fragment pUR3513 (fig.16G)                        pUR6870
    x PvuII                               pUR6871
                                          pUR6872 (fig.16F)
                                          xEcoRI
                                          xHindIII
                                          Klenow filled in
                                          isolate 3000 bp fragment pUR6880
             pUR6881
             pUR6882 (fig.16H)
```

Figure 18B:
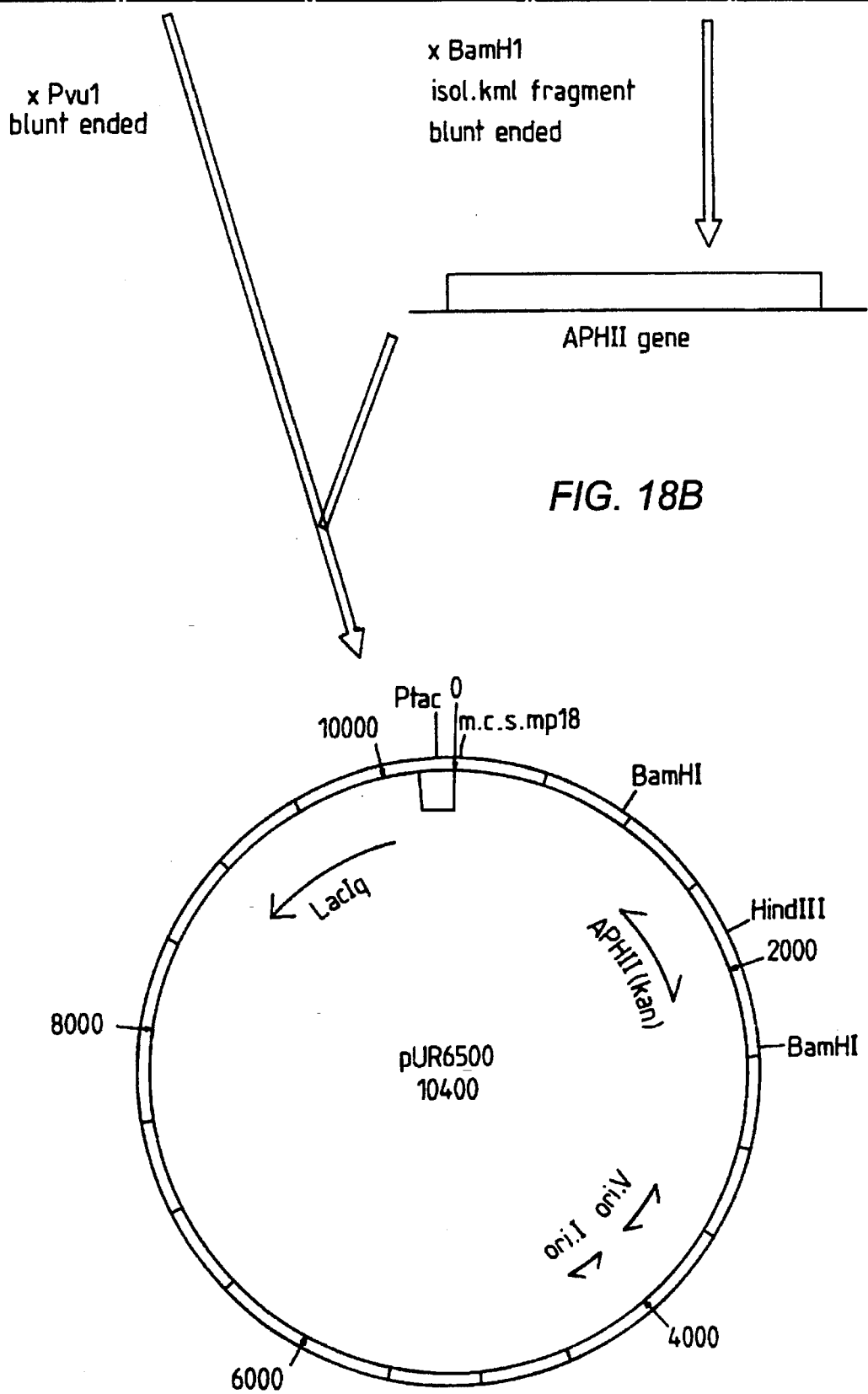
Figure 19A:
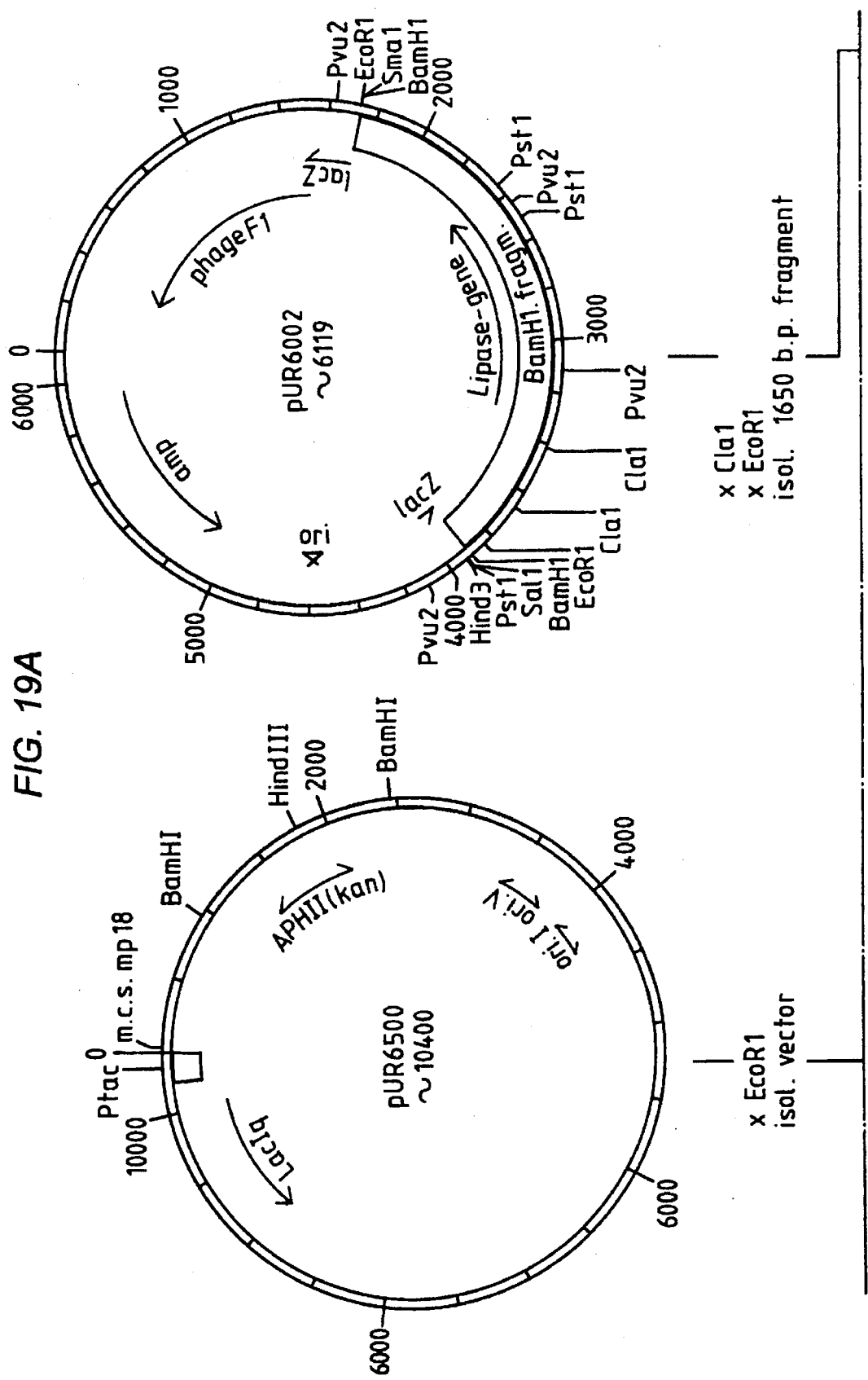
Figure 19B:
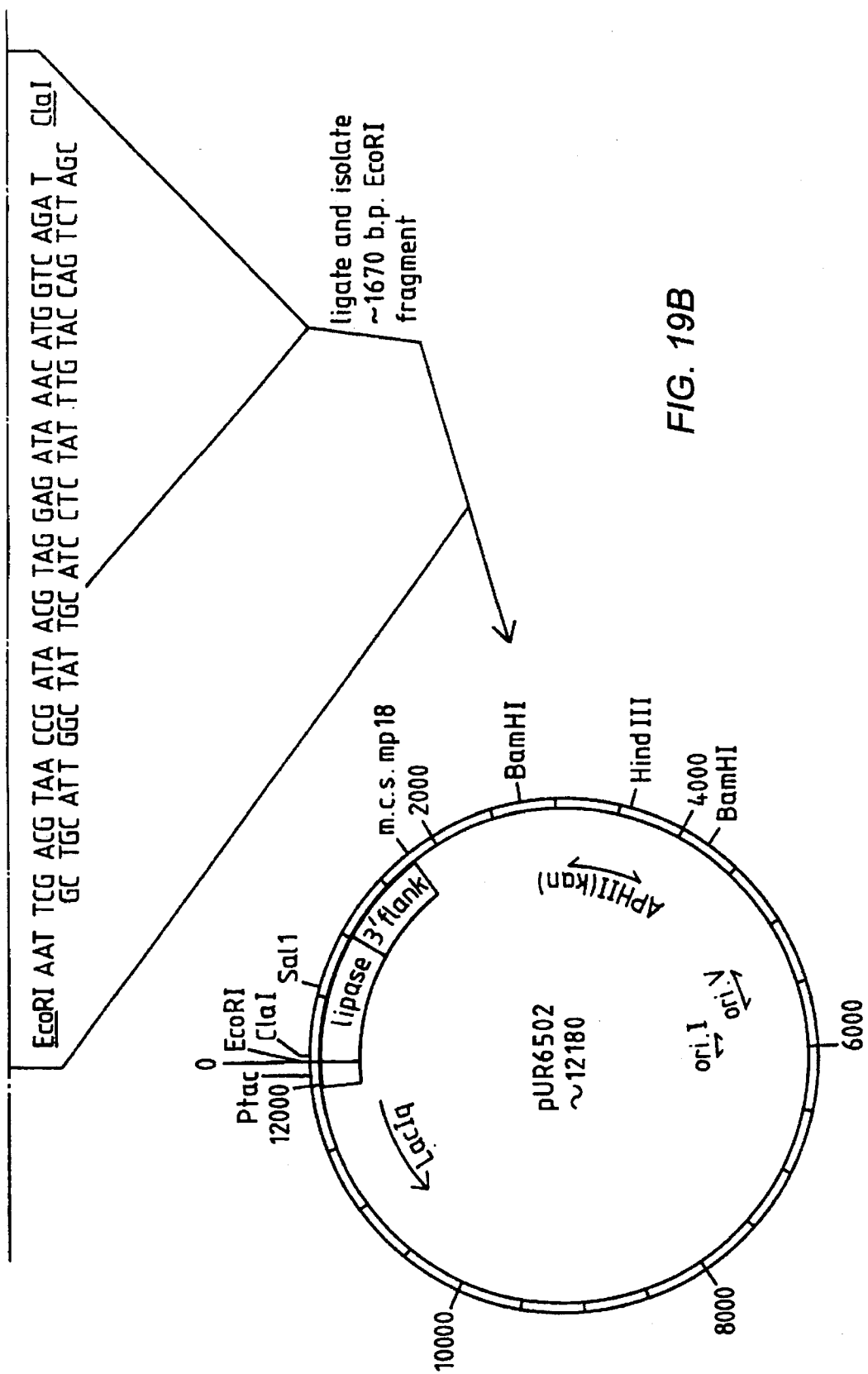
Figure 24:
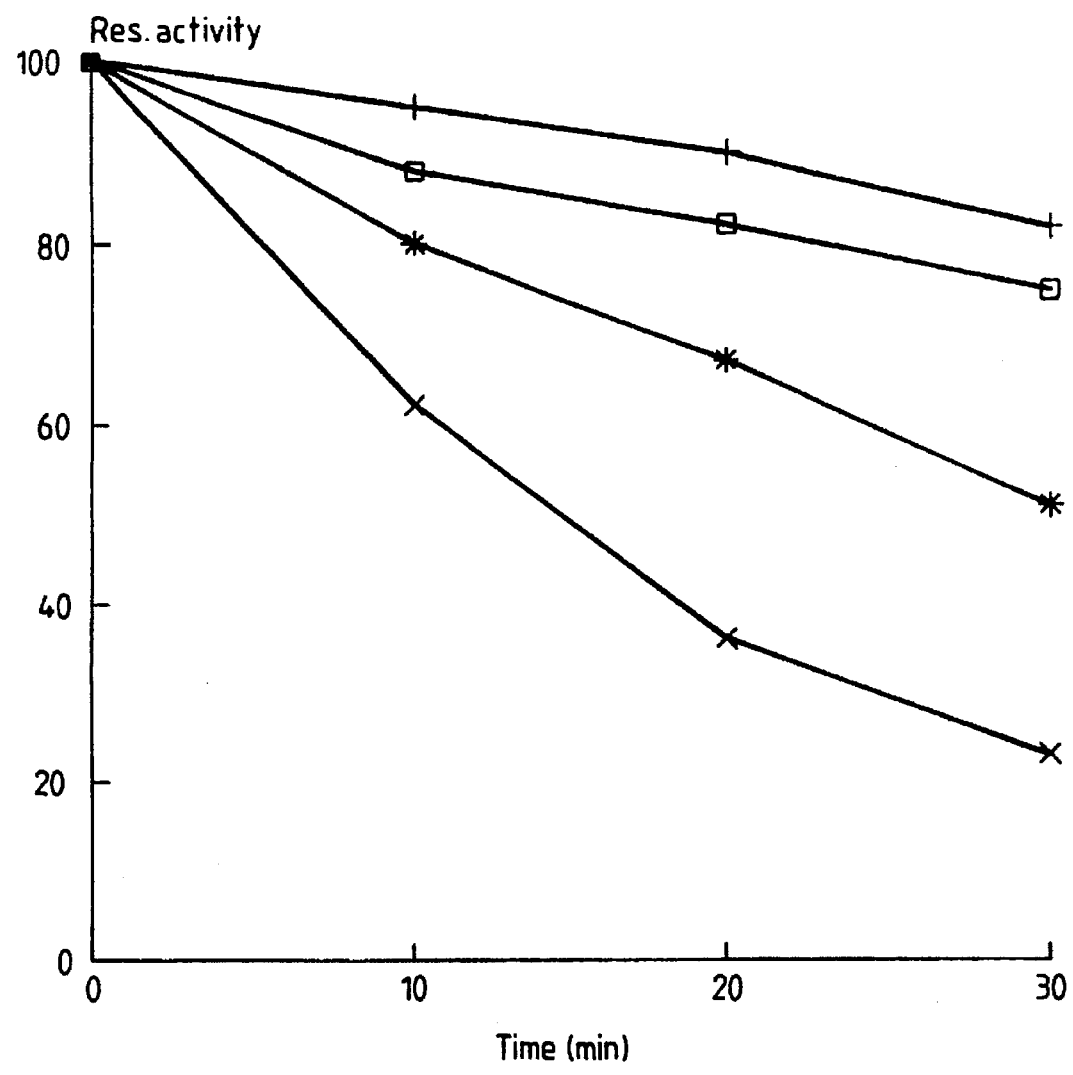
Figure 25:
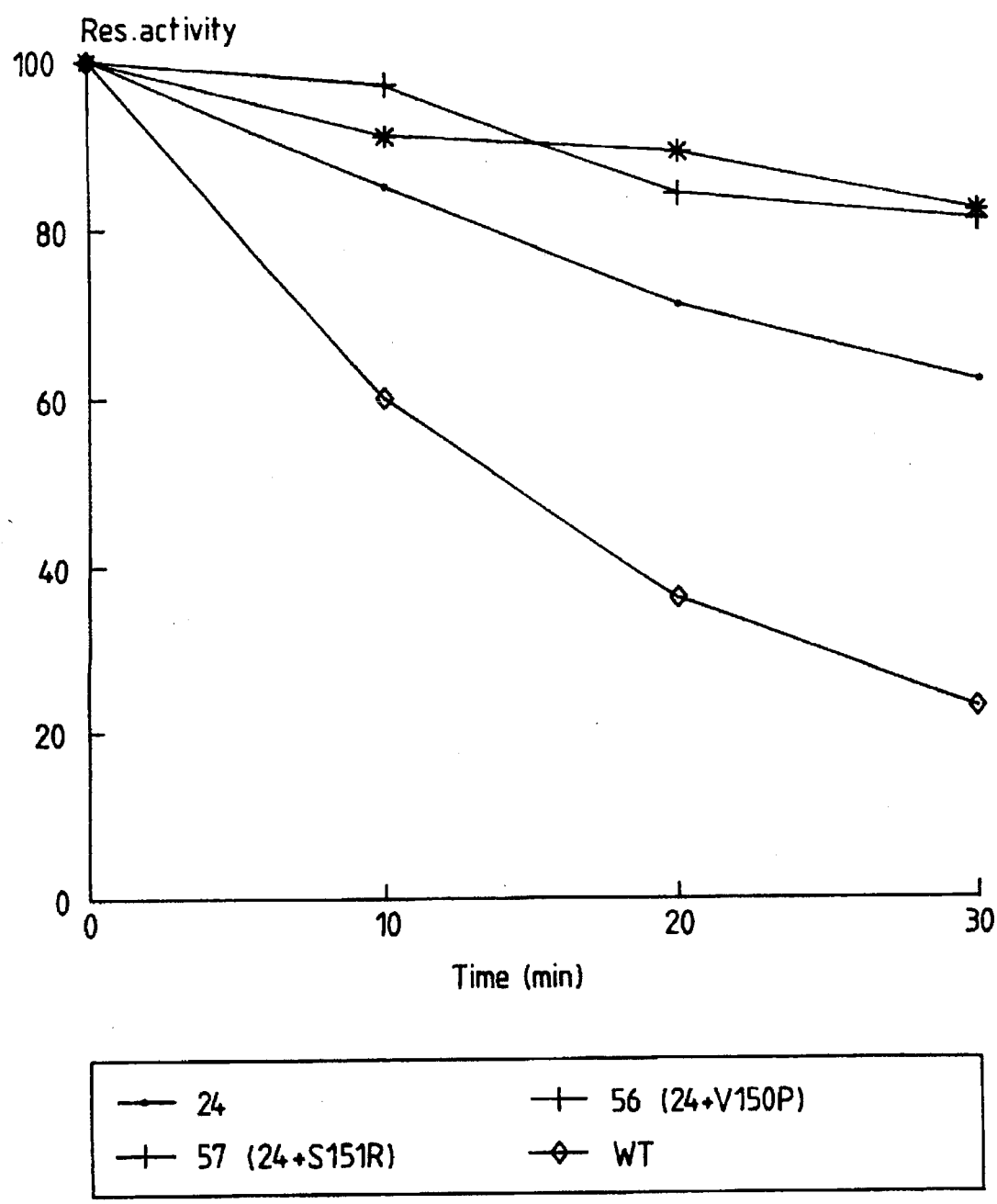

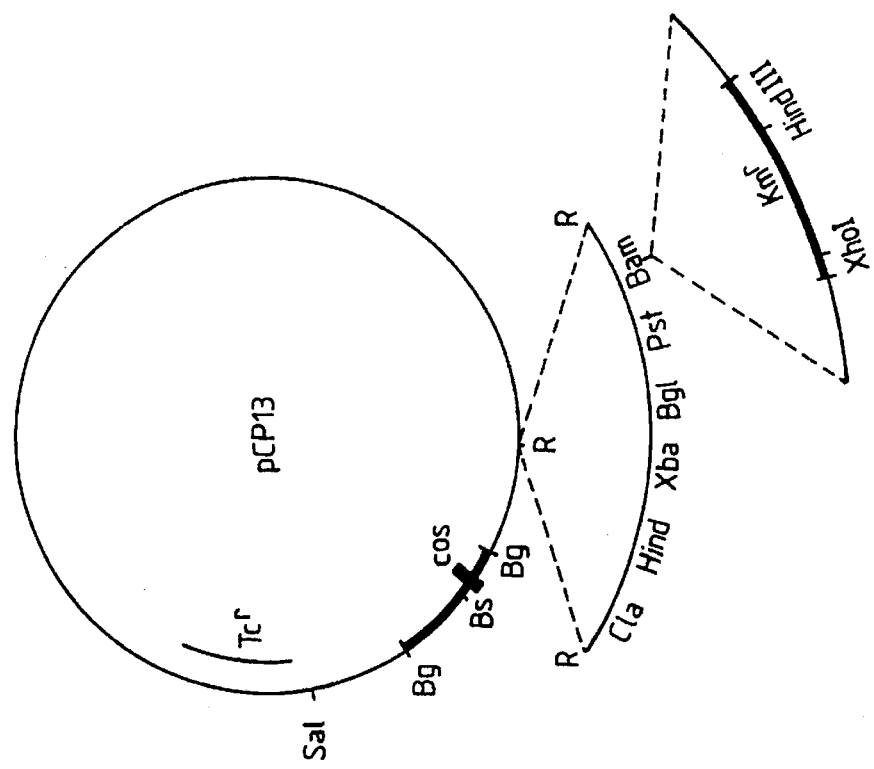
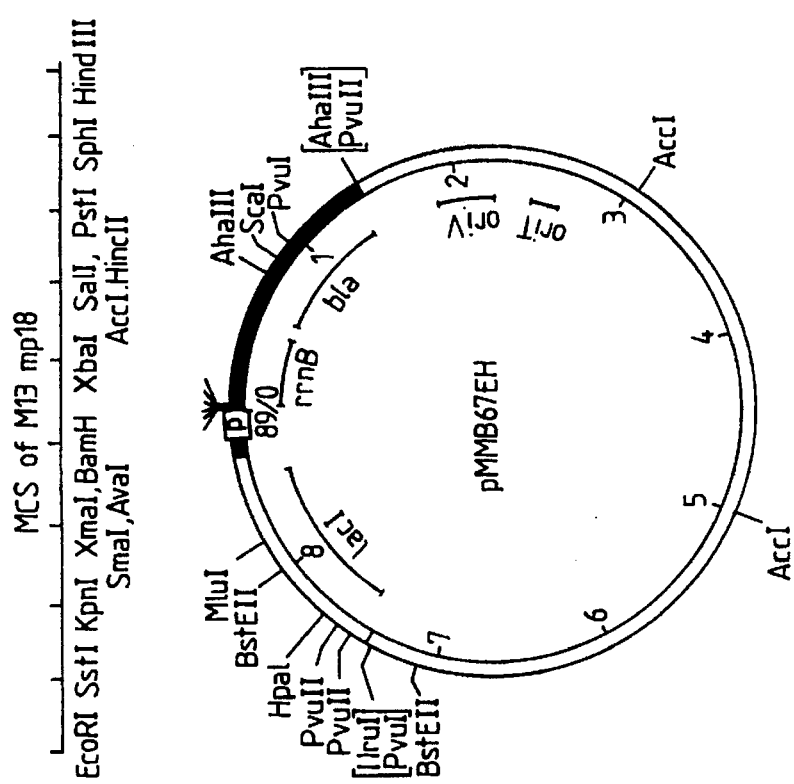
FIG. 18A

FIG. 20
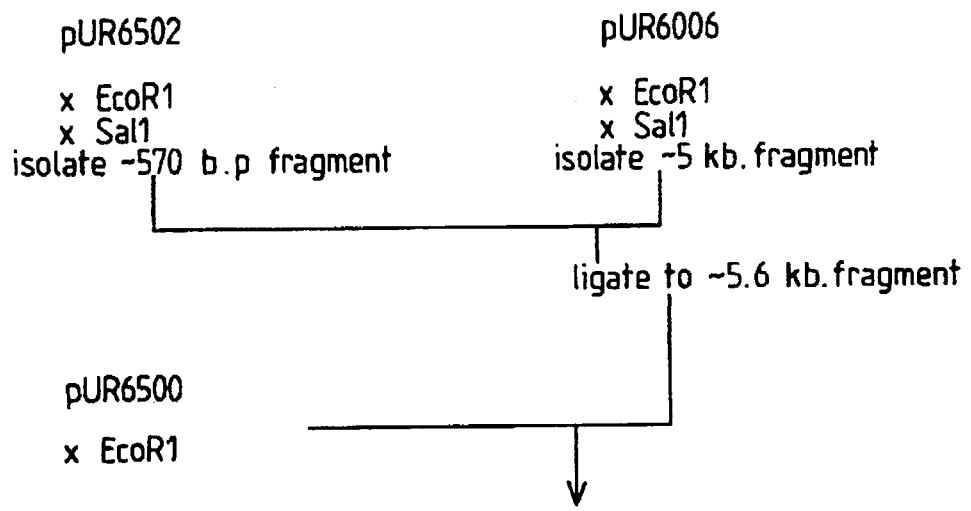
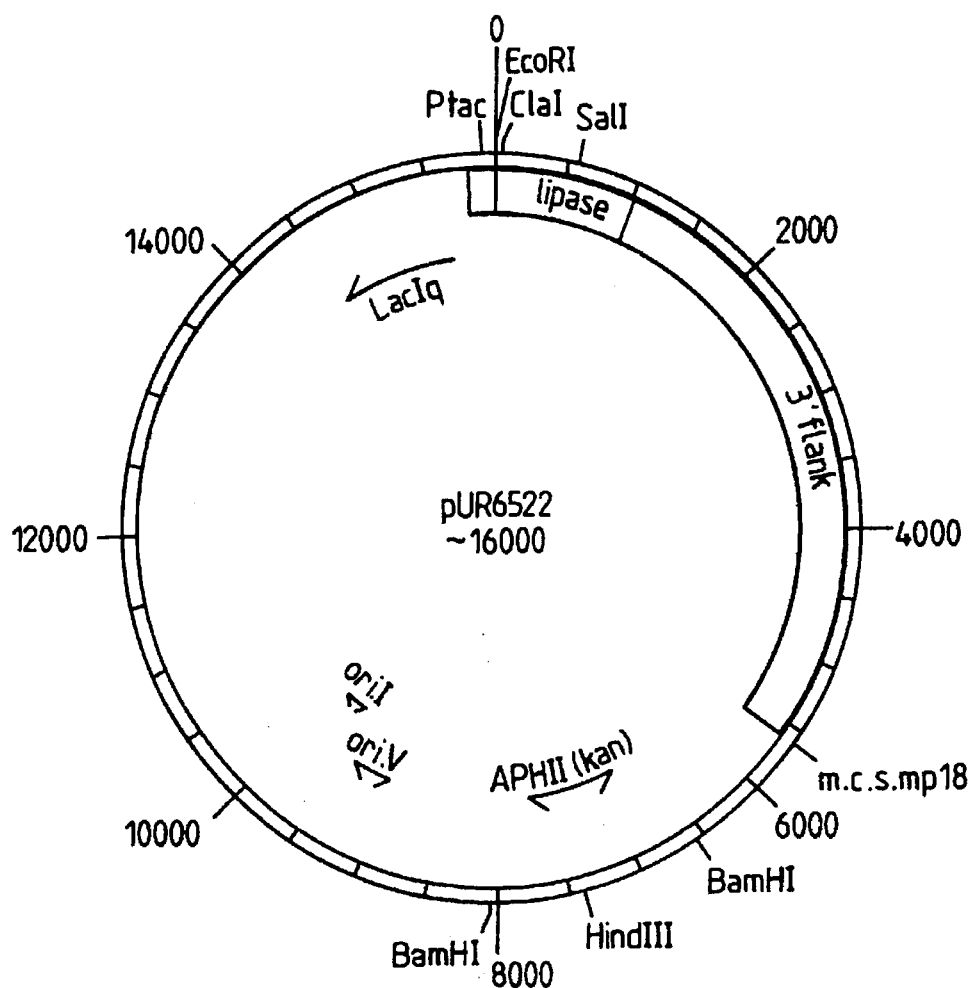

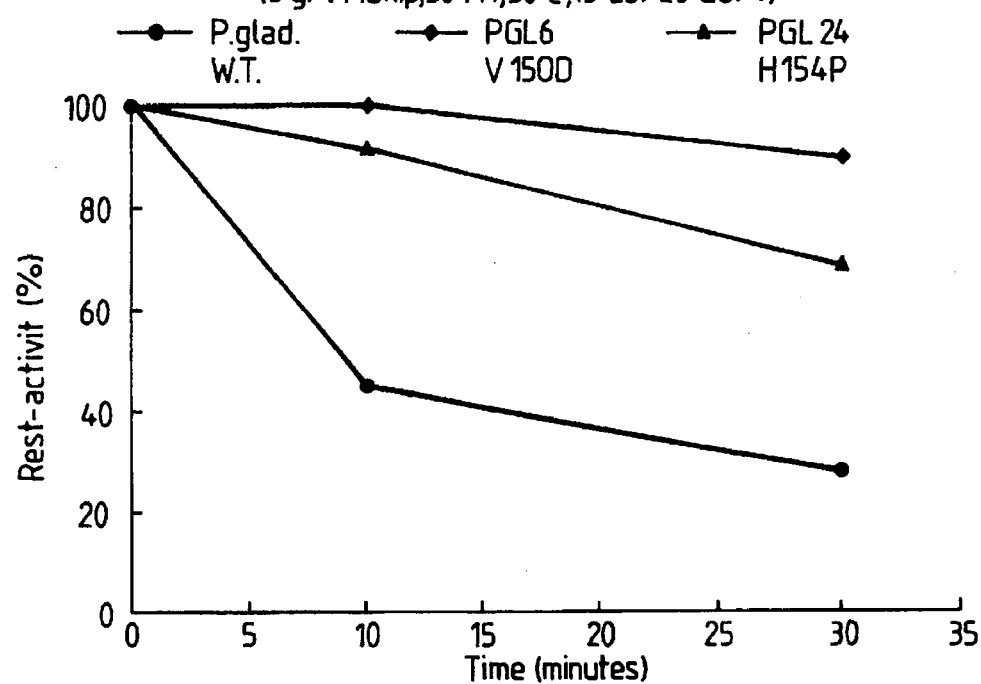
FIG. 23  Savinase degradation of PGL 6 and 24
(5 g/l F.Skip, 30 FH, 30 C, 15 LU/20 GU/1)
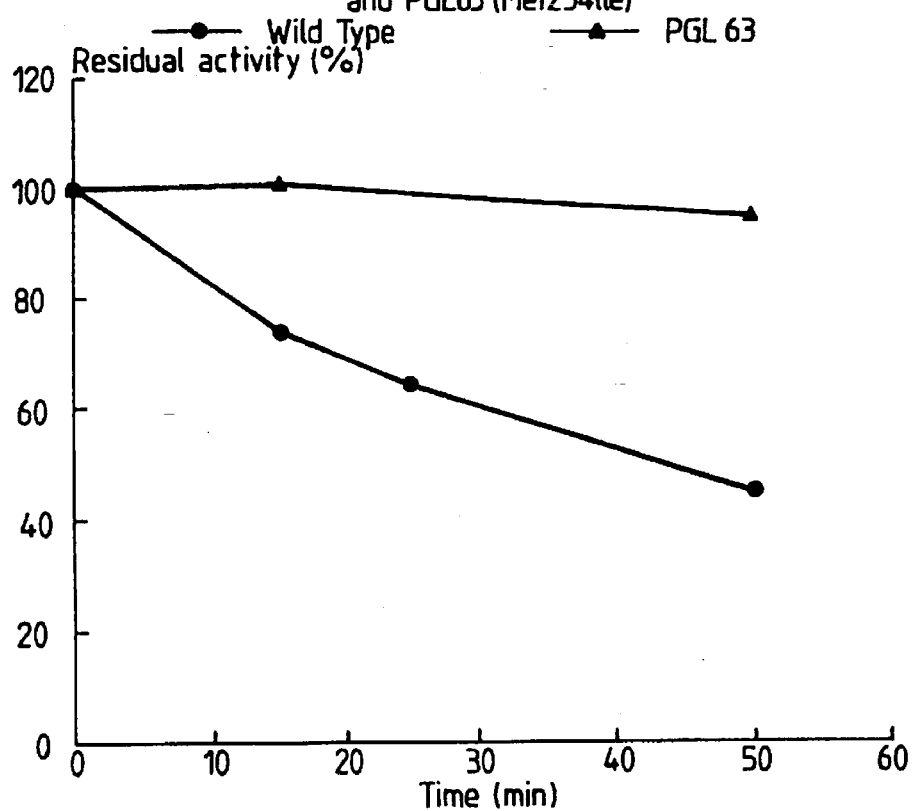
FIG. 26  Oxidative degradation of P.gladioli W.T. and PGL63 (Met254Ile)

MICROBIAL LIPASE MUTEINS AND DETERGENT COMPOSITIONS COMPRISING SAME

This is a continuation application of Ser. No. 08/281,498, filed Jul. 27, 1994, now abandoned, which is a continuation application of Ser. No. 07/663,864, filed Mar. 7, 1991 now abandoned.

This invention relates to enzymes, to recombinant DNA (hereinafter) rDNA techniques applicable for example for their modification and production and to their use in for example enzymatic detergent and cleaning compositions.

In particular the invention relates to the preparation and use of modified enzymes, especially modified lipases. Thus the invention as described below provides inter alia techniques for production of lipase, e.g. lipases of the Genus Pseudomonas, e.g. lipase from *P. glumae* (alias *P. gladioli*) and further provides genetically modified forms of such lipases and the use of such enzymes in detergent and cleaning compositions.

PRIOR ART

Lipases and proteases are both known as ingredients of detergent and cleaning compositions. Proteases are widely used.

Examples of known lipase-containing detergent compositions are provided by EPA 0 205 208 and EPA 0 206 390 (Unilever) which relates to a class of lipases defined on the basis of their immunological relationships, and describes their use in detergent compositions and textile washing. The preferred lipases are those from *Ps. fluorescens, Ps. gladioli* and Chromobacter species.

EP 0 214 761 (Novo) and EP 0 258 068 (Novo) each give detailed description of lipases from certain microorganisms, and also certain uses of detergent additives and detergent compositions for the enzymes described. EP 0 214 761 gives detailed description of lipases derived from organisms of the species *Ps. cepacia*, and certain uses therefor. EP 0 258 068 gives detailed description of lipases derived from organisms of the genus Thermomyces (previous name Humicola) and certain uses therefor.

EP 0 258 068 and EP 0 305 216 (Novo) both describe production of fungal lipase via heterologous host microorganisms by rDNA technique, especially lipase corresponding to that *Thermomyces lanuginosus/Humicola lanuginosa*.

EP 0 331 376 (Amano) describes lipases and their Production by rDNA technique, and their use, including an aminoacid sequence of lipase from *Pseudomonas cepacia*.

Further lipase enzymes produced by rDNA technique are described in for example WO 89-09263 (Gist-Brocades) and EP 0 218 272 (Gist-Brocades).

Recombinant DNA technique applied to other enzymes is mentioned for example and techniques described in WO 88/02775 (Novo), EP 0 243 338. (Labofina), EP 0 268 452 (Genencor), EP 0 305 216 (Novo) and WO 89/09263 (Gist-Brocades). EP 0 130 756 (Genentech) (corresponding to U.S. Pat. No. 4,760,025 (Genencor), EP 0 214 435 (Henkel), WO 87/04461 (Amgen), WO 89/05050(Genex), EPA 87303761 (Genentech), and WO 89/06279 (Novo), among others, describe modified subtilisin proteases produced by rDNA technique. EP 0 157 441 (Kok J. et al) also describes rDNA techniques applicable to the production of enzymes from *Bacillus subtilis*.

A difficulty with the simultaneous incorporation of both lipases and proteases into detergent compositions is that the protease tends to attack the lipase.

Measures have been proposed to mitigate this disadvantage.

One such attempt is represented by EP 0 271 154 (Unilever) wherein certain selected proteases with isoelectric points less than 10 are shown to combine advantageously with lipases.

Another attempt is described in WO 89/04361 (Novo), which concerns detergent compositions containing a lipase from Pseudomonas species and a protease from Fusarium or protease of subtilisin type which has been mutated in its amino acid sequence at positions 166, 169, or 222 in certain ways. It was reported that there was some reduction in the degree of attack upon the lipase by the particular proteases described.

THE PRESENT INVENTION

The invention in one of its aspects provides lipase produced from a microorganism by rDNA technique, and carrying at least one mutation of its aminoacid sequence conferring improved performance in use, e.g. by improved stability against attack by protease and/or oxidising agents and/or increased activity by comparison with the corresponding parent enzyme.

Lipases produced according to the invention can bring advantage in both activity and stability when used as part of detergent or cleaning compositions.

It is believed that until now there has been no published suggestion that changes in the amino acid sequence of lipases could give beneficial results.

We have found that mutations introduced by rDNA techniques can result in a better lipase stability in detergent compositions containing proteases and bleaching systems as well as such mutant lipase.

In the context of this invention, a mutated or mutant enzyme means an enzyme that has been produced by a mutant organism which is expressing a mutant gene. A mutant gene (other than one containing only silent mutations) means a gene encoding a enzyme having an aminoacid sequence which has been derived directly or indirectly, and which in one or more locations is different, from the sequence of a corresponding parent enzyme. The parent enzyme means the gene product of the corresponding unaltered gene. A silent mutation in a gene means a change or difference produced in the polynucleotide sequence of the gene which (owing to the redundancy in the codon-aminoacid relationships) leads to no change in the aminoacid sequence of the enzyme encoded by that gene.

A mutant or mutated micro-organism means a microorganism that is, or is descended from, a parent microorganism subjected to mutation in respect of its gene for the enzyme. Such mutation of the organism may be carried out either (a) by mutation of a corresponding gene (parent gene) already present in the parent microorganism, or (b) by the transfer (introduction) of a corresponding gene obtained directly or indirectly from another source, and then introduced (with or without mutation of the transferred gene) into the microorganism which is to become the mutant microorganism. A host microorganism is a microorganism of which a mutant gene, or a transferred gene of other origin, forms part. In general it may be of the same or different strain or species origin or descent as the parent microorganism.

For example, the invention provides mutant forms of lipases showing immunological cross-reactivity with antisera raised against lipases from *Chromobacter viscosum* var. *lipolyticum* NRRLB-3673, or against lipase from Alcaligenes PL-679, ATCC 31371 or FERM-P 3783 or against lipase from *Pseudomonas fluorescens* IAM 1057 and produced by an artificially modified microorganism containing a gene made by rDNA techniques which carries at least one mutation affecting the amino acid sequence of the lipase thereby to confer upon the lipase improved stability against attack by protease.

More generally, the lipase to serve as the basis for useful mutation can be chosen from a wide range of lipases: in particular the lipases described in for example the following patent specifications, EP 0 214 761 (Novo), EP 0 258 068 (Novo) and in particular lipases showing immunological cross reactivity with antisera raised against lipase from *Thermomyces lanuginosus* ATCC 22070; lipases as described in EP 0 205 208 and 0 206 930 (Unilever); lipases showing immunological cross-reactivity with antisera raised against lipase from *Chromobacter viscosum* var *lipolyticum* NRRL B-3673 or against lipase from Alcaligenes PL-679, ATCC 31371 and FERM-P 3783; lipases described in patent specifications WO 87/00859 (Gist Brocades) and EPA 0 204 284 (Sapporo Breweries). Suitable in particular are for example lipases corresponging to the following commercially available lipase preparations: NOVO Lipolase, Amano lipases CE, P, AP, M-AP, AML and CES and Meito lipases MY-30, OF and PL and also esterase MM, Lipozym, SP 225, SP 285, Enzeco lipase, Toyo Jozo lipase and Diosynth lipase (trade Marks).

Modified lipases can for example be produced in which part of the nucleotide sequence has been replaced by a substantially corresponding part of a nucleotide sequence encoding another lipase, immunologically related to the first.

Correspondingly, artificially modified microorganisms according to the present invention can be produced on the basis of the following parent organisms among others, for example, from *Escherichia coli, Pseudomonas aeruginosa, Ps. putida* and modified strains of *Ps. glumae* in which the original gene for the lipase has been deleted, *Bacillus subtilis, Saccharomyces cerevisiae* and related species, *Hansenula polymorpha* and related species, and varieties of the genus *Aspergillus*. The parent organisms from which such artifically modified microorganisms are produced may be referred to as host cells or organisms. These host cells reflect a broad range of different micoorganisms, and other microorganisms not described in detail in the examples can also be used as host cells.

The use of the invention especially in regard to the production of bacterial lipases, mutated or not, in heterologous host microorganisms can circumvent problems related to the use of original hosts for large scale production, e.g. handling and containment problems in the cases where such organisms are considered potential plant pathogens.

In mutant lipases according to the invention, the mutation can for example be selected from (a) introduction (e.g. by insertion or substitution) or one or more proline residues at an amino acid chain location otherwise vulnerable to proteolytic attack;

(b) an increase of the net positive charge of the lipase molecule (e.g. by insertion of positively-charged amino acid residues or by substitution of neutral or negatively-charged amino acid residues);

examples include the deletion of negatively-charged residues (e.g. aspartate or glutamate), or their substitution by neutral residues (e.g. serine, glycine, proline), or the substitution of neutral or negative residues by positively-charged aminoacid residues (e.g. arginine or lysine) or the insertion of positively-charged residues; for example mutations D157R, D55A and I110K relative to the sequence of *Ps. glumae* lipase or a homologue thereof, increasing the net positive charge and pI;

(c) introduction (e.g. by insertion or substitution) of one or a combination of amino acid residues into the lipase, said residues being capable of becoming glycosylated when the lipase is synthesised in the selected host cell, which can improve the stability of the glycolysated lipase against proteolytic attack;

also contemplated are aminoacid sequence modification(s) chosen to introduce (or, if desired, to remove) aminoacids capable of becoming glycosylation sites; for example mutations D157T and/or *155aG relative to the sequence of *Ps. glumae* lipase or a homologue thereof;

(d) deletion or replacement of methionine to improve the stability of the enzyme against oxidizing agents.

Aminoacid sequence modification(s) can be chosen to improve stability of lipase against attack by subtilisin protease by modifying the sequence at a subtilisin cleavage site, for example by deleting one two or preferably three aminoacid residues forming such a site, or by introducing by insertion or substitution at least one basic (positively-charged) amino-acid residue, or at least one proline residue, at or near the cleavage site in the aminoacid sequence of said lipase as it existed before mutation.

Figure 3A:
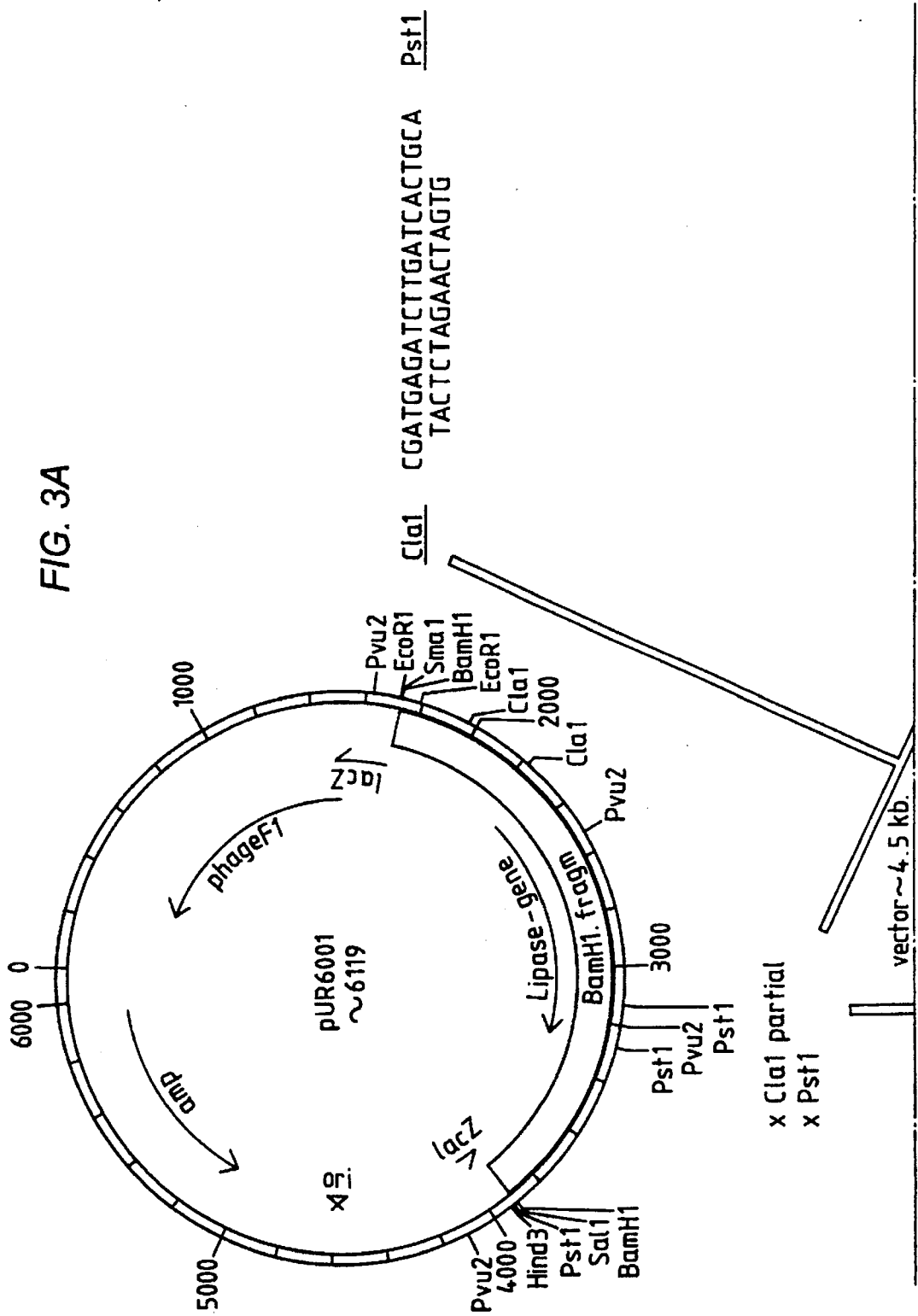
Figures 1, 3A:
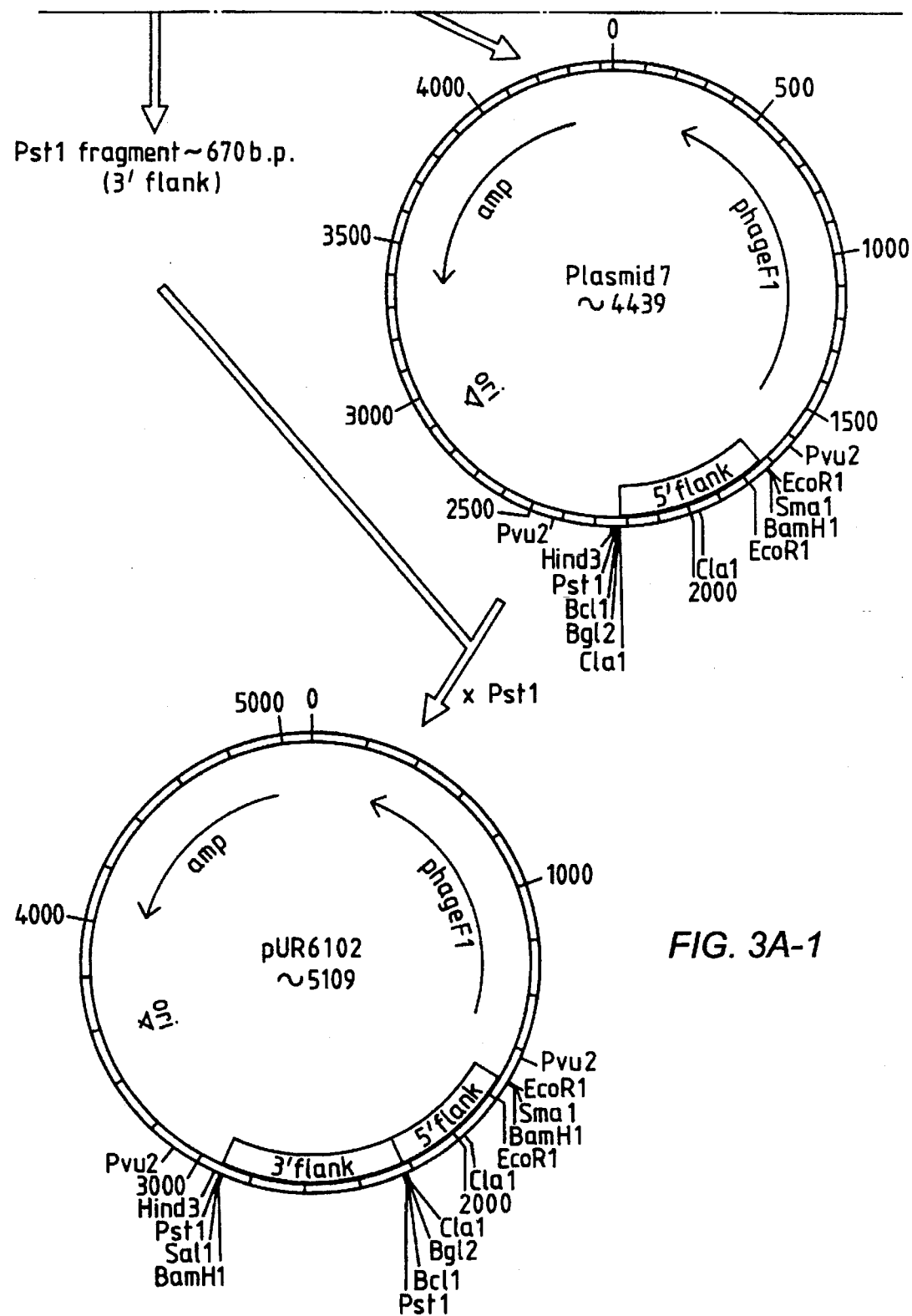
Figures 2, 3A:
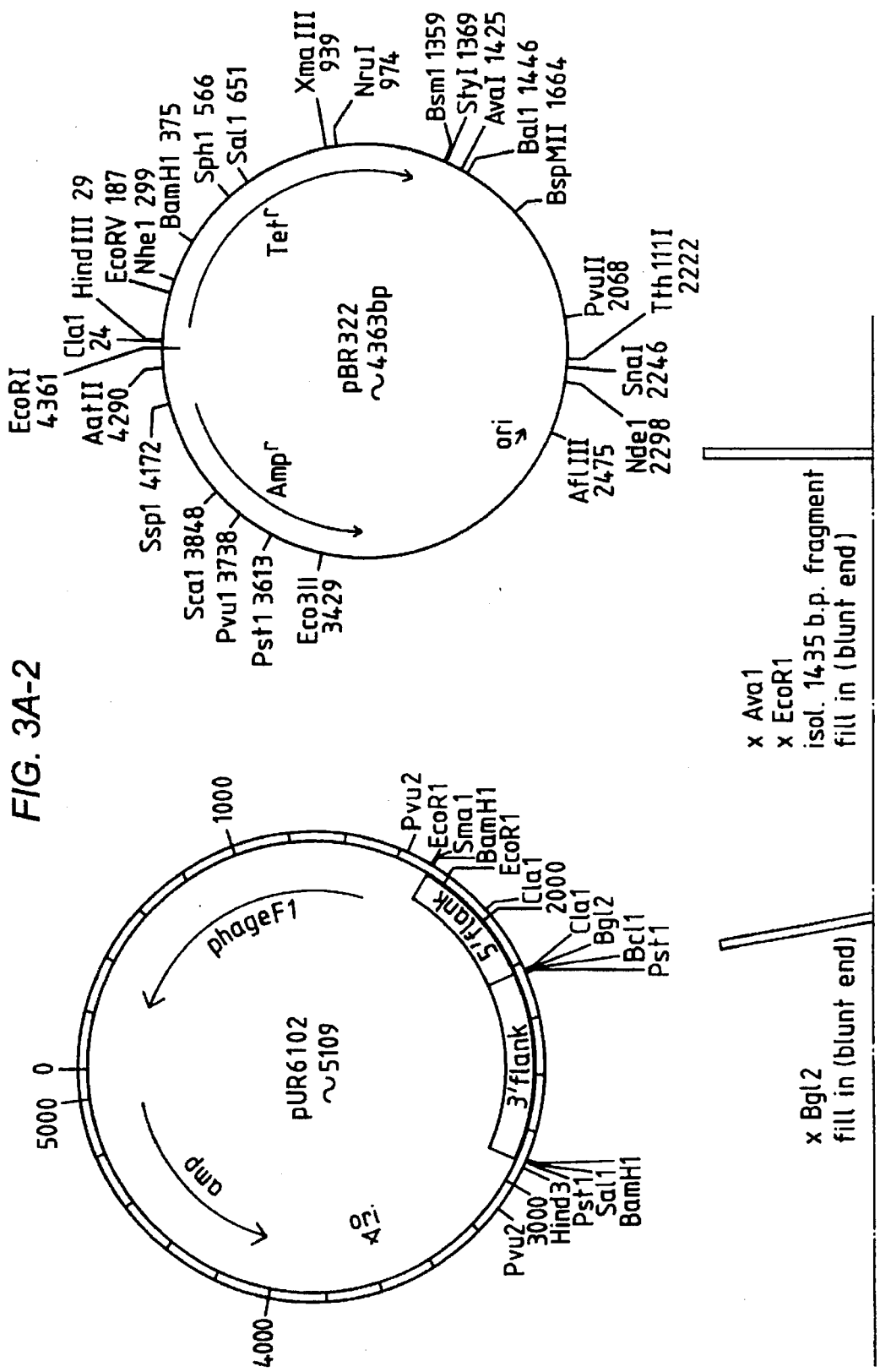

Examples of such mutant lipases according to the invention include those based on the sequence of lipase from *Ps. glumae* or homologues thereof, with for example mutation H154P or *155aG; or on the sequence of lipase from *Ps. cepacia* (e.g. as described in EP 0 331 376 (Amano) especially in FIG. 2, where position 1 in the sequence of the mature enzyme is at position 45 in the Figure) or a homologue of such a sequence, with for example mutation S153P.

More generally, the invention also provides mutant proteins with lipase or other enzyme activity, carrying one or more aminoacid sequence modification(s) chosen to improve stability of of the protein against attack by protease, e.g. by subtilisin protease, by (i) modifying the sequence at a subtilisin cleavage site, i.e. in the sequence within five residues on either side of a bond susceptible in the parent protein to subtilisin cleavage, for example by deletion of one two or preferably three aminoacid residues forming part of such a site as it existed before mutation, or (ii) by introducing insertion or substitution at least one basic amino-acid residue, or at least one proline residue, at such a site, or (iii) modifying the electrostatic potential at such a site by introduction of positively charged aminoacids or removal of negatively charged aminoacids at such a site; e.g. a mutation wherein (a) the aminoacid residue that would become a new N-terminal upon cleavage of the bond susceptible in the parent enzyme to subtilisin cleavage, is replaced by proline; and/or (b) an amino-acid residue two or four positions from such a susceptible bond is replaced by a charged or more polar amino-acid residue.

A mutant lipase or other protein can thus for example carry a mutation at one or more of positions two and four residues from a scissile bond (towards the N-terminus of the lipase) from a bond which in the parent lipase is susceptible to scission by subtilisin protease, to introduce, e.g. by replacement, one or more polar or charged aminoacid residues, e.g. asp, glu, lys, arg, his, gln or asn, to confer improved resistance against proteolysis by subtilisin.

Methods for identifying such cleavage sites prior to their modification are exemplified in Example 14 below.

Another form of aminoacid sequence modification to improve stability of the lipase against inactivation comprises modifying the sequence at a methionine residue by deletion or substitution to remove the methionine residue from the sequence.

Still a further form of stabilisation of a bacterial lipase produced by rDNA technique, especially a lipase that shows immunological cross-reactivity with an antiserum raised against lipase from *Chromobacter viscosum* var *lipolyticum* NRRL B-3673, or against lipase from Alcaligenes PL-679, ATCC 31371 or FERM-P 3783, or against lipase from *Pseudomonas fluorescens* IAM 1057; can be achieved when the lipase (which can be but need not necessarily be of modified i.e. mutated aminoacid sequence) is expressed in an artificially modified heterologous and eukaryotic host microorganism, whereby the lipase is differently glycosylated than the lipase produced by the parent microorganism from which the gene or sequence originated that is expressed in the eukaryotic host.

The host organisms can be prokaryotic, for example a Gram (–) negative bacterium, for example a gram-negative bacterium selected from *E. coli; Ps. aeruginosa; Ps. putida* or *Ps. glumae* (alias *Ps. gladioli*); or a prokaryote selected from the genus Bacillus, Corynebacterium or Staphylococcus, and especially for example belonging to the species *Pseudomonas putida* and expressing a lipase gene derived from *Ps. glumae* (syn *Ps. gladioli*).

Alternatively the host organism can be a eukaryote, for example a yeast of the genus Saccharomyces or the genus Hansenula, or a fungus of the genus Aspergillus.

Examples of usable heterologous host cells for lipase prodcution include *Escherichia coli, Pseudomonas aeruginosa, Ps. putida. Ps. glumae* in which the original lipase gene has been deleted is a further suitable host. The preferred host systems for large scale production are *Bacillus subilis, Saccharomyces cerevisiae* and related species, *Hansenula polymorpha* and related species and members of the genus Aspergillus. Also suitable hosts for large scale production are Gram (–) negative bacteria specially selected and/or modified for efficient secretion of (mutant) lipases. As these host cells reflect a broad range of different microorganisms other microorganisms not described in detail in the examples can be used as well as host cells.

Within the preferred class of lipases the lipase produced by *Pseudomonas glumae* (formerly and more usually called *Pseudomonas gladioli*) is a preferred basis for the processes and products of this invention. Neither the amino acid sequence nor the nucleotide sequence of the gene coding for the preferred lipase was previously known. The present inventors have isolated the gene coding for the preferred lipase of this bacterium as will be illustrated below.

Also according to the invention, the stability of lipases can be improved as follows:

(a) By mutation which changes the surface charge of the enzyme in such a way that the charge of the enzyme in the detergent system is closer to the pH of the detergent system. This is done by changing acid amino acids residues into neutral or basic amino acids without destroying the conformation of the enzyme and without affecting the charge around the active site too much.

b) The lipase amino-acid sequences can be modified by rDNA technique in such a way that loop structure of the lipase protein product are stabilized against physical or chemical denaturation or enzymic cleavage.

Certain loops of the lipase are quite sensitive towards cleavage by proteases also present in the detergent system. A powerful method to improve the resistance of these loops to cleavage is the replacement of an amino acid in the vicinity of the cleavage-site by proline provided this is done without destroying the desired flexibility of these loops. Another way to improve the stability of these loops is to replace by rDNA technique acid amino acid residues in that loop by basic ones, or otherwise increase the net positive charge, thus creating repulsive forces between the lipase and the protease. Some loops can be shortened by deletion of aminoacid residues and corresponding triplets of nucleotides, without affecting the structure of the lipase essentially. Since apolar aminoacids are favoured by subtilisins at positions two and four residues from the scissile bond (towards the N-terminus of the lipase under attack), resistance against proteolysis by subtilisin can also be improved by introduction, e.g. by replacement, of one or more aminoacids at these positions by one or more polar or charged aminoacid residues, e.g. by asp, glu, lys, arg, his, gln or asn.

These changes can for example be carried out by (i) modifying the sequence at a subtilisin cleavage site, i.e. in the sequence within five residues on either side of a bond susceptible in the parent enzyme to subtilisin cleavage, for example by deletion of one two or preferably three aminoacid residues forming part of such a site as it existed before mutation, or (ii) by introducing by insertion or substitution at least one basic amino-acid residue, or at least one proline residue, at such a cleavage site, or (iii) modifying the electrostatic potential at such a site by introduction of positively charged aminoacids or removal of negatively charged aminoacids at such a site.

For example, the aminoacid residue that would become a new N-terminal upon cleavage of the bond susceptible in the parent enzyme to subtilisin cleavage, can be replaced by proline, e.g. when the mutation is based on the sequence of lipase from *Ps. glumae* or a homologue thereof, for example mutation H154P; or on the sequence of lipase from *Ps. cepacia* or a homologue thereof, for example S153P; and/or (ii) an amino-acid residue two of four positions from susceptible bond can be replaced by a charged or more polar amino-acid residue, e.g. when the mutation is based on the sequence of lipase from *Ps. glumae* or a homologue thereof, for example mutation V150D.

(c) The gene coding for *Pseudomonas glumae* lipase contains two sites that can be glycolysated when this gene is transferred into an eukaryotic host. Glycosylation can have a stabilizing effect on the enzyme, particularly if the glycosylation occurs outside the active centre and the lipid binding region of the enzyme. On the other hand glycosylation can interfere with the lipid binding to the lipase.

(d) Methionine residues in lipase enzyme can be oxidatively inactivated quite readily in detergent systems. As only one methionine is present in many of the preferred lipases, deletion or replacement of this methionine by another type of residue is a useful modification relatively easy to perform by rDNA technique.

(e) Besides improving the stability, rDNA techniques have been Used to determine the active and binding site of the lipase and to modify amino acids in or in the near vicinity of these sites either to improve the specific activity of the lipase or the affinity for lipids in soil matrices.

A suitable and presently preferred example of a mutant lipase is based on lipase from *Pseudomonas glumae* with a His 154 Pro (H154P) mutation, which is believed to replace a site vulnerable to protease digestion in one of the loops of the tertiary structure of the lipase with a less vulnerable site.

According to the present invention it is found that modified (mutant) lipases from Pseudomonas or another of the preferred class of lipases, or lipases of modified or unmodified sequence expressed in heterologous producer organisms, e.g. with amino acid sequence modification(s) or changed glycosylation to increase the stability of the enzyme to protease digestion, are of value in detergent and cleaning compositions, especially for example in combination with proteases, e.g. proteases of the subtilisin type.

The invention thus provides, for example, a lipase having an aminoacid sequence substantially homologous with that of a bacterial lipase, e.g. that of *Pseudomonas glumae*, and produced by a heterologous and eukaryotic host microorganism on the basis of rDNA technique to introduce into said host microorganism a gene encoding the corresponding bacterial lipase or a mutant thereof, whereby said lipase is differently glycosylated than the lipase produced by the parent microorganism from which said gene originated.

According to a further aspect of the present invention it is found that modified (mutant) lipases from Pseudomonas or another of the preferred class of lipases with amino acid sequence modification(s) chosen to increase the net positive charge of the lipase and its pI, are also of value in detergent and cleaning compositions, especially for example in combination with proteases, e.g. proteases of the subtilisin type.

Suitable mutations include for example the deletion of negatively charged residues (e.g. aspartate or glutamate) or their substitution by neutral residues (e.g. serine, glycine and proline) or by the substitution of neutral or negative residues by positively charged amino acid residues (e.g. arginine or lysine) or the insertion of positively-charged residues.

Suitable examples of such mutations increasing the net positive charge and pI include D157R, D55A and I110K.

Suitable examples of the introduction (e.g. by insertion or substitution) of a combination of amino acid residues capable of becoming glycosylated in the selected host and thereby improving its stability against proteolytic attact are given by mutations D157T and insertion of G between N155 and T 156. If it is desired to limit over-glycosylation or to remove glycosylation on less desirable positions the potential glycosylation sites of the original lipase can be removed.

The table given below shows mutations carried by certain useful examples of mutant lipases according to the invention, based on the sequence of lipase from *Pseudomonas glumae*.

In the table of mutants given below, and elsewhere in this specification, amino-acids and aminoacid residues in peptide sequences are indicated by one-letter and three-letter abbreviations as follows:

A=Ala=Alanine
V=Val=Valine
L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Ash=Asparagine
Q=Gln=Glutamine
D=Asp=Aspattic Acid
E=Glu=Glutamic Acid
K=Lys=Lysine
R=Arg Arginine
H=His=Histidine In this specification, a mutation present in the aminoacid sequence of a protein, and hence the mutant protein itself, may be described by the position and nature of the mutation in the following abbreviated way: by the identity of an original amino-acid residue affected by the mutation; the site (by sequence number) of the mutation; and by the identity of the amino-acid residue substituted there in place of the original. If there it an insertion of an extra aminoacid into the sequence, its position is indicated by one or more subscript letters attached to the number of the last preceding member of the regular sequence or reference sequence.

For example, a mutant characterised by substitution of valine by proline in position 150 is designated as: Val150Pro or V150P. A (hypothetical) insertion of an additional amino acid residue such as proline after the valine would be indicated as Val150ValPro or V150VP, alternatively as *150aP, with the inserted residue designated as position number 150a. A (hypothetical) deletion of valine in the same position would be indicated by Val150* or V150*. The asterisk stands either for a deletion or for a missing aminoacid residue in the position designated, whether it is reckoned as missing by actual deletion or merely by comparison or homology with another or a reference sequence having a residue in that position.

Multiple mutations are separated by plus signs, e.g. V150P+S152P+H154P designates a mutant protein carrying three mutations by substitution, as indicated for each of the three mentioned positions in the aminoacid sequence. The mutations given in the following table may be combined if desired.

TABLE

Mutant lipases based on *Pseudomonas glumae* lipase sequence:

| Strain (label): | Mutation |
| --- | --- |
| PGL4 | V150A |
| PGL5 | V150S |
| PGL6 | V150D |
| PGL7 | V150K |
| PGL8 | D159E |
| PGL24 | H154P |
| PGL31 | S153P |
| PGL27 | S153R |
| PGL33 | H154R |
| PGL39 | D157R |
| PGL32 | S153G |
| PGL34 | H154G |
| PGL37 | S153P + H154P |
| PGL55 | S152P + H154P |
| PGL56 | V150P + H154P |
| PGL58 | V150P + S152P + H154P |
| PGL36 | S153R + H154R |
| PGL38 | S153G + H154G |
| PGL57 | S151R + H154P |
| PGL35 | S153G + H154P |
| PGL59 | S152* + S153* + H154P |
| PGL40 | S152A + *152aL + *153aG + *154aP (sequence SSH at positions 152–4 becomes ALSGHP, with 3 net insertions) |
| PGL41 | S152A + *152aL + *153aG + *154aP + N155R + T156L + D157P + D159N (sequence SSHNTDQD at positions 152–9 becomes ALSGHPRLPQN with 3 net insertions) |
| PGL42 | N48S |
| PGL43 | N238S |
| PGL44 | *155aG |
| PGL45 | D157T |

TABLE-continued

Mutant lipases based on *Pseudomonas glumae* lipase sequence:

| Strain (label): | Mutation |
|---|---|
| PGL46 | N48S + N238S |
| PGL12 | H15A |
| PGL13 | T109D |
| PGL14 | T110K |
| PGL16 | R8D |
| PGL17 | R8Q |
| PGL18 | R61P |
| PGL19 | K70Q |
| PGL20 | A74S |
| PGL21 | S87A |
| PGL22 | R94D |
| PGL23 | R49Q |
| PGL28 | D55A |
| PGL29 | D56A |
| PGL30 | D263E |
| PGL60 | D121E |
| PGL61 | D287E |
| PGL62 | H285A |
| PGL63 | M254I |

The invention also provides genetic material derived from the introduction of bacterial lipase genes, e.g. the gene from *Ps glumae*, into cloning vectors, and the use of these to transform new host cells and to express lipase genes in the new host cells.

Also provided by the invention are polynucleotides made or modified by rDNA technique, which encode such lipases, vectors containing such polynucleotides, and artificially modified microorganisms containing such polynucleotides and/or such vectors.

The invention also provides corresponding polynucleotides encoding the lipase enzymes, e.g. a polynucleotide having a base sequence that encodes a mature lipase for example of sequence substantially as shown in FIG. 2 or a functional equivalent or a mutant thereof, in which polynucleotide the final translated codon is followed by a stop codon and optionally having nucleotide sequences coding for the presequence of this lipase directly upstream of the nucleotide sequences coding for the mature lipase.

In such a polynucleotide, the lipase-encoding nucleotide sequence derived from the organism of origin can be modified in such a way that at least one codon, and preferably as many codons as possible, are made the subject of 'silent' mutations to form codons encoding equivalent aminoacid residues and being codons preferred by a new host as specified in one of claims 16 to 23, thereby to provide in use within the cells of such host a messenger-RNA for the introduced gene of improved stability.

Upstream of the nucleotide sequences coding for the pro-or mature lipases, there can be located a nucleotide sequence that codes for a signal or secretion sequence suitable for the chosen host.

Thus an embodiment of the invention relates to a rDNA vector into which a nucleotide sequence coding for a (modified) lipase belonging to the preferred class or a precursor thereof has been inserted.

The nucleotide sequence can be derived for example from:

(a) a naturally occuring nucleotide sequence (e.g. that of FIG. 2) encoding the original amino acid sequence of the prelipase produced by *Pseudomonas glumae* (FIG. 2);

(b) chemically synthesized nucleotide sequences consisting of codons that are preferred by the new host (an example of which has been given in FIG. 5) and a nucleotide sequence resulting in stable messenger RNA in the new host, still encoding the original amino acid sequence;

(c) nucleotide sequences encoding lipases that show positive immunological cross reaction against the antibodies raised against the lipase of *Pseudomonas fluorescens* IAM 1057 as described in EP 0 205 208 and EP 0 206 390;

(d) genetically engineered nucleotide sequences derived from one of the nucleotide sequences mentioned in preceding paragraphs a, b or c coding for a lipase with a different amino acid sequence but having superior stability and/or activity in detergent systems.

Vectors able to direct the expression of the nucleotide sequence encoding a lipase gene as described above in one of the preferred hosts preferably comprise the following components:

(a) Double-stranded (ds) DNA coding for mature lipase or prelipase (e.g. FIG. 2 or a mutant sequnce based thereon) or a corresponding prelipase in which part of the presequence has been removed directly down stream of a secretion signal (preferred for the selected host cell). In cases where the part of the gene that should be translated does not start with the Codon ATG, an ATG codon should be placed in front. The translated part of the gene should always end with an appropriate stop codon.

(b) An expression regulon (suitable for the selected host organism) situated upstream of the plus strand of the ds DNA encoding the lipase (component (a)).

(c) A terminator sequence (suitable for the selected host organism) situated down stream of the plus strand of the ds DNA encoding the lipase (component (a).

(d) Nucleotide sequences which facilitates integration, of the ds DNA into the genome of the selected host or an origin of replication suitable for the selected host, and optionally a (auxotrophic) selection marker;

(e) optionally a ds DNA sequence encoding proteins involved in the maturation and/or secretion of one of the precursor forms of the lipase in the host selected, e.g. an origin of replication suitable for the chosen host.

Such a vector can also carry, upstream and/or downstream of the polynucleotide as earlier defined, further sequences facilitative of functional expression of the lipase. The auxotrophic marker can consist of a coding region of the auxotrophic marker and a defective promotor region.

The invention also provides a process for producing a mutant lipase, which comprises the steps of fermentatively cultivating an artificially modified microorganism containing a gene made by rDNA technique which is either of heterologous origin or carries at least one mutation affecting the aminoacid sequence of the lipase thereby to confer upon the lipase improved stability against attack by protease and/or oxidising agents and/or increased activity by comparison with the corresponding parent enzyme, making a preparation of the lipase by separating the lipase produced by the microorganism either from the fermentation broth, or by separating the cells of the microorganism from the fermentation broth, disintegrating the separated cells and concentrating or part purifying the lipase either from said broth or from said cells by physical or chemical concentration or purification methods.

Accordingly, in certain aspects the invention provides artificially modified microorganisms containing a lipase gene and able to produce lipase derived originally from one of the organisms mentioned above or a modified form of such lipase by use of rDNA techniques and fermentative processes for lipase production based on such artificially modified microorganisms.

In an artificially modified microorganism, a gene (if originally present) encoding the native lipase is preferably removed, e.g. replaced by another structural gene.

Another embodiment of this invention is the fermentative production of one of the various forms of lipases described above or related hosts. Such a fermentation can either be a normal batch fermentation, fed-batch fermentation or continuous fermentation. The selection of a process to be used depends on the host strain and the preferred down stream processing method (known per se).

Preferably conditions are chosen such that the lipase is secreted by the microorganism into the fermentation broth, the lipase being recovered from the broth after removal of the cells either by filtration or centrifugation. Optionally the lipase can then be concentrated and purified to a certain extent by ethanol extraction.

The fermentation processes in themselves apart from the special nature of the microorganisms can be based on known fermentation techniques and commonly used fermentation and down stream processing equipment.

The present invention includes also a process for encapsulation of the various lipases in order to reduce allergenic reactions that may be caused by lipase during manufacturing. Moreover the way the lipase is encapsulated can contribute to the stability and the effectiveness of the lipase in the detergent system.

Also provided by the invention is a method for the production of a modified microorganism capable of producing a bacterial lipase by rDNA techniques, characterized in that the gene coding for the bacterial that is introduced into the microorganism is fused at its 5'-end to a gene fragment encoding a (modified) pre-sequence functional as a signal- or secretion-sequence for the host organism.

The host organism can be given, or can be one that contains, a modified gene substantially corresponding to a prepro-lipase sequence e.g. as shown in FIG. 2 or a functional equivalent thereof.

In particular embodiments of the invention the gene of bacterial origin is introduced with an artificial pro-sequence into a eukaryotic organism, e.g. yeast or fungus.

A preferred class of lipases in connection with this invention originates from Gram (−) negative bacteria, and includes e.g. lipase enzymes of the groups defined in EP 0 205 208 and 0 206 390 (Unilever), including lipases immunologically related to those from strains of *Ps. fluorescens, Ps. gladioli* and Chromobacter.

There are many publications showing that Gram (−) negative bacteria are poor producers of extracellular enzymes. Therefore at present no Gram (−) negative bacteria are used in fermentation processes for the production of bulk enzymes such as enzymes for detergent systems, and we have surprisingly found that such bacteria can be useful host cells for the production of lipases in accordance with this invention.

The invention further provides recombinant DNA vectors carrying nucleotide sequences coding for (modified) lipases belonging to the preferred class or precursors thereof.

The invention further provides fermentative production of the various forms of lipases described above, e.g. in a host different from the organism from which the enzyme originates and into which the gene corresponding to the enzyme has been introduced by rDNA technique.

Such a fermentation process can either be a normal batch fermentation, a fed-batch fermentation or a continuous fermentation. The selection of the process to be used depends on the host strain and the preferred process for down stream processing.

It is preferred that the host microorganims be selected so that the lipase is secreted into the fermentation broth by the microorganism, enabling the lipase to be recovered from the broth after removal of the cells either by filtration or centrifugation.

Optionally the lipase can subsequently be concentrated and purified to a certain extent e.g. by ethanol extraction.

In certain embodiments the present invention also provides encapsulated compositions containing lipase produced as described herein. Encapsulation in manner known per se can reduce allergenic reaction that may be caused by lipase during manufacturing and handling.

The present invention also provides, in further embodiments, combinations of the lipases and other constituents used in detergent systems, including additives for detergent compositions and fully-formulated detergent and cleaning compositions, e.g. of the kinds known per se and described for example in EP 0 258 068.

The present invention also provides a number of combinations of lipases and other constituents used in detergent systems, to provide useful advantage in the removal of fatty material and material adsorbed to the fatty material in soil on textile.

The other components of such detergent compositions can be of any of many known kinds, for example as described in GB 1 372 034 (Unilever), U.S. Pat. No. 3,950,277, U.S. Pat. No. 4,011,169/NL 74 08763, EP 0 179 533 (Procter & Gamble), EP 0 205 208 and 0 206 390 (Unilever), JA 63-078000 (1988) (Lion Corp/K. Mukoyama et al), and Research Disclosure 29056 of June 1988, together with each of the several specifications mentioned therein, all of which are hereby incorporated herein by reference.

In several useful embodiments the detergent compositions can be formulated as follows:

a) A detergent composition formulated as a detergent powder containing phosphate builder, anionic surfactant, nonionic surfactant, acrylic or equivalent polymer, perborate bleach precursor, amino-containing bleach activator, silicate or other structurant, alkali to adjust to desired pH in use, and neutral inorganic salt.

b) A detergent composition formulated as a detergent powder containing zeolite builder, anionic surfactant, nonionic surfactant, acrylic or equivalent polymer, perborate bleach precursor, amino containing bleach activator, silicate or other structurant, alkali to adjust to desired pH in use, and neutral inorganic salt.

c) A detergent composition formulated as an aqueous detergent liquid comprising anionic surfactant, nonionic surfactant, humectant, organic-acid, caustic alkali, with a pH adjusted to a value between 9 and 10.

d) A detergent composition formulated as a nonaqueous detergent liquid comprising a liquid nonionic surfactant consisting essentially of linear alkoxylated primary alcohol, triacetin, sodium triphosphate, caustic alkali, perborate monohydrate bleach precursor, and tertiary amine bleach activator, with a pH adjusted to a value between about 9 and 10.

e) A detergent composition formulated as a detergent powder in the form of a granulate having a bulk density of at least 550 g/l, e.g. at least 600 g/l, containing anionic and nonionic surfactants, e.g. anionic surfactant and a mixture of nonionic surfactants with respective alkoxylation degrees about 7 and about 3, low or substantially zero neutral inorganic salt, phosphate builder, perborate bleach precursor, tertiary amine bleach activator, sodium silicate, and minors and moisture.

f) A detergent composition formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, zeolite builder, perborate bleach precursor, tertiary amine bleach activator, sodium silicate, and minors and moisture.

g) A detergent composition formulated as a detergent powder containing anionic surfactant, nonionic surfactant, acrylic polymer, fatty acid soap, sodium carbonate, sodium sulphate, clay particles with or without amines, perborate bleach precursor, tertiary amine bleach activator, sodium silicate, and minors and moisture.

h) A detergent composition formulated as a detergent (soap) bar containing soap based on pan-saponified mixture of tallow and coconut oil, neutralised with orthophosphoric acid, mixed with protease, also mixed with sodium formate, borax, propylene glycol and sodium sulphate, and then plodded on a soap production line.

j) An enzymatic detergent composition formulated to give a wash liquor pH of 9 or less when used at a rate corresponding to 0.4–0.8 g/l surfactant.

k) An enzymatic detergent composition formulated to give a wash liquor pH of 8.5 or more when used at a rate corresponding to 0.4–0.8 g/l surfactant.

l) An enzymatic detergent composition formulated to give a wash liquor ionic strength of 0.03 or less, e.g. 0.02 or less, when used at a rate corresponding to 0.4–0.8 g/l surfactant m) An enzymatic detergent composition formulated to give a wash liquor ionic strength of 0.01 or more, e.g. 0.02 or more, when used at a rate corresponding to 0.4–0.8 g/l surfactant.

The lipase can usefully be added in the form of a granular composition, (alternatively a solution or a slurry), of lipolytic enzyme with carrier material (e.g. in EP 0 258 068 and Savinase and Lipolase products of Novo).

The added amount of lipase can be chosen within wide limits, for example 50 to 30,000 LU/g per gram of the surfactant system or of the detergent composition, e.g. often at least 100 LU/g, very usefully at least 500 LU/g, sometimes preferably above 1000, above 2000 LU/g or above 4000 LU/g or more, thus very often within the range 50–4000 LU/g and possibly within the range 200–1000 LU/g. In this specification lipase units are defined as they are in EP 0 258 068 (Novo).

Similar considerations apply mutatis mutandis in the case of other enzymes, which may also be present. Without limitation: Amylase can for example be used when present in an amount in the range about 1 to about 100 MU (maltose units) per gram of detergent composition, (or 0.014–1.4, e.g. 0.07–0.7, KNU/g (Novo units)). Cellulase can for example be used when present in an amount in the range about 0.3 to about 35 CEVU units per gram of the detergent composition.

The protease of the compositions can for example be used in an amount ranging from about the order of 0.0002 to about the order of 0.05 Anson units per gram of the detergent composition. Expressed in other units, the protease can also be included in the compositions in amounts of the order of from about 1 to 100 GU/mg detergent formulation. Preferably, the amount ranges from 2 to 50 and particularly preferably from 5 to 20 GU/mg.

A GU is a Glycine Unit, defined as the proteolytic enzyme activity which, under standard conditions, during a 15-minute-incubation at 40 deg C., with N-acetyl casein as substrate, produces an amount of NH2-group equivalent to 1 micromole of glycine.

The detergent compositions may furthermore include the following usual detergent ingredients in the usual amounts. They may be built or unbuilt, and may be of the zero-P type (i.e. not containing any phosphorus-containing builders). Thus the composition may contain in aggregate for example from 1–50%, e.g. at least about 5% and often up to about 35–40% by weight, of one or more organic and/or inorganic builders. Typical examples of such builders include those already mentioned above, and more broadly include alkali metal ortho, pyro, and tri-polyphosphates, alkali metal carbonates, either alone or in admixture with calcite, alkali metal citrates, alkali metal nitrilo-triacetates, carboxymethyloxysuccinates, zeolites, polyacetalcarboxylates and so on.

Furthermore, the detergent compositions may contain from 1–35% of a bleaching agent or a bleach precursor or a system comprising bleaching agent and/or precursor with activator therefor. Further optional ingredients are lather boosters, foam depressors, anticorrosion agents, soil-suspending agents, sequestering agents, anti-soil redeposition agents, perfumes, dyes, stabilising agents for the enzymes and so on.

The compositions can be used for the washing of textile materials, especially but without limitation cotton and polyester-based textiles and mixtures thereof. Especially suitable are for example washing processes carried out at temperatures of about 60–65 deg C. or lower, e.g. about 30–35 deg C. or lower. It can be very suitable to use the compositions at a rate sufficient to provide about e.g. 0.4–0.8 g/l surfactant in the wash liquor, although it is of course possible to use lesser or greater concentrations if desired. Without limitation it can for example be stated that a use-rate from about 3 g/l and up to about 6 g/l of the detergent formulation is suitable for use in the case when the formulations are as in the detergent composition Examples below, D1–D14.

Advantage may be gained in such detergent compositions, where protease is present together with the lipase, by selecting such protease from those having pI lower than 10. EP 0 271 154 (Unilever) describes a number of such proteases. Proteases for use together with lipases can in certain circumstances include subtilisin of for example BPN' type or of many of the types of subtilisin disclosed in the literature, some of which have already been proposed for detergents use, e.g. mutant lipases as described in for example EP 0 130 756 or European Application 87303761 (Genentech); U.S. Pat. No. 4,760,025 (Genencor); EP 0 214 435 (Henkel); WO 87/04661 (Amgen); WO 87/05050 (Genex); Thomas et al in Nature (1986/5) p 316, pp 375–376 and in J Mol Biol (1987) 193, pp 803–813; Russel et al in Nature (1987) 328, pp 496–500, and others.

The invention is further and non-limitatively illustrated in the following Examples, which refer to the accompanying drawings, charts and diagrams, and in which Examples 1–13, illustrating various stages in the practice of the invention, give details of rDNA techniques and the production of lipase enzymes according to examples of the invention, and further examples D1 to D14 give relevant detergent formulations in which the lipases can be used, given for illustration and not limitation.

EXAMPLE 1

Isolation and characterization of the gene encoding (pre)-lipase of P. glumae.

EXAMPLE 2

Construction of a P. glumae strains from which the lipase gene has been deleted.

EXAMPLE 3

Production of synthetic genes encoding *P. glumae* (wild type) lipase.

EXAMPLE 4

Introduction of the synthetic gene encoding wild type lipase in *P. glumae* lipase-negative strains.

EXAMPLE 5

Production of mutant genes and their introduction in the lipase negative *P. glumae* strains.

EXAMPLE 6

Expression of synthetic lipase genes in *B. subtilis*.

EXAMPLE 7

Expression of synthetic lipase genes in *S. cerevisiae*.

EXAMPLE 8

Expression of synthetic lipase genes in *H. polymorpha*.

EXAMPLE 9

Expression of synthetic lipase genes in Aspergillus.

EXAMPLE 10

Expression of lipase in gram negative bacteria, other than *P. glumae*.

EXAMPLE 11

Determination of the improved proteolytic resistance of modified lipase.

EXAMPLE 12

Improvement of the resistance of *P. glumae* lipase against oxidative degradation by replacement of its single methionine.

EXAMPLE 13

Determination of site of cleavage in lipase by subtilisin.

In the description of the examples of carrying out the several parts of the present invention, literature references are given by bracketed numbers. The prefix 'ḿ' as in ḿg stands for 'micro'.

The following strains referred to herein have been deposited at the Centraalbureau voor Schimmelcultures at Baarn, Netherlands, under the accession numbers following:

*Pseudomonas glumae* strain PG1 as CBS 322.89
*Pseudomonas glumae* strain PG3 as CBS 323.89
*Pseudomonas glumae* strain PGT89 as CBS 262.90

The following features of the practice of the invention as illustrated in the Examples are further illustrated in the accompanying drawings, listed with their respective general topics as follows:

FIG. 1: Plasmid construction from Example 1

FIG. 2: Complete nucleotide sequence (1074 bp) and aminoacid sequence of the lipase gene from *Pseudomonas glumae,* with amino terminal encoded by nucleotides 118 et seq.

FIGS. 3*a–b:* Plasmid construction (and alternates) from Example 2

FIG. 4: Plasmid construction from Example 2

FIG. 5: Synthetic lipase gene from Example 3

FIG. 6: A–C: Gene cassette from Example 3

FIGS. 7*a–b:* Plasmid constructions from Example 4

FIG. 8: Oligomers for mutant gene from Example 4

FIG. 9: Plasmid construction from Example 6

FIG. 10: Plasmid construction from Example 6

FIG. 11: Plasmid construction from Example 6

FIGS. 12*a–b:* Nucleotide sequences from Example 6

FIG. 13: Plasmid construction from Example 6

FIG. 14: Plasmid construction from Example 6

FIG. 15*a*: Plasmid construction and results from Example 7

FIGS. 15*b–c:* Plasmid constructions from Example 7

FIGS. 16,16*a–h:* Plasmid constructions from Example 8

FIGS. 17,17*a–f*: Plasmid constructions from Example 9

FIGS. 18–20: plasmid construction from Example 10

FIGS. 23–26: Illustration of results from Example 11

EXAMPLE 1

Isolation and characterization of the gene encoding (pre)-lipase of *P. glumae.*

Isolation of *P. glumae* chromosomal DNA.

Cells of a 15 ml overnight culture in LB medium were collected by centrifugation (Sorvall HB4 rotor, 10 krpm for 10 min). The cell pellet was stored at −20 deg C. overnight. After thawing the cell were resuspended in 10 ml SSC (0.15M NaCl, 0.015M Na-Citrate) containing 2 mg/ml lysozyme. After incubation for 30 min at 37 deg C., 0.5 ml of 10% SDS was added, followed by an incubation at 70 deg C. for 10 min. After cooling to 45 deg C., 1 ml proteinase K (2 mg/ml Tris-HCl pH 7.0, preincubated for 30 min at 45 deg C.) was added and the mixture was incubated at 45 deg C. for another 30 min. Next, 3.2 ml 5M NaClO4 was added, followed by two extractions with 15 ml CHCl3/iso-C5H11OH (24:1), each of which was followed by a centrifugation step (Sorvall HS4, 5 krpm/10 min). The DNA was precipitated from the supernatant by adding 10 ml ethanol. After a wash in 75% ethanol the, DNA pellet was resuspended in 2 ml H2O.

Preparation of a gene bank.

A DNA preparation of *P. glumae* was partially digested with the restriction enzyme Sau3A, as described by Maniatis (1). The cosmid vector c2RB (2) was digested to completion with SmaI and BamHI, both enzymes having one recognition site in the cosmid. Excess vector fragments were ligated, using T4 DNA ligase (in 50 mM Tris-HCl pH 7.5, 10 mM dithiotreitol (DTT), 10 mM MgCl2 and 0.5 mM rATP), with DNA fragments from *P. glumae.* The recombinant DNA thus obtained was packaged in phage particles as described by Hohn (3). The complete phage particles obtained this way were used to transform *E. coli* 1046 (met, gal, lac, hsdR, phx, supE, hsdM, recA) by transfection. 5 ml fresh LB medium containing 0.4% maltose, was inoculated with 0.5 ml of a overnight culture of *E. coli* 1046 and incubated for 6 h. at 37 deg C. under continuous shaking. Before infection with phage particles, MgCl2 and CaCl2 were added to a final concentration of 10 mM. In a typical experiment 50 ml phage particles were mixed with 50 ml of cells and the mixture was incubated at 37 deg C. for 15 min: 100 ml LB medium was added and incubation at 37 deg C. continued for 30 min. The cells were plated directly an LB-agar plates containing 75 mg/ml ampicillin (Brocacef). After overnight growth at 37 deg C. ca. 300 colonies could be counted Oligonucleotide synthesis.

As probes for the lipase encoding DNA fragment, we used oligonucleotides based on the sequences of the 24 N-terminal amino acids (see below), determined by Edman degradation, using an Applied Biosystems Gas Phase Protein Sequencer.

Based on the established amino acid sequence, all the possible nucleotide sequences encoding the amino acid sequence were derived. Deoxy-oligonucleotides containing all or part of the possible nucleotide sequences (so called mixed-probes) were synthesized on a DNA synthesizer (Applied Biosystems 380 A) using the Phospho-amidit technique (4). Oligonucleotides were purified on 16% or 20% polyacrylamide gels (1).

Radiolabeled oligonucleotide probes.

Usually, 0.1–0.3 mg of the purified oligonucleotide was labelled by incubation for 30 minutes at 37 deg C. in 50 mM Tris-HCl pH 7.5, 10 mM MgCl2, 0.1 mM EDTA, 10 mM DTT, 70 mCi gamma-32P-ATP (3000 Ci/mmol, Amersham) and 10 units T4 polynucleotide kinase (Amersham) in a final volume of 15 ml. The reaction was terminated with 10 ml 0.5M EDTA pH 8.0 and passed through a Sephadex G25 column of 2.5 ml (disposable syringe) equilibrated with TE buffer (10 mM Tris-HCl pH 8.0 and 1 mM EDTA). Fractions of 250 ml were collected, from which the first two radioactive fractions, usually fractions 4 and 5, were pooled and used for hybridization.

Screening of the gene bank.

From several packaging and transfection experiments, performed as described above, a total of ca 1000 separate colonies were obtained. These colonies were transferred to ELISA plate (Greiner, F-form) containing 150 ml LB-medium (100 mg ampicillin/ml)/well. After overnight growth at 37 deg C. duplicates were made using a home-made template, consisting of 68 pins, arranged to fit in the microtiter wells. To the wells of the masterplates 50 microliter 50% glycerol was added, and after careful mixing with the aid of the template, these plates were stored at −80 deg C. The duplicates were used to transfer the gene bank to nitro cellulose filters (MilliPore, type HATF, 0.45 mm, α14 cm). To this end the cellulose filters were prewetted by laying them on LB-agar plates with 100 mg/ml ampicillin. After transfer of the bacteria with the aid of the template, colonies were grown overnight at 37 deg C.

The colonies on the filters were lysed by placing them on a stack of Whattman 3 MM paper, saturated with 0.5M NaOH, 1.5M NaCl for 15 min. After removal of excess liquid by placing the filters on dry paper, they were neutralised by placing them on a stack of 3 MM paper, saturated with 1M Tris-HCl pH 7.0, 1.5 mM NaCl for 2–3 min. Finally the filters were dunked into 10×SSC (1.5M NaCl, 0.15M Na-citrate) for 30 sec, air dried and baked at 80 deg C. under vacuum for 2 hours. Prior to (pre)hybridization the filters are washed extensively in 3×SSC, 0.1% SDS at 65 deg C. for 16–24 h with several changes of buffer. The washing was stopped when the colonies were no longer visible.

Pre-hybridization of the filters was performed in 5×SSC, 5×Denhardts (10×denhardts=0.2% ficoll, 0.2% polyvinyl-pyrrolidone, 0.2% bovine serum albumin), 0.1% SDS, 50 mM sodium phosphate pH 7.5, 1% glycine, 100 mg/ml calfthymus DNA (sheared and heat denatured), 500 microg/ml tRNA and 50% deionized formamide for 2 hours at 37 deg C.

Hybridization with a radio-active labelled (see above) mixed probe (vis02, 32 nucleotides) was performed in 5×SSC, 1×Denhardts, 0.1% SDS, 20 mM sodium phosphate pH 7.5, 100 mg/ml calfthymus DNA, 500 mg/ml tRNA and 50% deionized formamide, for 16 h. at 39 deg C. After the hybridization, the filters are washed: 3×15 min with 6×SSC at room tmperature, 1×15 min 2×SSC, 0.1% SDS and subsequently at a room temperature dependent on the properties of the oligonucleotide probe. For vis02 washing was extended for 15 min at 37 deg C. in prewarmed 0.1 SSC 0.1% SDS. Upon screening the gene bank as described above, several cosmid clones were isolated. Clone 5G3 (hereinafter called pUR6000) was chosen for further investigations.

Sequencing of the lipase gene.

DNA fragments resulting from digestion of pUR6000 with BamHI were ligated in plasmid pEMBL9 (5) which was also cleaved with BamHI and the obtained recombinant DNA was used to transform E. coli JM101 (6), with the CaCl2 procedure and plated on LB-agar plates supplemented with X-gal (=5-bromo-4-chloro-3-indolyl-beta-D-galactopyranoside) and IPTG (isopropyl-thiogalactoside) (1).

68 white colonies were transferred to microtiter plates and subjected to the same screening procedure as described for the cosmid bank. Several positive clones could be isolated. A representative plasmid isolated of one of these colonies is depicted in FIG. 1 and is referred to as pUR6002. Upon digesting this plasmid with EcoRI, two fragments were found on gel respectively ~4.1 kb and ~2.1 kb in length. Another plasmid, pUR6001, contained the BamHI fragment in the opposit orientation. After digestion with EcoRI, this plasmid resulted in fragments of ~6.1 kb and ~70 bp.

In essentially the same way pUR6006 was constructed. In this case pUR6000 was digested with EcoRI after which the fragments were ligated in the EcoRI site of plasmid pLAFRI (6a). After screening the transformants, a positive clone was selected, containing a EcoRI fragment of ~6 kb, designated pUR6006 (FIG. 1).

The purified DNA of pUR6001 and pUR6002 was used for the establishment of the nucleotide sequence by the Sanger dideoxy chain termination procedure (7) with the modifications as described by Biggin et al. (8), using alpha-35S-dATP (2000 Ci/mmol) and Klenow enzyme (Amersham), ddNTP's (Pharmacia-PL Biochemicals) and dNTP's (Boehringer). We also used the Sequenase kit (United States Biochemical Corporation), with substitution of the dGTP for 7-deaza-dGTP. The sequencing reaction products were separated on a denaturing polyacrylamide gel with a buffer gradient as described by Biggin et al. (8).

The complete nucleotide sequence (1074bp) of the P. glumae lipase (hereafter also called: glumae lipase) gene is given in FIG. 2.

The nucleotide sequence shows an open reading frame encoding 358 amino acid residues followed by a stop codon.

The deduced amino acid sequence is shown in the IUPAC one-letter notation below the nucleotide sequence in FIG. 2.

The NH2-terminal amino acid sequence of the lipase enzyme as purified from the P. glumae culture broth has been identified as ADTYAATRYPVILVHGLAGTDK. This amino acid sequence is encoded by nucleotides 118–183 (FIG. 2). Firstly from these findings it can be concluded that the mature lipase enzyme is composed of 319 amino acid residues, and has a calculated molecular weight of 33,092 dalton.

Secondly, the enzyme is synthesized as a precursor, with a 39 amino acid residue, N-terminal extension (numbered −39 to −1 in FIG. 2).

From the scientific literature it is well known that most excreted proteins are produced intracellular as precursor enzymes (9). Most commonly these enzymes have a N-terminal elongation, the 'so called leader peptide or signal sequence. This peptide is involved in the initial interaction with the bacterial membrane.

General features of the signal sequence as it is found in gram negative bacteria are:

1. an amino-terminal region containing (on average) 2 positively charged amino acid residues;
2. a hydrophobic sequence of 12 to 15 residues;

3. a cleavage site region, ending with serine, alanine or glycine
4. the total length is approximately 23 amino acids.

Surprisingly, the lipase signal sequence comprises 39 amino acids which is rather long. Furthermore, it contains four positively charged amino acids at the N-terminus. For gram negative bacteria, this seems to be an exceptional type of signal sequence. Isolation of genes from other organisms, encoding related lipases.

As mentioned earlier, the *P. glumae* lipase belongs to a group of immunologically related lipases. From this it can be expected that these enzymes, although produced by different organisms, contain stretches of highly conservative amino acid sequences. As a consequence there has to be certain degree of homology in the DNA-sequence. Having the *P. glumae* lipase gene at our disposal, it is easy to isolate related lipase genes from other organisms.

This can be done in essentially the same way as described above. From the organism of interest a gene bank (for example in a cosmid or phage Lambda) is made. This genome bank can be screened using (parts of) the ~2.2 kb BamHI fragment (described above) as a probe. Colonies giving a positive signal, can be isolated and characterised in more detail.

REFERENCES

1. Maniatis, T. et al. Molecular cloning; Cold Spring Harbor Laboratory 1982, ISBN 8-87969-136-0.
2. Bates, P. F. and Swift, R. A. (1983) Gene, 26, 137–146.
3. Hohn, B. (1979) Methods in Enzymology, Vol 68, Academic Press, New York, pp 299–309.
4. Barone, A. D. et al., (1984) Nucleic Acid Research, Vol 12, pp 4051–4061.
5. Dente, L. et al., (1983) Nucleic Acid Research, Vol 11, pp 1645–1655.
6. Messing, J., (1983) Methods in Enzymology, Vol 101 Academic press, New York.
6a. Friedman et al, Gene 18 (1982) 289–296.
7. Sanger, F., Nicklen, S., and Couilson, A. R. (1977), Proc. Natl. Acad. Sci. USA, 74, 5463–5467.
8. Biggin, M. D. et al., (1983), Proc. Natl. Acad. Sci. USA, 80, 3963–3965.
9. von Heijne, G., and Abrahmsen, L. (1989), FEBS Letters, 244, 439–446.

EXAMPLE 2

Construction of the lipase negative *P. glumae* strains PG2 and PG3.

The construction of PG2, from which the lipase gene has been deleted; and PG3, in which the lipase gene has been replaced with a tetracycline resistance (Tc-res) gene, comprises three main steps.

A—construction of pUR6106 and pUR6107 (in *E. coli*), starting from pUR6001 (see example 1):

pUR6001 contains a BamHI fragment from the *P. glumae* chromosome of ~2.2kb. The lipase gene (1074 basepairs) situated on this fragment, has a 5'- and a 3'-flanking sequence of ~480 and ~660 basepairs, respectively.

Subsequent construction steps were:

a. partial digestion of pUR6001 (isolated from *E. coli* KA816 (=GM48, ref 11a) (dam-3, dcm-6, thr, leu, thi, LacY, galK2, galT22, ara-14, tonA31, tsx-78, supE44) with ClaI, to obtain linearized plasmids b. phenol extraction and ethanol precipitation (1) of the DNA, followed by digestion with PstI c. isolation of a 4.5 kb Plasmid DNA fragment (having ClaI and a PstI sticky ends), and a PstI fragment of ~670 bp from agarose gel after gel electrophoresis followed by electro-elution in dialysis bags (1)

d. the obtained plasmid DNA fragment with a ClaI and a PstI sticky end was ligated with a synthetic linker fragment (shown below), with a ClaI and a PstI sticky end:

| ClaI | CGATGAGATCTTGATCACTGCA | PstI |
|------|------------------------|------|
|      | TACTCTAGAACTAGTG        |      |

This synthetic fragment contains a recognition site for the restriction enzymes BclI and BglII.

After transformation of the ligation mixture to *E. coli* SA101 (is JM101 with recA, hsdR), selection on LB-Ap (100 microgram ampicillin/ml) agar plates, and screening of the plasmids from the obtained transformants by restriction enzyme analysis, a plasmid of the correct structure (referred to as No 7) was selected for the next construction step. Upon digesting this correct plasmid with BamHI and HindIII a vector fragment of ~4kb and an insert fragment of ~500 bp were found.

e. the plasmid construct (No 7) obtained as described in d. was digested with PstI, and ligated together with the ~670 bp PstI fragment isolated as described in c.

f. transformation of the ligation mixture to *E. coli* SA101, selection on LB-Ap (100 mg ampicillin/ml) agar plates, and screening of the plasmids from the obtained transformants. Since the PstI fragment can have two different orientations this had to be analysed by means of restriction enzyme analysis. In the construct we were looking for, the orientation should be thus that digestion with BamHI results in a vector fragment of ~4 kb and an insert-fragment of ~1.2 kb.

A less preferred route to this result is as follows:

a'. partial digestion of pUR6002 (ex *E. coli* KA816) with ClaI, to obtain linearized plasmids;

b'. isolation of the linearized plasmid DNA from a 1% agarose gel after gel electrophoresis followed by electro-elution in dialysis bags (1);

c'. partial digestion of ClaI-linearized pUR6002 with PstI;

d'. after separating the obtained fragments by gel electrophoresis the vector fragment with the desired length of ~5 kb was isolated as described above;

e'. the thus obtained DNA fragment with a ClaI and a PstI sticky end was ligated with a synthetic DNA fragment (shown below), with a ClaI- and a PstI sticky end.

| ClaI | CGATGAGATCTTGATCACTGCA | PstI |
|------|------------------------|------|
|      | TACTCTAGAACTAGTG        |      |

Furthermore the synthetic fragment contains a recognition site for teh restriction enzymes BclI and BglII;

f'. transformation of the ligation mixture to *E. coli* SA101 specification, and screening of the plasmids from the transformants so obtained.

Figures 3, 3A:
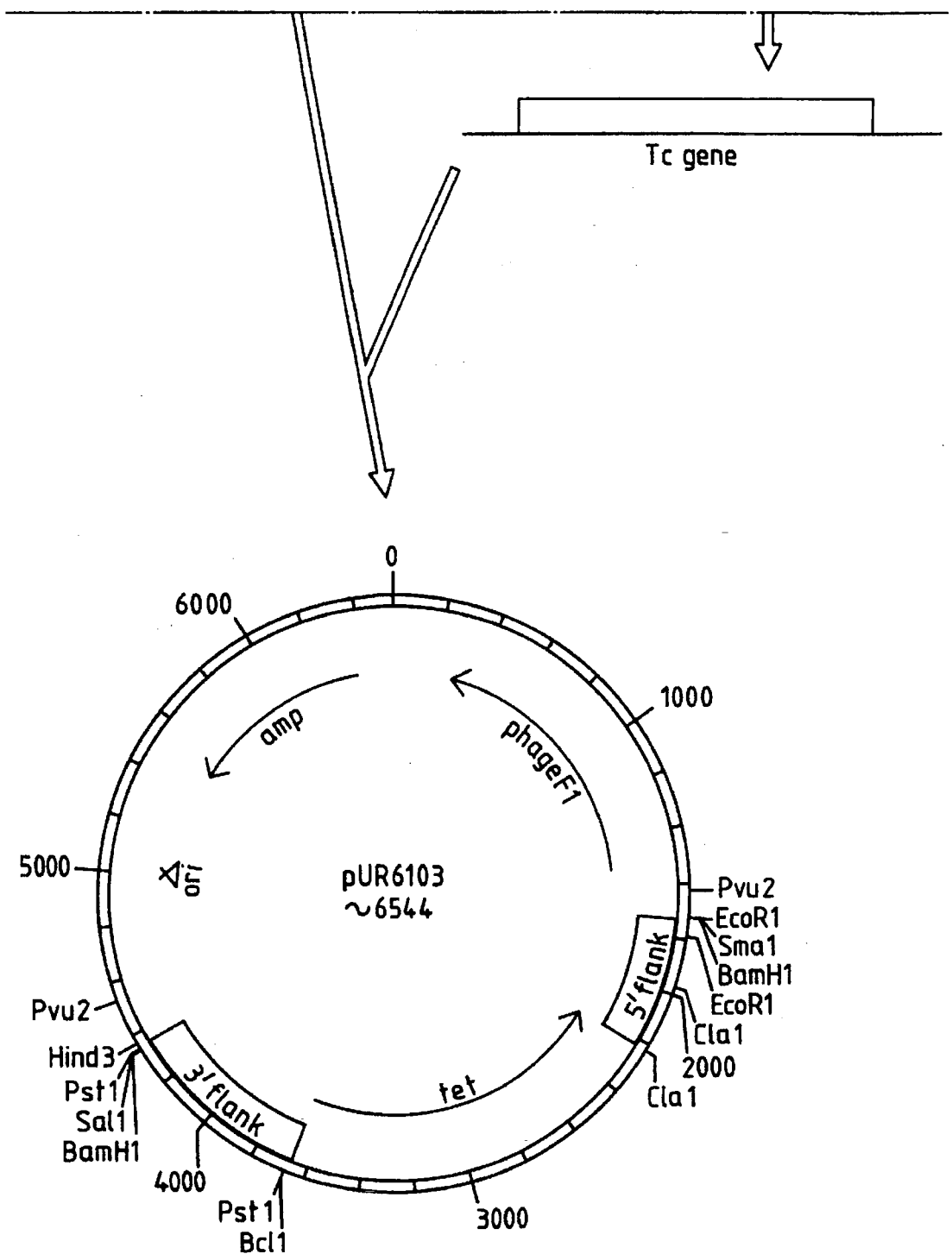
Figure 3B:
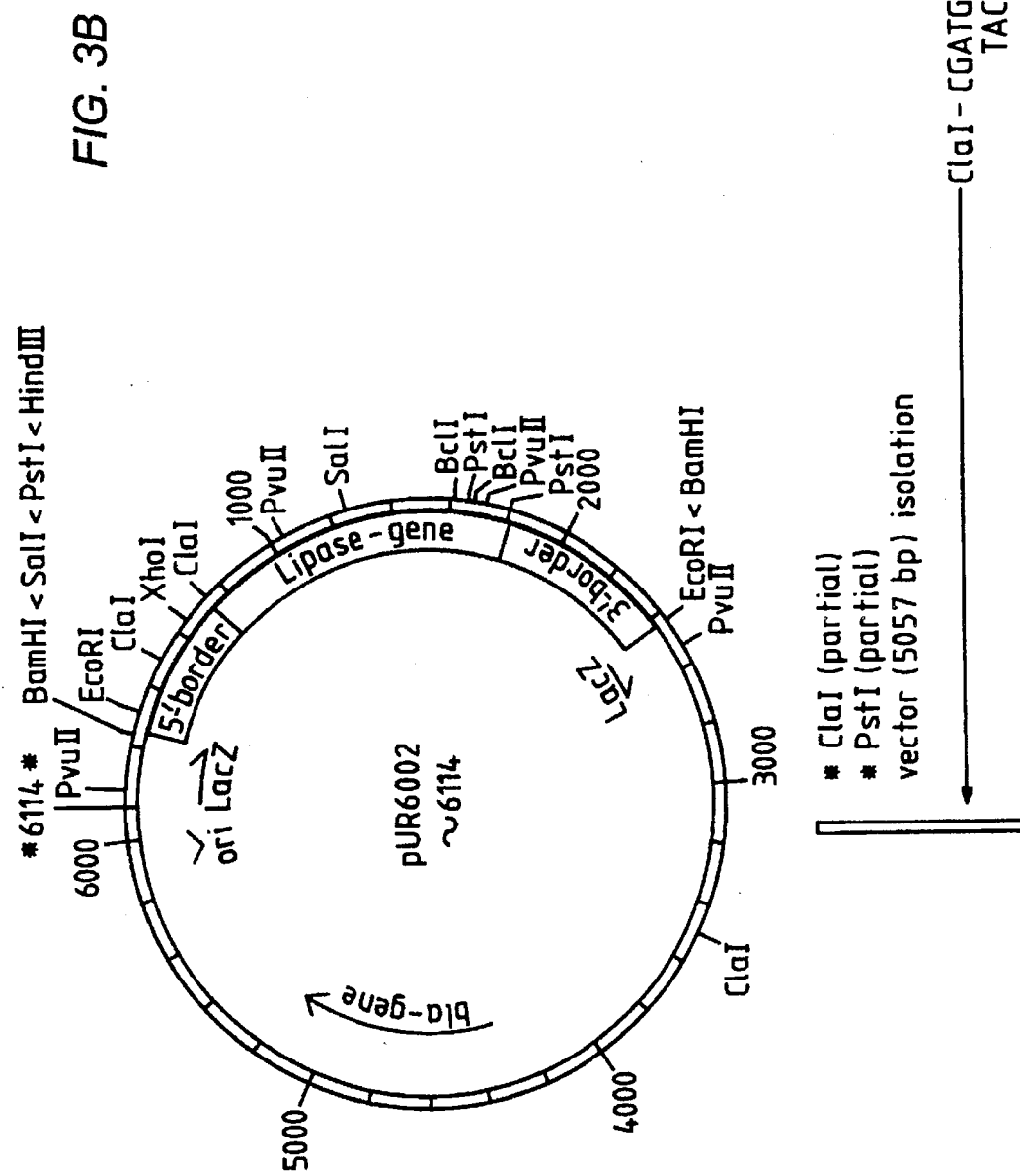
Figures 1, 3B:
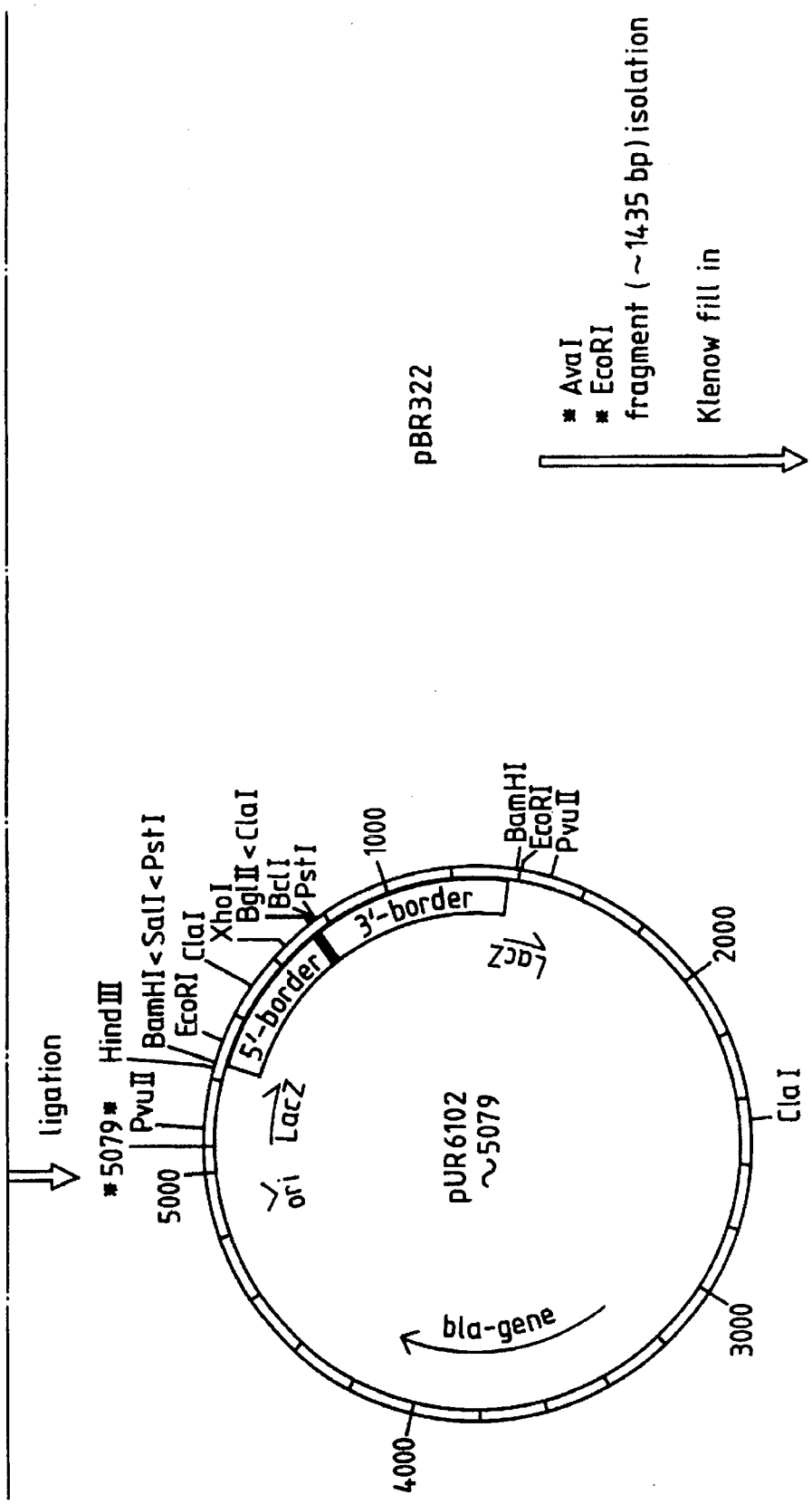
Figures 2, 3B:
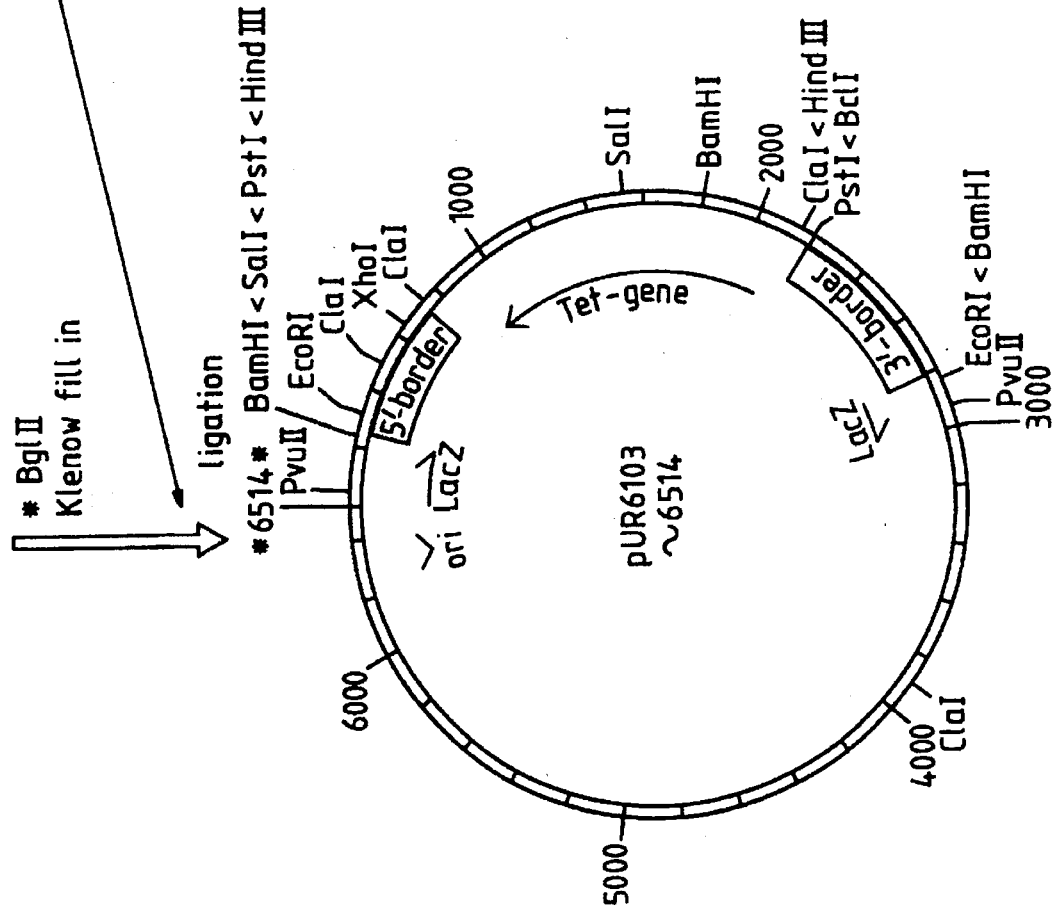
Figure 4A:
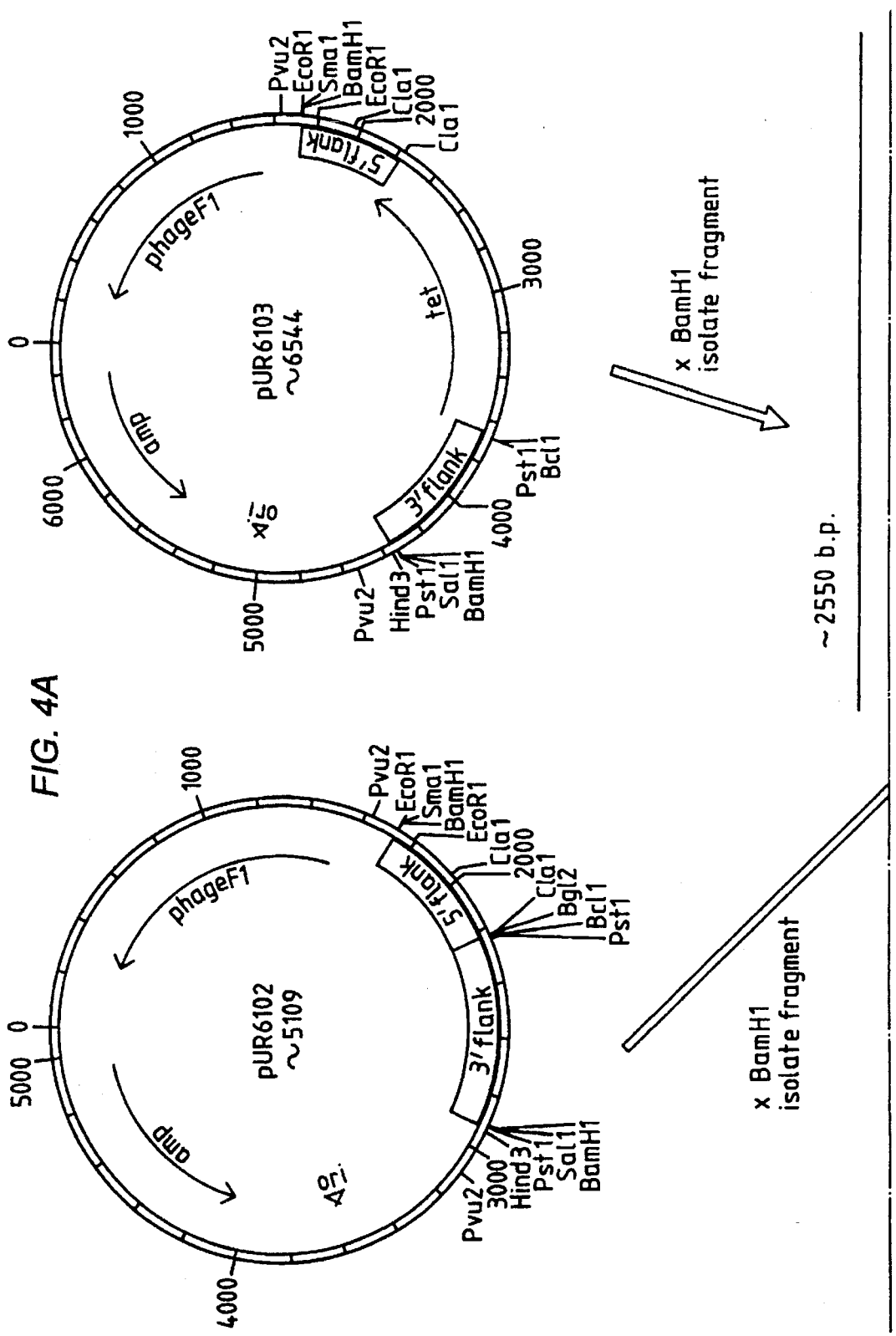
Figure 4B:
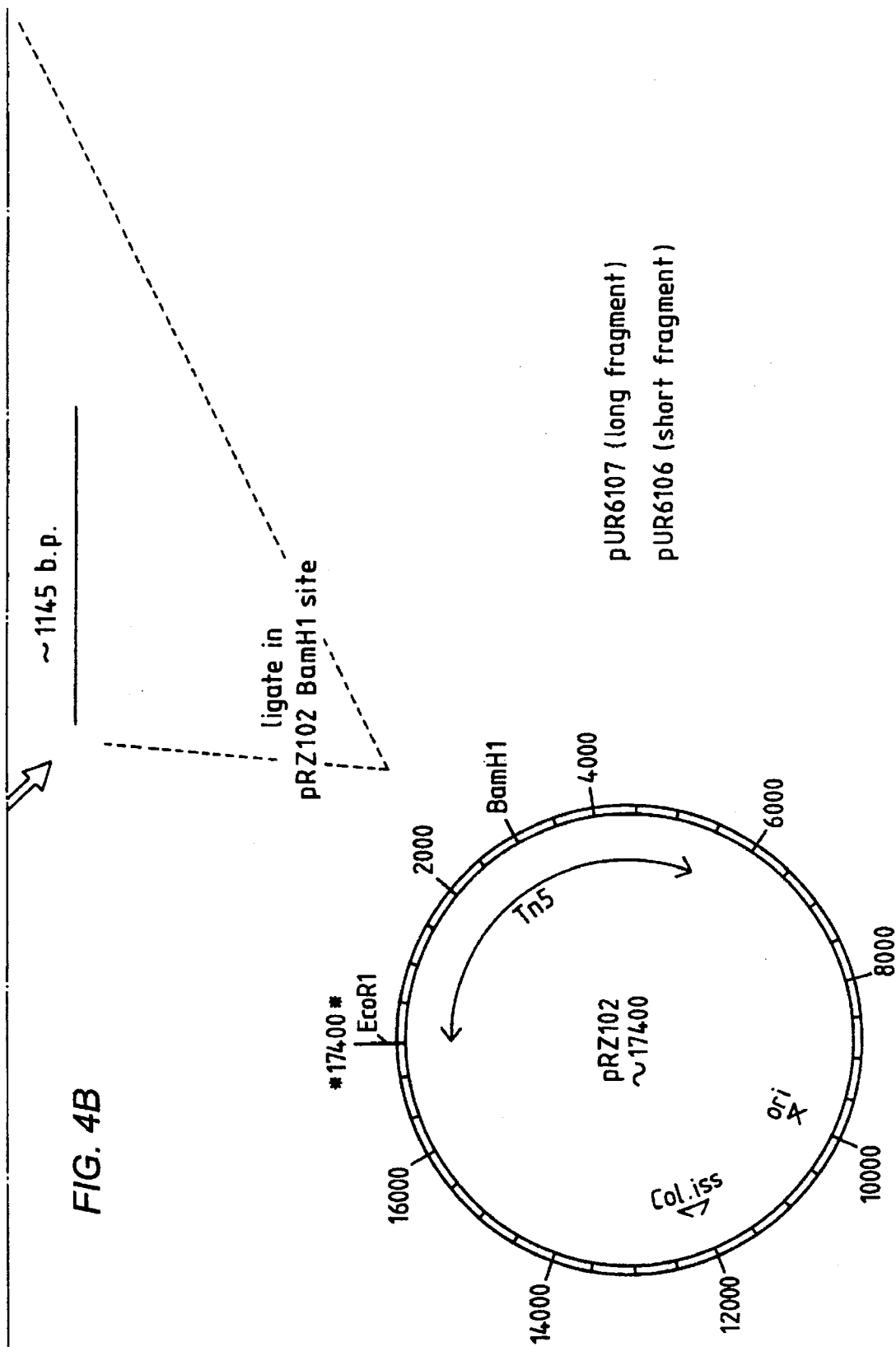

A representative of such correct plasmids is depicted in FIG. 3 and was called pUR6102.

g. pUR6102 was digested to completion with BglII;

h. pBR322 (11b) was digested to completion with AvaI and EcoRI, after which the DNA fragments were separated by agarose gel electrophoresis. A fragment of ~1435 basepairs, containing the tetracycline resistance gene was isolated from the gel by electro-elution;

i. upon filling in the sticky ends (in a buffer containing 7 mM tris-HCl pH7.5, 0.1 mM EDTA, 5 mM β-mercapthoethanol, 7 mM MgCl2, 0.05 mM dNTPs and 0.1 u/ml Klenow polymerase) of the DNA fragment containing the Tc-res gene and the linearized pUR6102 they were ligated.

j. transformation of E. coli SA101 with the ligation mixture, selection on LB-Tc (25 mg tetracycline/ml) agar plates, and screening of the plasmids from the obtained transformants by restriction enzyme analysis. The construction route of pUR6102 and pUR6103 is depicted in FIG. 3.

k. pUR6102 was digested with BamHI and pUR6103 was partially digested with BamHI; the obtained fragments were separated by agarose gel electrophoresis and the desired fragments (~1145 bp and ~2550 bp resp.) were isolated out of the gel by electro-elution.

l. pRZ102 (10) was digested to completion with BamHI and ligated to the BamHI fragments obtained in step k.

m. transformation of the ligation mixtures to E. coli S17-1 (11), selection on LB-km,Tc (25 m/ml each) and screening of the plasmids from the obtained transformants, by restriction enzyme analysis. The resulting plasmids containing a BamHI fragment were called pUR6106 and pUR6107 (FIG. 4), respectively.

B—Deletion of the lipase gene of the P. glumae chromosome.

a. Introduction of pUR6106 in P. glumae via biparental conjugation with E. coli S17-1(pUR6106) (which is the notation for E. coli S17-1 containing plasmid pUR6106).

A P. glumae colony was transferred from a MME plate (0.2 g/l MgSO4-7H2O, 2 g/l Citrate-H2O, 10 g/l K2HPO4, 3.5 g/l NaNH4HPO44H2O, 0.5% glucose and 1.5% agar) to 20 ml Luria Broth (LB) culture medium and grown overnight at 30 deg C. E. coli S17-1(pUR6106) was grown overnight in 3 ml LB medium, 25 mg/ml Km, at 37 deg C.

The next day the P. glumae culture was diluted 1:1 and grown for 4 to 5 hours at 36 deg C. until OD660 is 2.0-2.5. E. coli S17-1 (pUR6106) was diluted 1:50 and grown for 4 to 5 hours at 37 deg C. until OD660 is 1.5-2.0.

For the conjugation 50 OD units (1 unit=1 ml with OD=1) (20 to 25 ml) P. glumae cells and 2.5 OD units (1.2–1.6 ml) E. coli S17-1 (pUR6106) were mixed and spun down for 10 min at 5 krpm (HS4-rotor). The cell pellet was divided over 3 LB plates and incubated overnight at 30 deg C.

Subsequently the cell material was removed from the plate and resuspended in 3 ml 0.9% NaCl solution and pelleted by centrifugation (10 min, RT, HB4-rotor, 4 krpm). The cell pellet was resuspended in 1.8 ml 0.9% NaCl solution and divided over 3 plates MME, 0.5% glucose, 1.5% agar, 50 mg/ml kanamycin (Km) and grown at 30 deg C. Since pUR6106 does not replicate in P. glumae, Km resistant transconjugants can only be obtained by integration. In these strains the plasmid pUR6106 is integrated into the bacterial chromosome by a single recombination event at the 5'- or 3'-flanking region. Due to the fact that these strains still contain a functional lipase gene, their phenotype is lipase positive.

b. Two such strains (PG-RZ21 and PG-RZ25) were selected for further experiments. To delete the plasmid and the functional lipase gene out of the chromosomal DNA, a second recombination event should take place. This can be achieved by growing said strains for several days on LB-medium without Km (without selective pressure), plate the cells on BYPO-plates (10 g/l trypticase peptone, 3 g/l yeast extract, 5 g/l beef extract, 5 g/l NaCl, 7 g/l KH2PO4, 50 ml/l olive oil emulsion and 1.5% agar) in a density which assures separate colonies, and screen for lipase negative colonies. Upon plating these lipase negative colonies on selective plates (MME-KM 50 mg/ml), they should not grow. A strain obtained in this way could be called PG-2.

C—Replacement of the lipase gene of the *P. glumae* chromosome by the Tc-res gene.

a. Introduction of pUR6107 in *P. glumae* via conjugation with *E. coli* S17-1 (pUR6107) as described in B. Selection of trans-conjugants was performed at 30 deg C. on MME-medium containing 50 mg/ml Tc.

b. Transconjugants obtained in this way were duplicated to BYPO-plates containing 50 mg/ml Tc and to MME-plates containing 100 mg/ml Km. Several transconjugants exhibited a Km sensitivity (no growth on MME Km-100 plates) and lipase negative (no clearing zone on BYPO-plates) phenotype. Due to a double cross over (at the 5'- and at the 3'-flanking region) the lipase gene waqs repleced by the Tc resistance gene. One representative strain was selected for further investigation and was called PG-3.

REFERENCES

10. Jorgensen, R. A., Rothstein, S. J., and Reznikoff W. S. Molec. gen. Genet. 177, 65–72, (1979).
11. Simon, R., Priefer, U., and Puehler, A. Biotechnology, 784–791, (1983)
11a. Marinus M. G., Molec. gen. Genetics 127 (1973) 47–55
11b. Bolivar F. et al, Gene 2 (1977) 95.

EXAMPLE 3

Construction of a synthetic gene encoding *P. glumae* (pre)-lipase.

Based on the nucleotide sequence of the *P. glumae* (pre)-lipase gene a new gene was designed, containing several silent mutations. Due to these mutations the amino acid sequence of the enzyme was not changed. It was however possible to lower the G+C %, which facilitates enzyme engineering and enabled us to use the synthetic gene in a variety of heterologous host systems (See examples 6 to 10).

Another point, facilitating enzyme engineering, was the possibility to introduce restriction enzyme recognition sites at convenient positions in the gene.

The sequence of the new gene is given in FIG. 5(A).

The new gene was divided in restriction fragments of approximately 200 nucleotides, so-called cassettes. An example of such a cassette is depicted in FIG. 6.

Each cassette was elongated at the 5' and 3' end to create an EcoRI and HindIII site respectively.

The coding strands of these cassettes were divided in oligo-nucleotides (oligos) with an average length of 33 bases. The same was done for the non coding strands, in such a way that the oligos overlapped for 50% with these of the coding strand.

The oligos were synthesized as described in example 1.

Before assembling the fragments, the 5' ends of the synthetic oligos had to be phosphorilated in order to facilitate ligation. Phosphorylation was performed as follows: Equimolar amounts (50 pmol) of the oligos were pooled and kindred in 40 ml reaction buffer with 8 Units polynucleotide kinase for 30–45 minutes at 37 deg C. The reaction was stopped by heating for 5 minutes at 70 deg C. and ethanol precipitation.

Annealing was done by dissolving the pellet in 30 ml of a buffer containing: 7 mmol/l Tris-HCl pH 7.5, 10 mmol/l 2-mercapto-ethanol, 5 mmol/l ATP were added. Subsequently the mixture was placed in a waterbath at 65 deg C. for 5 minutes, followed by cooling to 30 deg C. over a period of 1 hour. MgCl2 was added to a final concentration of 10 mmol/l. T4 DNA-Ligase (2.5 Units) was added and the mixture was placed at 37 deg C. for 30 minutes or o/n at 16 deg C. After this the reaction mixture was heated for 10 minutes at 70 deg C. After ethanol precipitation the pellet was dissolved in digestion buffer and cut with EcoRI and HindIII.

The mixture was separated on a 2% agarose gel and the fragment with a length corresponding to the correctly assembled cassette was isolated by electro-elution.

The fragments were ligated in pEMBL9 (digested with EcoRI/HindIII) as described in example 1, and they were checked for correctness by sequence analysis. In subsequent cloning steps the various cassettes were put together in the proper order, which resulted in pUR6038. This is a pEMBL9 derivative containing the complete synthetic lipase gene.

To be able to make the constructions as described in example 4, a second version of the synthetic gene was made, by replacing fragment 5. In this way construct pUR6600 was made, having the 3' PstI site at position 1069 instead of position 1091 (See FIG. 5).

EXAMPLE 4

Introduction of the (wild type) synthetic lipase gene in the lipase negative *P. glumae* PG3.

In order to test whether the synthetic lipase gene is functional in *P. glumae*, the gene was introduced in strain PG3. To simplify fermentation procedures, it was decided to stably integrate this gene in the PG3 chromosome, rather than introducing on a plasmid. For this reason the synthetic lipase gene had to be equipped with the 5' and 3' border sequences of the original *P. glumae* lipase gene.

Figure 7A:
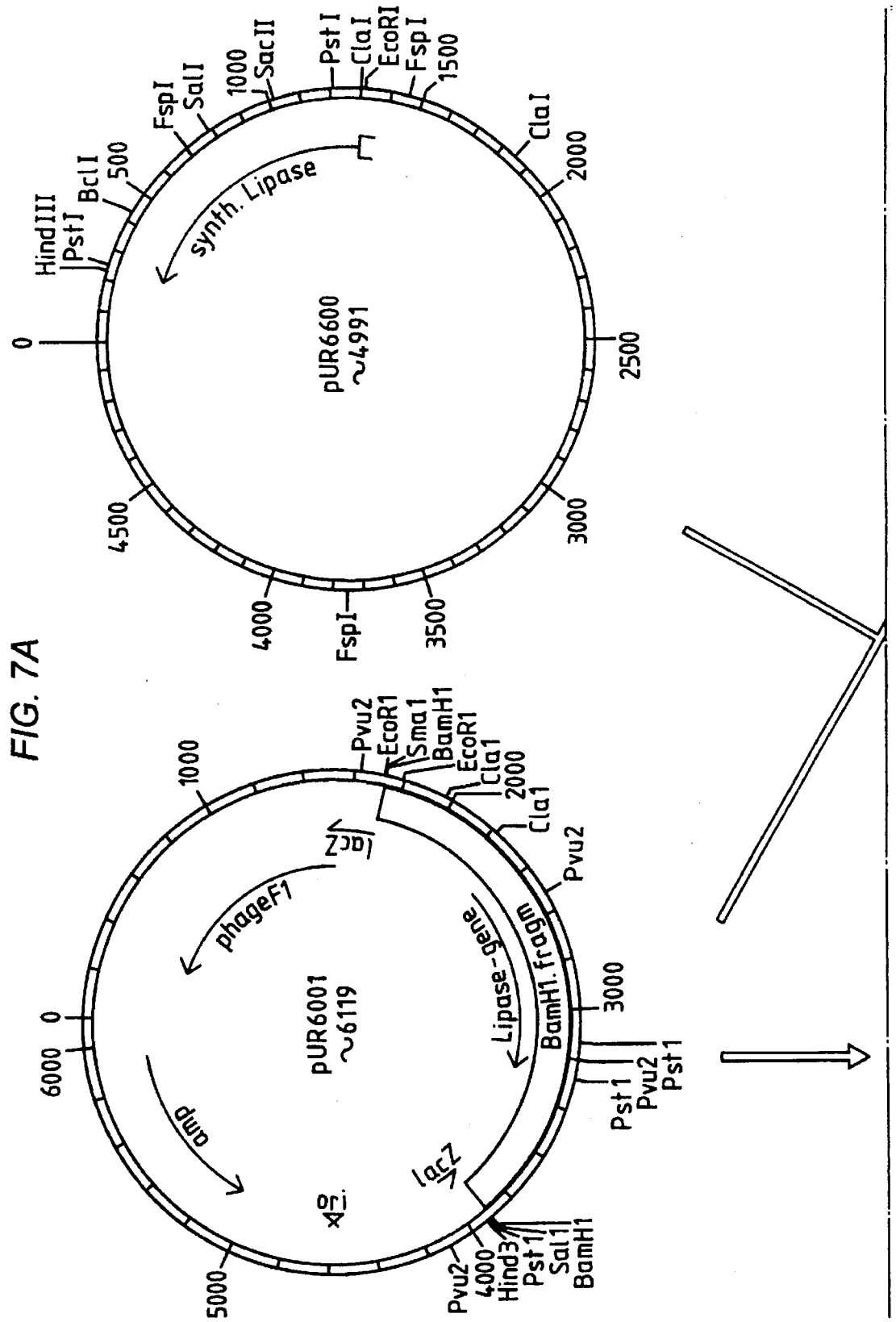
Figures 1, 7A:
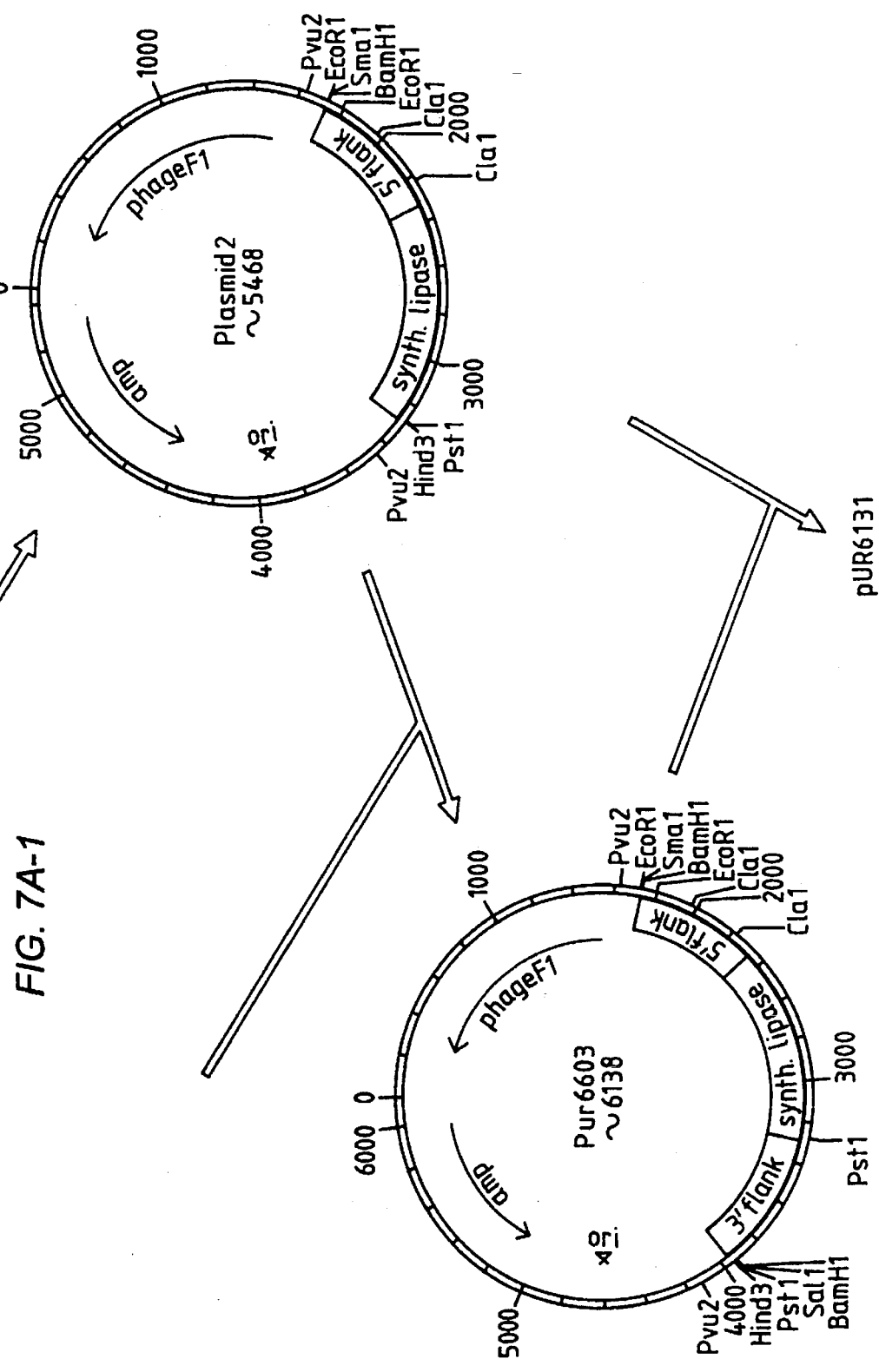
Figures 1, 7B:
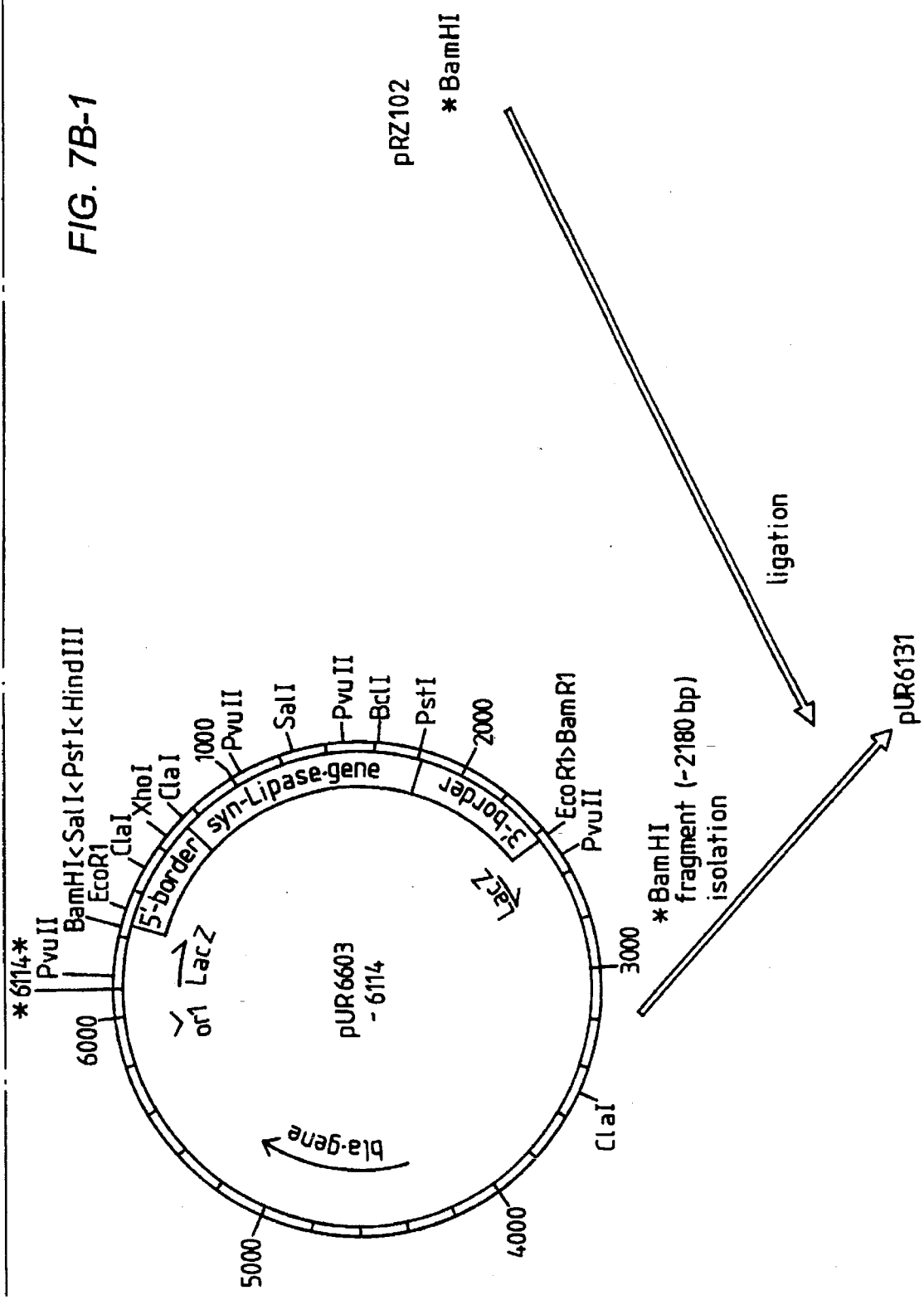

This was achieved in the following way (see FIG. 7):

a. partial digestion of pUR6001 (ex *E. coli* KA816) with ClaI, to obtain linearized plasmids;

b. phenol extraction and ethanol precipitation (1) of the DNA, followed by digestion with PstI;

c. isolation of a ~4.5 kb plasmid DNA fragment (having ClaI and PstI sticky ends), and a PstI fragment of ~670 bp;

d. partial digestion of pUR6600 (ex *E. coli* KA816) with PstI followed by phenol extraction, ethanol precipitation and digestion with ClaI;

e. after isolating a DNA fragment of ~1050 bp, comprising almost the entire synthetic lipase gene, this fragment was ligated in the ~4.5kb vector obtained in step c: after transformation of the ligation mixture to *E. coli* SA101, selection on LB-Ap (100 microgram ampicillin/ml) plates, and screening of the plasmids from the obtained transformants by restriction enzyme analysis, a correct plasmid (No 2) was obtained for the next construction step;

f. the plasmid construct (No 2) obtained as described in step e was digested with PstI, and ligated together with the ~670 bp PstI fragment isolated as described in step c;

g. transformation of the ligation mixture to *E. coli* SA101, selection on LB-Ap (100 microgram ampicillin/ml) plates, and screening of the plasmids from the obtained transformants: since the PstI fragment can have two different orientations, this had to be analyzed by means of restriction enzyme analysis: in the construct we were looking for, the orientation should be thus, that digestion with BamHI results in a vector frgament of ~4 kb and an insert fragment of ~2.2 kb: a representative of the correct plasmid was called pUR6603;

h. pUR6603 was digested to completion with BamHI: after separating the fragments by agarose gel electrophoresis a fragment of ~2.2kb was isolated: this fragment contained the synthetic lipase gene with the 5' and 3' flanking regions;

i. pRZ102 was also digested to completion with BamHI;

j. the 2.2 kb fragment obtained in step d was ligated with pRZ102 as described in Example 2;

k. the resulting construct, pUR6131, was transferred to *E. coli* S17-1.

A less preferred alternative route is (see FIG. 7b):

a'. From pUR6002 (ex *E. coli* KA816), a vector with ClaI and PstI sticky ends was prepared in the same way as described in example 2.

b'. pUR6660 (ex *E. coli* KA816) was digested to completion with ClaI and partial with PstI. After separating the fragments by agarose gel electrophoresis a fragment of ~1050 bp was isolated.

c'. The fragment thus obtained, was ligated in the pUR6002 derived vector and used to transform *E. coli* SA101. In this way construct pUR6603 was obtained.

d'. pUR6603 was digested to completion with BamHI. After separating the fragments by agarose gel electrophoresis a fragment of ~2.2 kb was isolated. This fragment contains the synthetic lipase gene with the 5' and 3' flanking regions, of the wild type *P. gladioli* lipase gene.

e'. pRZ102 was also digested to completion with BamHI.

f'. The 2.2 kb fragment obtained in d. was ligated in pRZ102 as described in example 2.

g'. The resulting construct, pUR6131 was transferred to *E. coli* S17-1. Integration of this construct in the chromosome of PG3 was accomplished in the same way as descirbed for pUR6106 in example 2 section B-a.

From the obtained Km-resistant transconjugants, several were transferred to BYPO plates. They all appeared to have the lipase positive phenotype, since clearing zones occured around the colonies. A typical representative was called PGL26.

Obviously the same route can be followed to integrate construct (pUR6131) in a lipase negative *P. glumae* PG2 (see example 2B-b) strain.

From the examples 2 and 4 it might be clear that the *Ps. glumae* strain PG1 (and derivatives thereof, e.g. PG2 and PG3; or derivatives of PG1 obtained via classical mutagenesis having an improved lipase production) can be manipulated easily by deleting or introducing (homologous or heterologous) DNA fragments in the bacterial chromosome.

By using these techniques it is possible to construct a strain optimized for the production of lipase, for example, by replacing the original lipase promotor with a stronger (regulatable) promotor, introducing more than one copy of the lipase gene (possibly encoding different lipase mutants), replacing the original promoter, or introducing more copies of genes encoding functions involved in the production and excretion of the lipase enzyme (eg. chaperon proteins, "helper proteins" involved in the export of the lipase enzyme), deleting the gene encoding extracellular protease (A Tn5 mutant of PG1 (PGT89) which does not produce a clearing zone or skimmilk plates has been deposited), and manipulating the rhamnolipid production.

EXAMPLE 5

Production of mutant lipase genes and their introduction in PG3.

To improve the lipase, it is necessary to have the possibility to introduce well-defined changes in the amino acid sequence of the protein. A preferred method to achieve this is via the replacement of a gene fragment of the synthetic gene encoding wild type lipase or of the wild type *P. glumae* lipase gene, with a corresponding chemically synthesized fragment containing the desired mutation. In the case of the synthetic wild type lipase gene, a cassette (or fragment thereof) can be replaced with a corresponding cassette (or fragment thereof) containing the desired mutation.

The cassette, comprising the codon(s) for the amino acid(s) of interest, was assembled once more (as described in Example 3). This time however, the oligos of the coding and the non-coding DNA strands, comprising the codon(s) of interest, were replaced by oligomers with the desired mutation. The new oligos were synthesised as described in Example 1. The thus obtained mutant cassette, or a fragment thereof was introduced at the corresponding position in the synthetic wild type lipase gene of constructs like pUR6038 or pUR6603.

To introduce a synthetic mutant lipase gene in PG2 or PG3, the route as described in Example 4 has to be followed, starting at step d.

Figure 6:
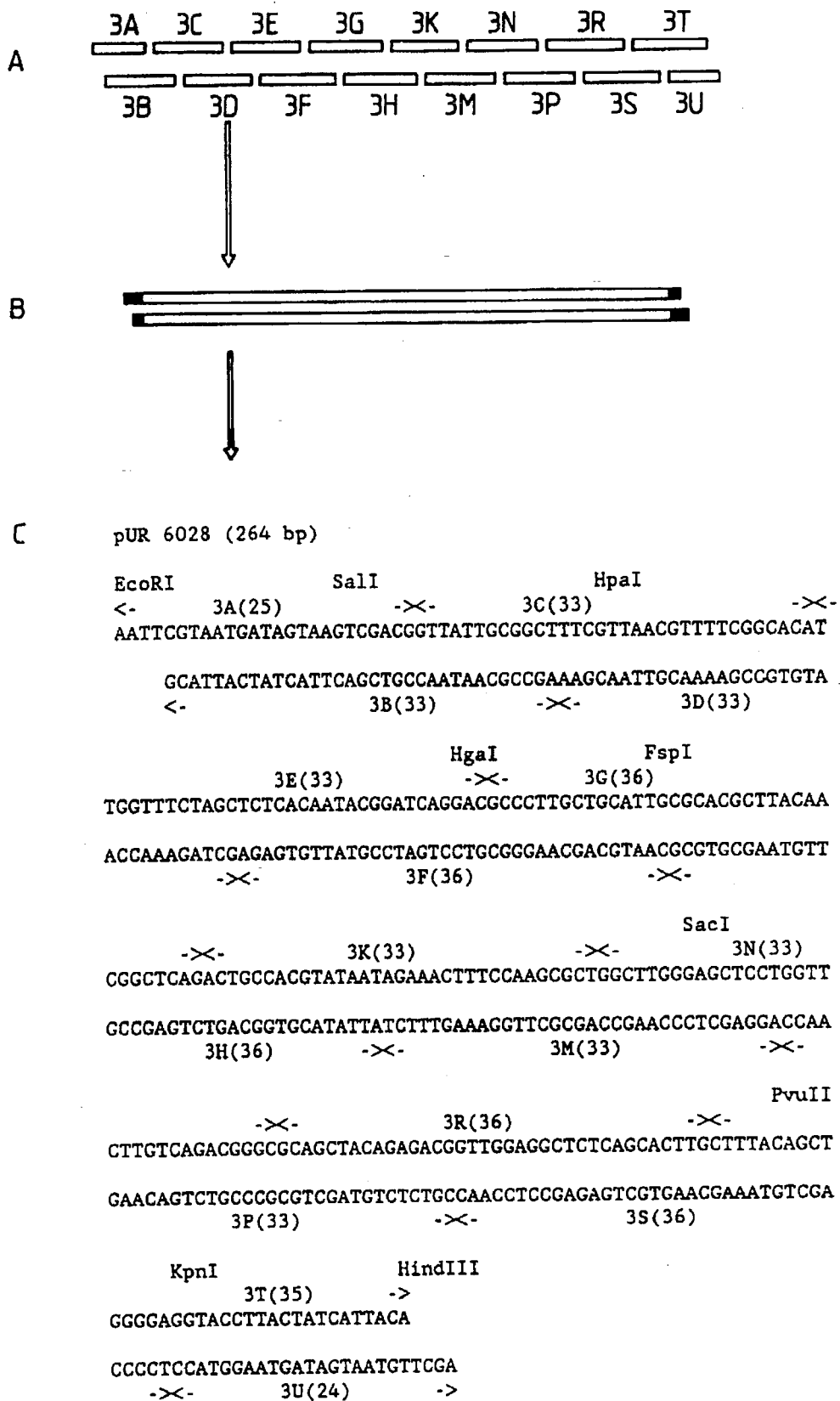
Figure 8:
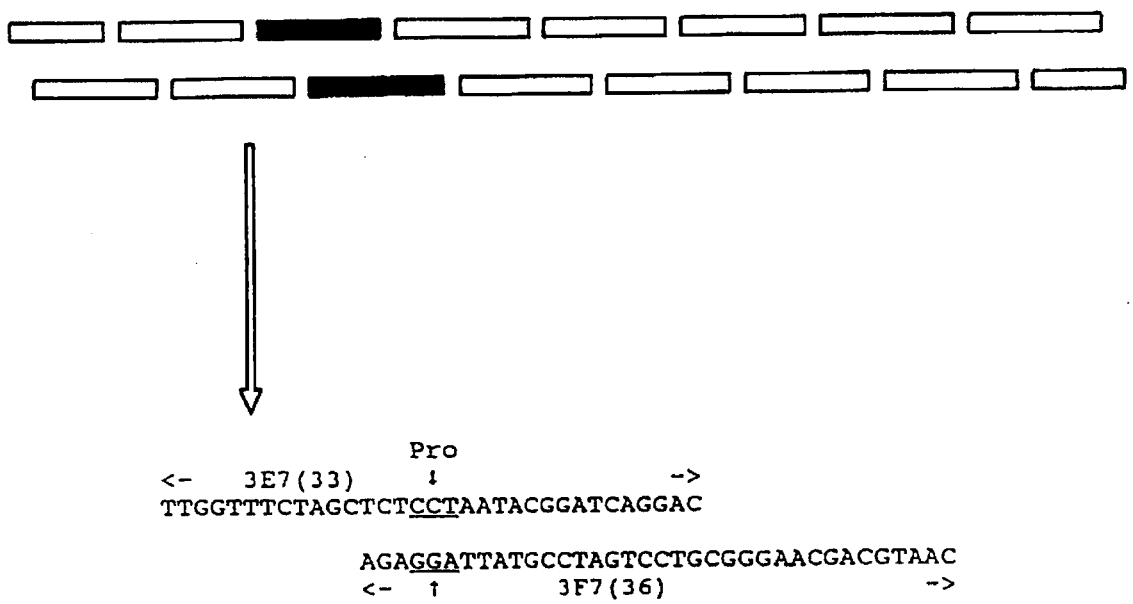

A typical example of the production of a mutant gene is depicted in FIG. 8 (compare FIG. 6). In this case the His at position 154 of the wild type lipase gene has been replaced by a Pro. To accomplish this, two new oligomers were synthesized, the nucleotide sequences of which is depicted in FIG. 8. The codon encoding amino acid 154 the mature lipase is changed to CCT. These oligomers were used to assemble fragment 3(H154P), as described in example 3. After cloning the fragment in pEMBL9, the DNA sequences was determined as described in example 1.

The thus obtained construct was called pUR6071. Plasmid pUR6071 was digested to completion with FspI and SalI. Upon separation of the obtained DNA fragments via gel electro-phoresis (as described in example 2), a fragment of ~90 bp was isolated out of agarose gel.

pUR6002 was partially digested with FspI and partially with SalI. After gel electrophoresis a vector of ~6000 nucleotides was isolated out of the agarose gel as described in Example 2. The isolated ~90 bp fragment was ligated in the pUR6002 vector to obtain pUR6077A. The BamHI fragment (~2200 bp) of pUR6077A was ligated in pRZ102 as described in examples 3 and 4. In this way pUR6127 was obtained.

Introduction of this construct into the chromosome of PG3 was accomplished as described in example 4. A resulting lipase producing *P. glumae* transconjugant, was called PGL24. The modified lipase produced by this strain proved to be significantly more stable than the parent lipase in an actual detergents system (see example 11).

In essentially the same way several other mutant lipase genes have been made. In some cases this resulted in a altered net charge of the encoded protein (eg. D157R (+2), D55A (+1), I110K (+1), R61P (−1), T109D (−1), RSD (−2)). In other cases amino acids have been introduced or deleted (eg. PGL40 in which 152S-154H has been replaced by ALSGHP). Furthermore potential glycosylation sites have been removed (eg. N48S and/or N238S) and/or introduced (eg. D157T and insertion of G between N155 and T156). These and other mutants are presented in table 1.

EXAMPLE 6

Expression of synthetic lipase genes in *B. subtilis*.

As Gram positive bacteria, in particular Bacillus, are considered very good hosts for the introduction of hydrolases and since much is known with respect to the fermentation process, the lipase gene from the Gram negative *P. glumae* has been introduced in *B. subtilis*, on several different expression vectors.

Expression plasmid pMS48 (12), containing the SPO2 promoter, was used as a basis for constructs containing recombinant lipase genes, encoding:

1. pre-lipase,
2. mature lipase preceded by a methionine,
3. mature lipase preceded by the signal sequence of amylase.

Plasmid pUB110 (13), containing a promoter near the HpaII site (HPA-promoter), was used as a basis for constructs containing recombinant lipase genes encoding:

4. mature lipase by the subtilisin BPN' protease preprosequence,
5. different C-terminal fragments of the pre-sequence of the lipase, followed by the mature lipase and preceded by the subtilisin BPN' pre-sequence.

Figure 9A:
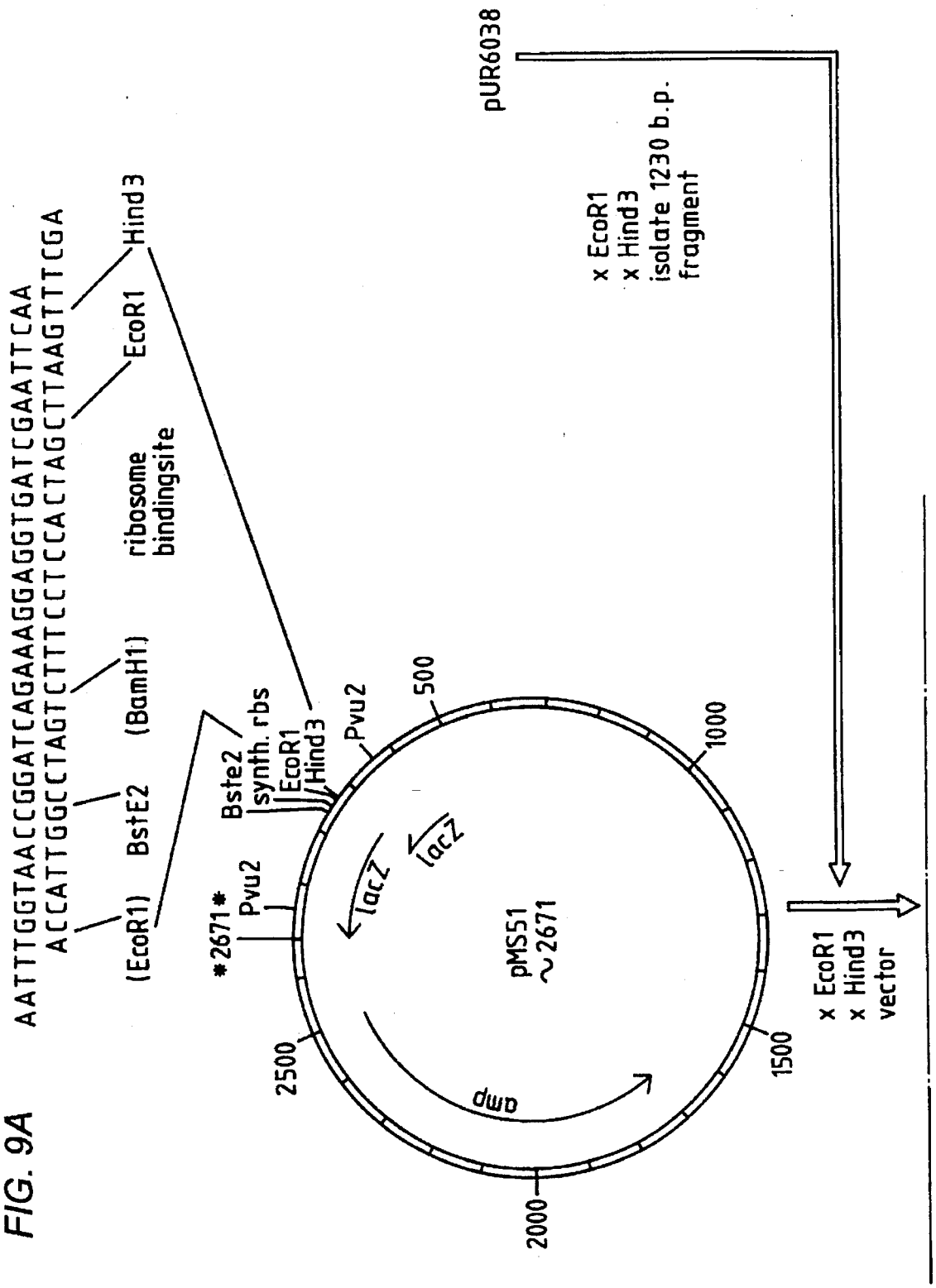
Figure 9B:
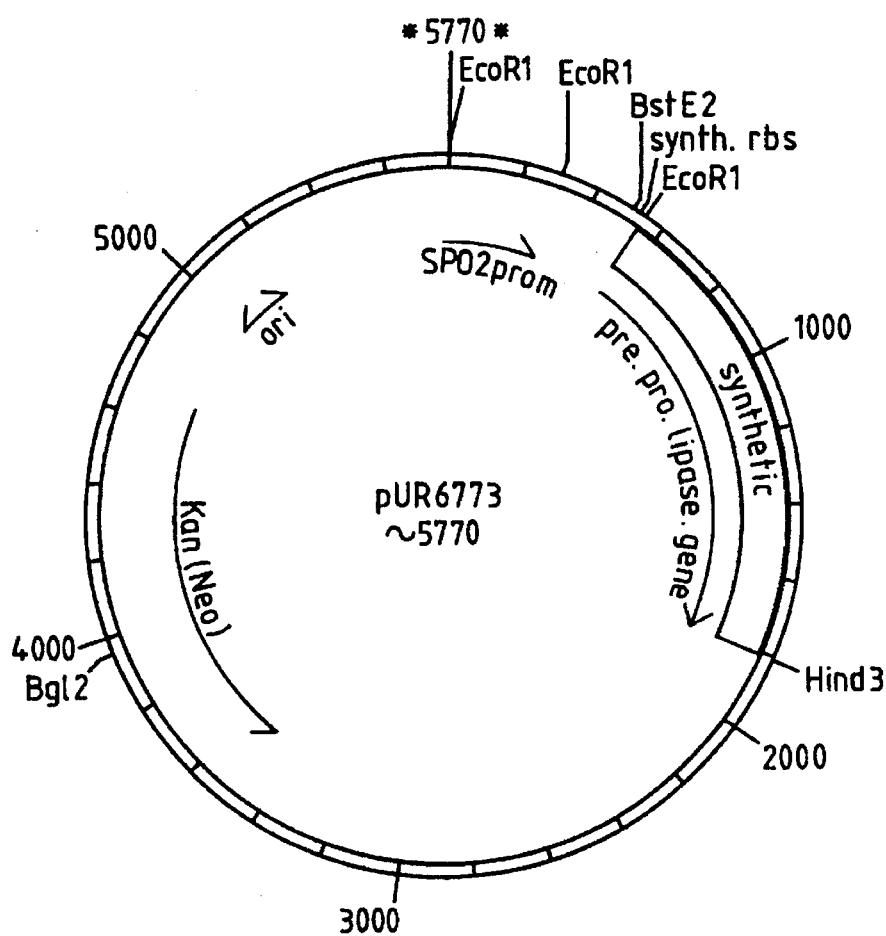
Figure 10:
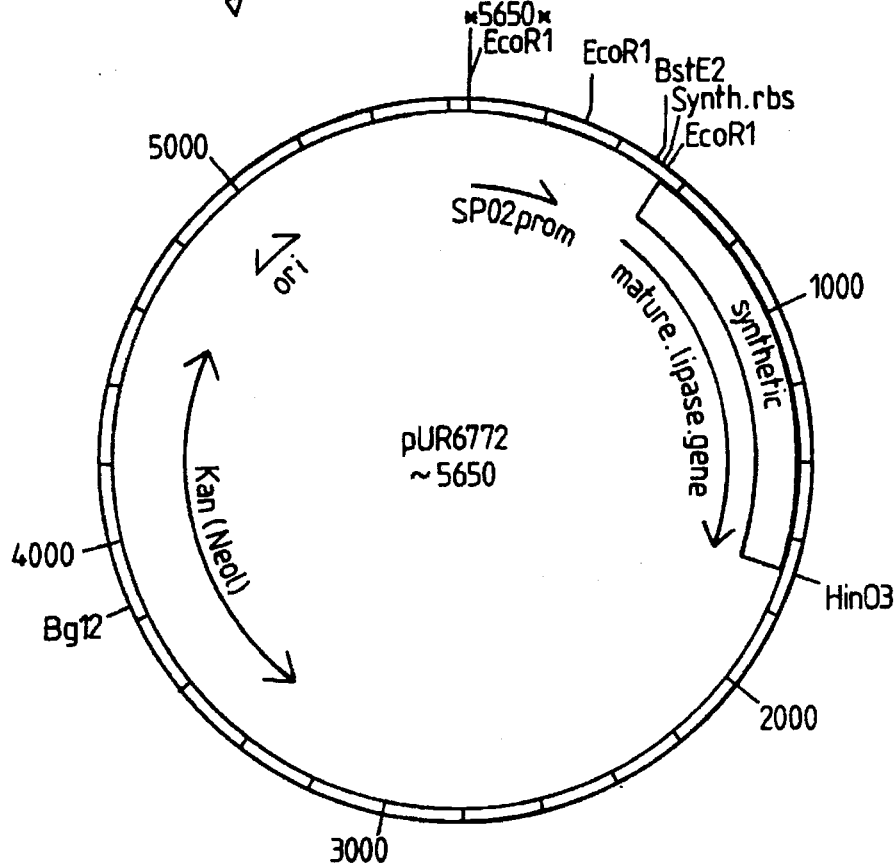
Figure 11B:
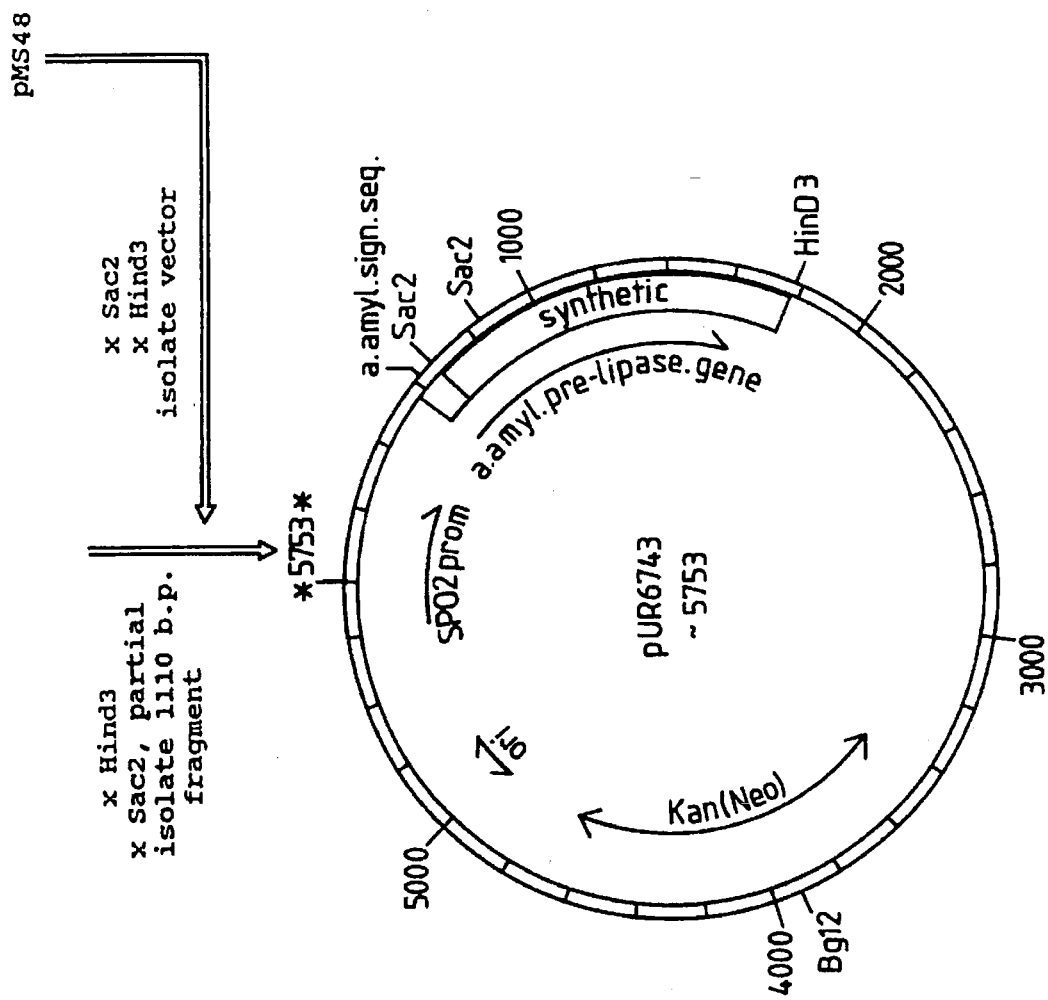

In order to obtain the above mentioned constructs, the routes followed were:

ad 1. (see FIG. 9)

a. pUC9 (14) was digested with EcoRI and HindIII, after which the linear vector fragment was purified by agarose gel electrophoresis and electro-elution, as described in example 2.

b. a synthetic linker (consisting of two oligonucleotides), having EcoRI and HindIII sticky ends, was ligated in the above mentioned vector. In the case of the EcoRI sticky end the EcoRI site was not restored. The sequence of this fragment, containing a BstEII and an EcoRI site as well as a ribosome binding site, is shown in FIG. 9. In this way pMS51 was obtained.

c. pMS51 was digested with EcoRI and HindIII.

d. pUR6038 was digested with EcoRI and HindIII, after which a fragment of ~1230 bp (containing the synthetic lipase gene) was purified by agarose gel electrophoresis and electro-elution.

e. the lipase gene fragment was ligated in the pMS51 vector (prepared in c) which resulted in pUR6771.

f. pMS48 was digested to completion with BstEII and HindIII followed by purification of the vector fragment as described above.

g. pUR6771 was also digested with BstEII and HindIII and the lipase gene fragment (~1250 bp) was purified.

h. the obtained fragment and vector were ligated and transferred to *B. subtilis* DB104 (15) according to the method as described by J. Kok (12). In this way pUR6773 was obtained.

ad 2. (see FIG. 10).

a. pUR6771 was digested to completion with EcoRI and EcoRV after which the vector fragment was purified as described above.

b. a synthetic linker having EcoRI and EcoRV ends was ligated in said vector. The sequence, encoding the first eight amino acids of the mature lipase, preceded by ATG codon as translational start-signal is presented in FIG. 10. In this way pUR6770 was obtained.

c. after digesting pUR6770 with BstEII and HindIII, a ~1130 bp fragment was purified as described earlier.

d. this fragment, containing the gene encoding mature lipase, was ligated in the vector prepared under ad. 1 f.

e. upon transformation to *B. subtilis* DB104 (see ad. 1 h.) pUR6772 was obtained.

ad 3. (see FIG. 11).

a. pUR6038 was digested to completion with EcoRI and EcoRV, after which the vector fragment was purified.

b. a synthetic linker, having EcoRI and EcoRV ends was ligated into said vector. The nucleotide sequence of the used linker is given in FIG. 11. Thus pUR6752 was obtained.

c. after digesting pUR6752 with HindIII and partially with SacII, a fragment of ~1110 bp could be purified.

d. pMS48 was digested to completion with SacII and HindIII after which the vector fragment was purified.

e. the ~1100 bp fragment (c.), containing a gene fragment encoding mature lipase, was ligated in the pMS48 vector and transferred to B. subtilis DB104 in order to obtain pUR6743.

f. After isolating the plasmids (1) from several transformants, they were digested with various restriction enzymes in order to analyze their restriction patterns. It turned out that no plasmid could be found having the expected restriction pattern. Furthermore none of the obtained transformants showed lipase production.

Upon transforming other Bacillus strains (e.g. B. licheniformis or B. amyloliquefaciens) the same kind of results were obtained. From this it had to be concluded that it is not possible to maintain the construct pUR6743 in a stable way in B. subtilis nor in other Bacillus strains, like B. licheniformis or B. amyloliquefaciens.

Figure 13A:
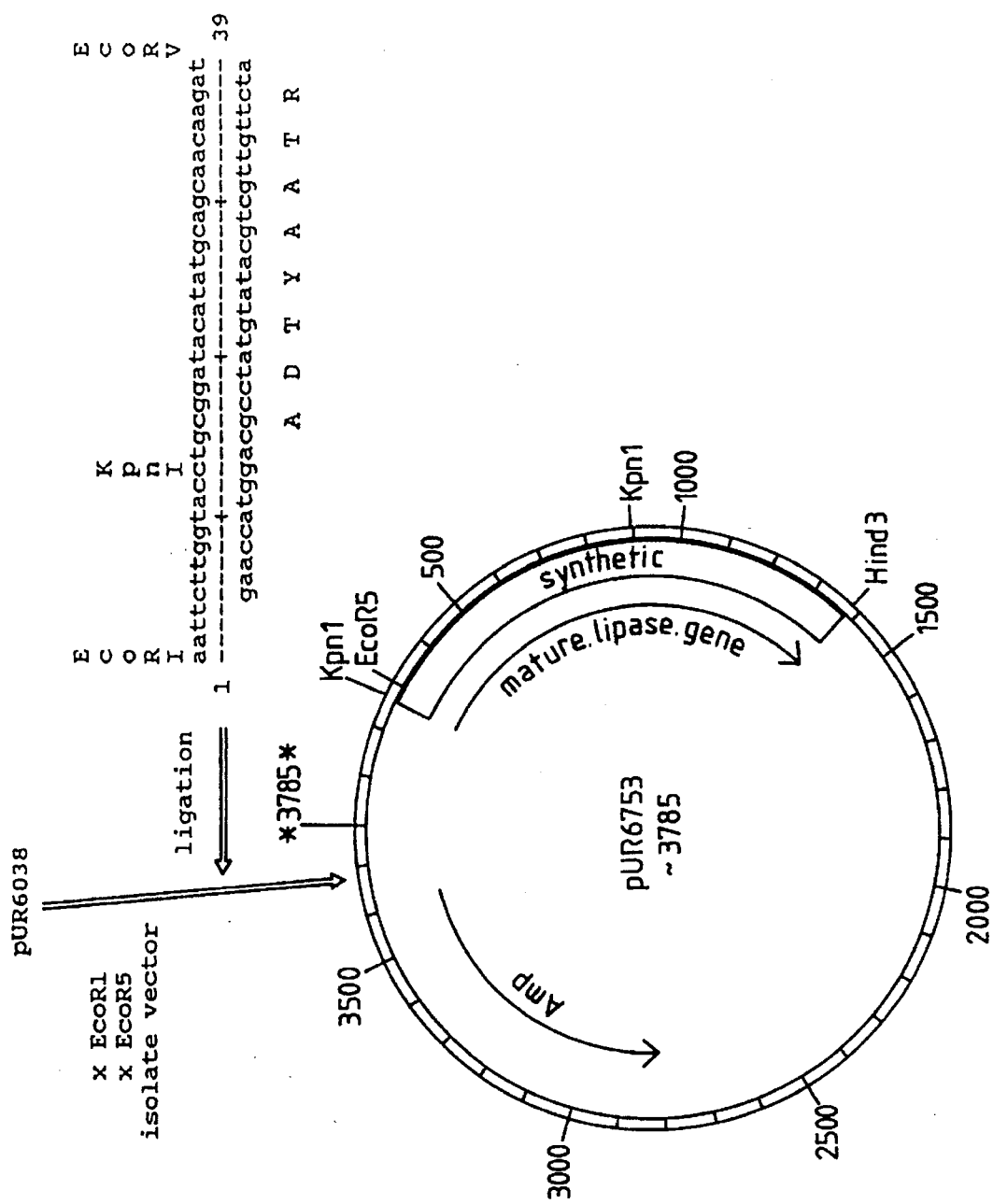
Figure 13B:
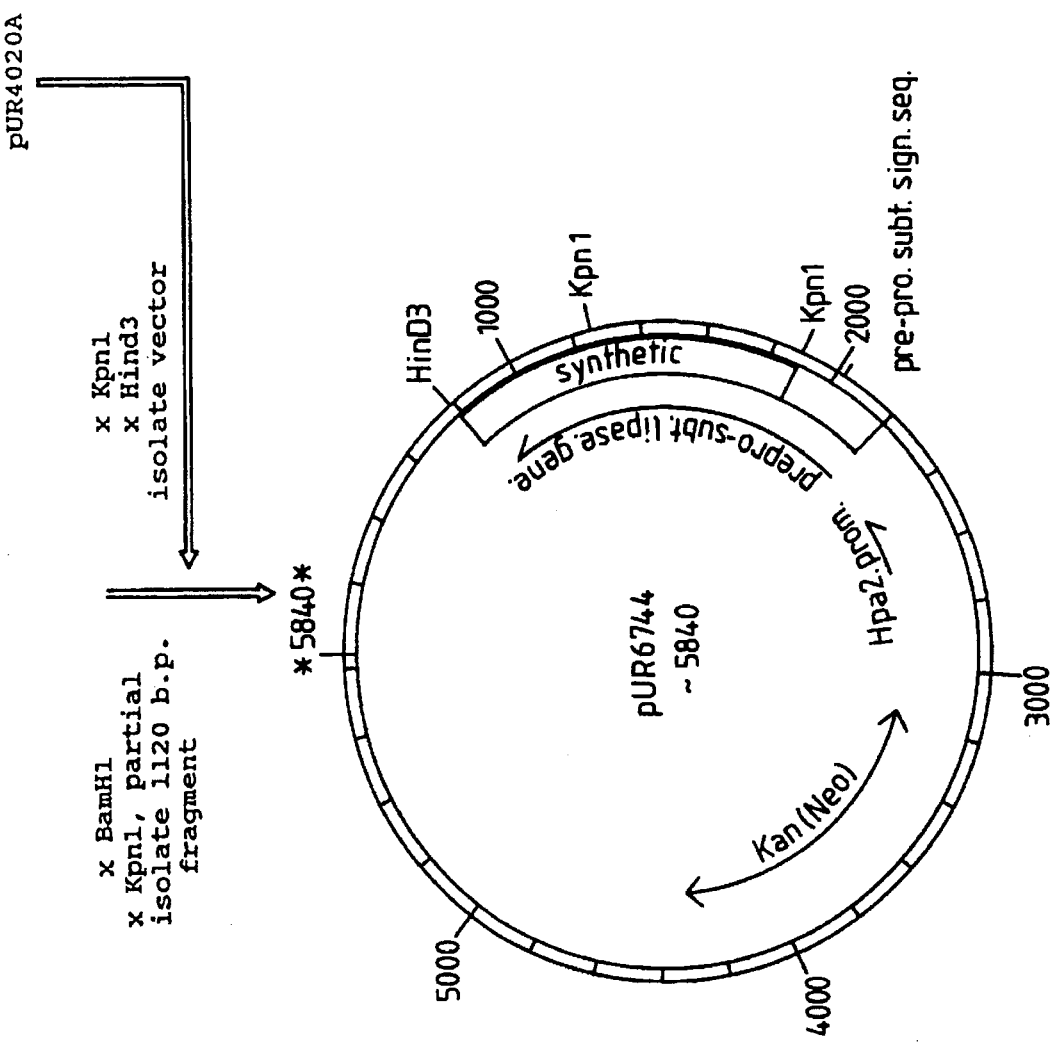

For the preparation of the constructs mentioned under point 4 and 5, it was decided to make a synthetic gene-fragment encoding the subtilisin BPN' protease prepro-sequence preceded by a 5' non-coding region. The nucleotide sequence required was taken from Wells et al. (16). This fragment was divided in 3 cassettes and prepared in the same way as described in example 3. After assembling the separate cassettes the final (EcoRI/HindIII) fragment (~570 bp) was cloned in M13mp19. The nucleotide sequence of the fragment is given in FIG. 12a. After digesting the M13mp19 derivative with EcoRI and HindIII, the ~570 bp fragment has been purified as described above. As a next step this fragment was equipped with two linkers, changing the EcoRI site and the HindIII site in SphI and BamHI sticky ends respectively. The linkers used, as well as the final sequence are depicted in FIG. 12b. pUB110 was digested to completion with SphI and BamHI, after the vector fragment was purified. The obtained vector and the SphI/BamHI fragment were ligated and transferred to B. subtilis DB104. In this way pUR4020A was obtained.

ad 4.(see FIG. 13).

a. pUR6038 was digested to completion with EcoRI and EcoRV, after which the vector fragment was purified.

b. a synthetic linker, having the same ends was ligated into said vector. The nucleotide sequence of the used linker is given in FIG. 13. Thus pUR6753 was obtained.

c. after digesting pUR6753 with BamHI and partially with KpnI a fragment of __1100 bp could be purified.

d. pUR4020A was digested to completion with KpnI and BamHI after which the vector fragment was purified.

e. this fragment, containing a gene fragment encoding mature lipase, was ligated in the pUR4020A vector and transformed to B. subtilis DB104, in order to obtain pUR6744.

f. After isolating the plasmids (1) from different transformants, they were digested with several restriction enzymes in order to analyze their restriction patterns.

It turned out that no plasmid could be found having the expected restriction pattern. Furthermore non of the obtained transformants showed lipase production.

Upon transforming other Bacillus strains (e.g. B. licheniformis or B. amyloliquefaciens) the same kind of results were obtained. From this it had to be concluded that it is impossible to maintain the construct pUR6744 in a stable way in B. subtilis nor in other Bacillus strains, like B. licheniformis or B. amyloliquefaciens.

The constructs described in sections ad 3 and ad 4 did not result in production and excretion of biological active lipase. This demonstrates that this liapse cannot be expressed in heterologous hosts, by just following routes known from the general literature.

We also constructed some expression plasmids in which the subtilisine pre-sequence was properly connected to lipase genes encoding mature lipase preceded by lipase pre-fragments of different length.

ad 5. (see FIG. 14)

a. pUR6038 was digested to completion with EcoRI and EcoRV, after which the vector fragment was purified.

b. synthetic linkers, having the same sticky ends were ligated into said vector. A few typical examples of said linkers and constructs obtained (pUR6763, 6764 and 6765 do.) are given in FIG. 14. By using these different linkers it was possible to join genes fragments encoding different (pre)-lipase to the BPN' protease pre-sequence gene fragment. This was done in order to establish an optimal construct with respect to expression, processing and export of the lipase enzyme.

c. pUR4020A was digested to completion with SalI and BamHI followed by purification of the vector band.

d. the constructs obtained under b. were digested with BamHI and partially with SalI, after which the fragments of ~1150 bp were purified.

e. these fragments were ligated in the pUR4020A vector and transferred to B. subtilis DB104. In this way pUR6766, 6767 and 6768 (ao.) were obtained.

The B. subtilis DB104 strains containing pUR6773 (ad 1), pUR6772 (ad 2), pUR6766, pUR6767 and pUR6768 as well as a strain containing plasmid pUB110 (negative controle) were grown on LB medium in Erlenmeyer flasks, in the presence and absence of olive oil. It could be clearly seen that the oil droplets disappeared in all cases except for B. subtilis DB104 (pUR6772) and DB104 (pUB110) indicating the production and secretion of functional lipase. Western analysis of the cells as well as the culture medium showed production of lipase.

REFERENCES

12. Kok, J. et al., (1985) EP-A- 0 157 441
13. Lacey, R. W. and Chopra, J., (1974) J. Medical Microbiology vol. 7, pp 285–287
14. Vieira, J. and Messing, J., (1982) Gene vol. 19, pp 259–268.
15. Kawamura, F. and Doi R. H., (1984) J. Bacteriology vol. 160, pp. 442–444
16. Wells, J. A. et al., (1983) Nucleic Acids Research vol. 11, pp 7911–7925

EXAMPLE 7

Expression of the synthetic lipase genes in Saccharomyces cerevisiae.

To illustrate the production of P. glumae lipase by eucaryotic micro-organisms, vectors suited for expression of P. glumae lipase in the yeast S. cerevisiae using the GAL7 promoter (17) were constructed. The P. glumae lipase is produced by the yeast S. cerevisiae using two different expression systems. An expression system based on autonomously replicating plasmids with the lipase expression cassette and an expression system based on multicopy integration of the lipase expression cassette.

A. Production of P. glumae lipase with autonomously replicating plasmids.

The plasmid pUR2730 (17) was used as the basis for the lipase expression plasmids. The plasmid pUR2730 consists of the GAL7 promoter, 2 mm sequences for replication in *S. cerevisiae*, the LEU2d gene for selection in *S. cerevisiae* and pBR322 sequences for replication and selection in *E. coli*.

The plasmid pUR6038 was used as the source for the lipase gene.

The following *S. cerevisiae* expression plasmids were constructed, encoding:

1. mature lipase preceded by the invertase signal sequence (pUR6801),
2. mature lipase preceded by a KEX2 cleavage site, a glycosylation site and the invertase signal sequence (pUR6802).

In order to obtain the above mentioned constructs, the routes followed were (FIG. 15; the used restriction recognition sites are marked with an asterisk):

ad 1 and 2.

a. The plasmid pUR2730 was digested with SacI and HindIII and the vectorfragment was isolated.

b. The plasmid pUR6038 was digested with EcoRV and HindIII and the fragment with the lipase gene was isolated.

c. Synthetic SacI-EcoRV DNA fragments were synthesized and constructed as described in example 3, consisting of the following sequences:

In the case of pUR6801:

---

I.
CATCACACAAACAAACAAAACAAAATGATGCTTTTGCAAGCCTTCCTTTTCC
TCGAGTAGTGTGTTTGTTTGTTTTGTTTTACTACGAAAACGTTCGGAAGGAAAAGG
TTTTGGCTGGTTTTGCAGCCAAAATATCTGCCGCGGACACATATGCAGCTACGAGAT
AAAACCGACCAAAACGTCGGTTTTATAGACGGCGCCTGTGTATACGTCGATGCTCTA

---

In the case of pUR6802:

---

II.
CATCACACAAACAAACAAAACAAAATGATGCTTTTGCAAGCCTTCCTTTTCC
TCGAGTAGTGTGTTTGTTTGTTTTGTTTTACTACGAAAACGTTCGGAAGGAAAAGG
TTTTGGCTGGTTTTGCAGCCAAAATATCTGCCTCCGGTACTAACGAAACTTCTGAT
AAAACCGACCAAAACGTCGGTTTTATAGACGGAGGCCATGATTGCTTTGAAGACTA
AAGAGAGAAGCTGAAGCTGCTGACACATATGCAGCTACGAGAT
TTCTCTCTTCGACTTCGACGACTGTGTATACGTCGATGCTCTA

--- d. The SacI-HindIII vector fragment, one of the SacI-EcoRV synthetic fragments (I) and the EcoRV-HindIII DNA fragment with the lipase gene were ligated. For the construction of pUR6801 this is shown in FIG. 15. (pUR6802 is constructed in the same way, using synthetic fragment II)

e. The ligation mixture was transformed to *E. coli*. From single colonies, after cultivation, the plasmid DNA was isolated and the correct plasmids, as judged by restriction enzyme analysis were selected and isolated in large amounts.

f. The plasmids pUR6801 and pUR6802 were transformed to *S. cerevisiae* strain SU10 (17) with the spheroplast procedure (18) using selection on the presence of the LEU2d geneproduct.

g. The transformants Were grown overnight in defined medium (0,68% Yeast Nitrogen Base w/o amino acids, 2% glucose, histidine and uracil), diluted 1:10 in induction medium (1% yeast extract, 2% bacto-peptone,.5% galactose) and grown for 40 hours.

h. The cells were isolated by centrifugation and cellextracts were prepared (19).

i. The cellextracts were analysed with SDS-gel electrophoresis (1) and blotted on nitrocellulose.

j. The nitrocellulose blots were incubated with lipase antibodies and subsequently with iodine-125 labelled protein-A followed by fluorography (FIG. 15a).

Figures 1, 15A:
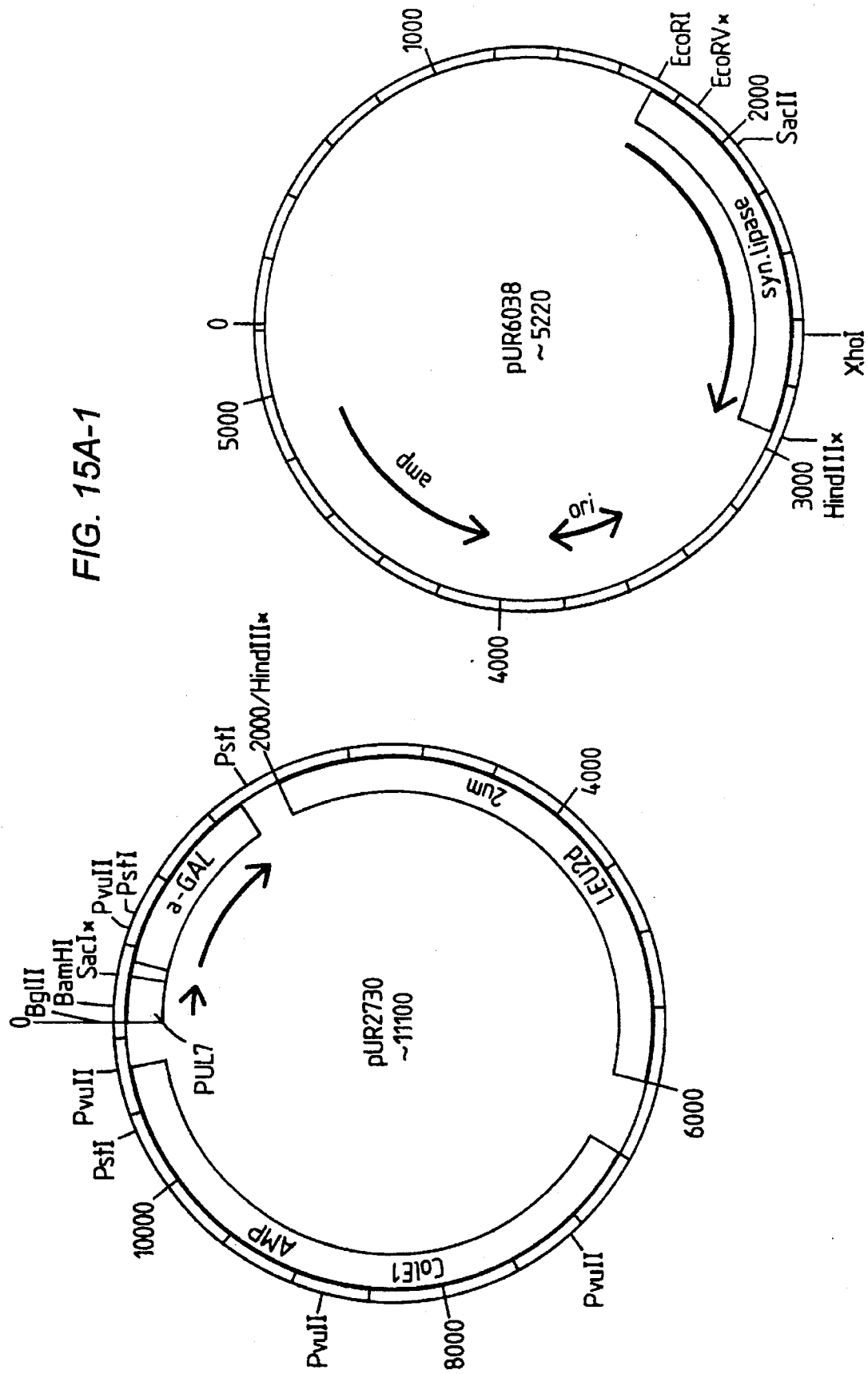
Figures 2, 15A:
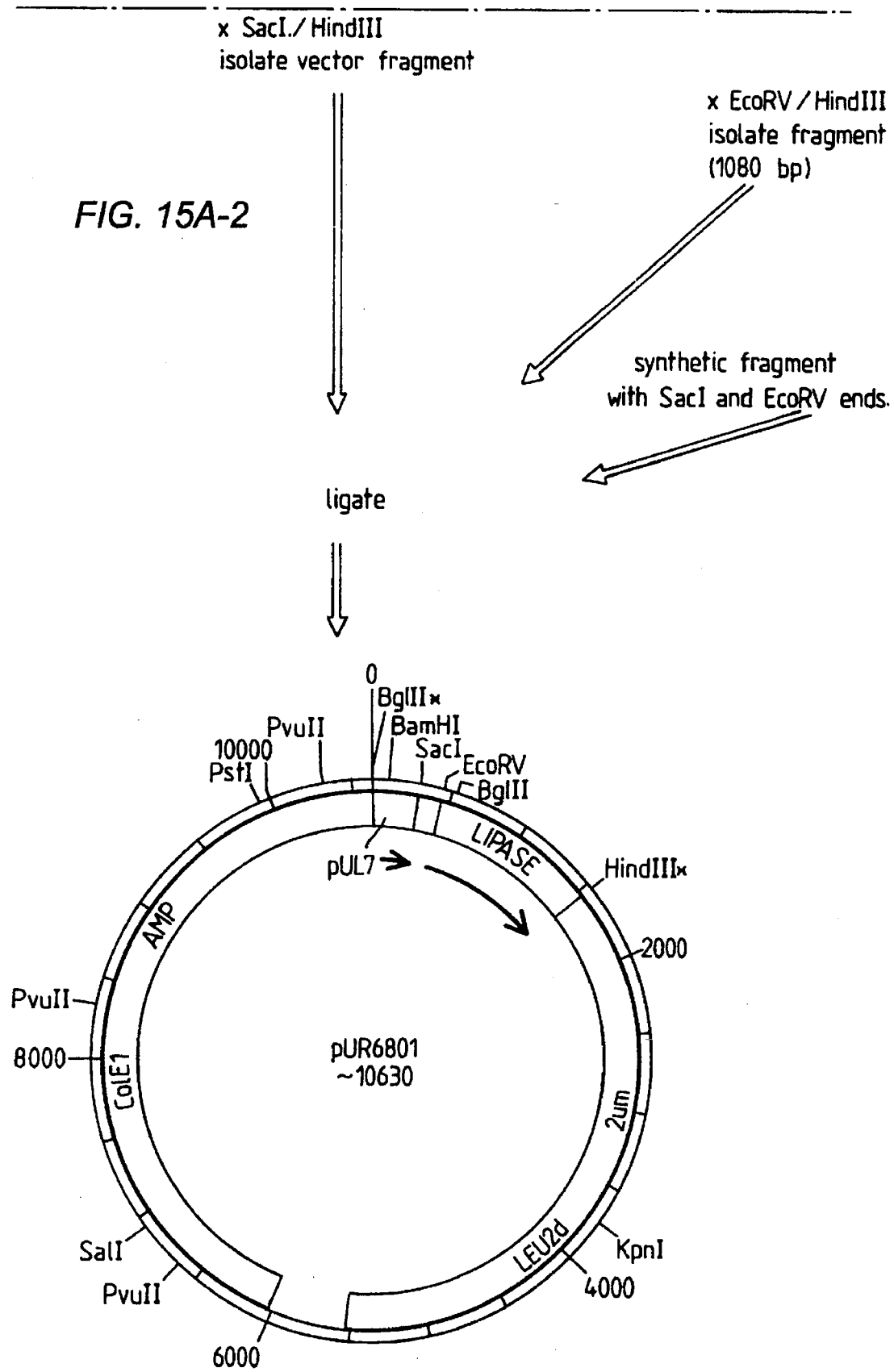

As shown in FIG. 15a, it clearly can be seen that SU10 with the plasmid pUR6801 produces the lipase enzym with the correct molecular weight as compared to lipase from *P. glumae*. Besides the correct protein also not processed and glycosylated lipase protein can be seen. The *P. glumae* lipase produced by *S. cerevisiae* is enzymatic active.

B. Production of *P. glumae* lipase by *S. cerevisiae* with multicopy integration.

Figure 15B:
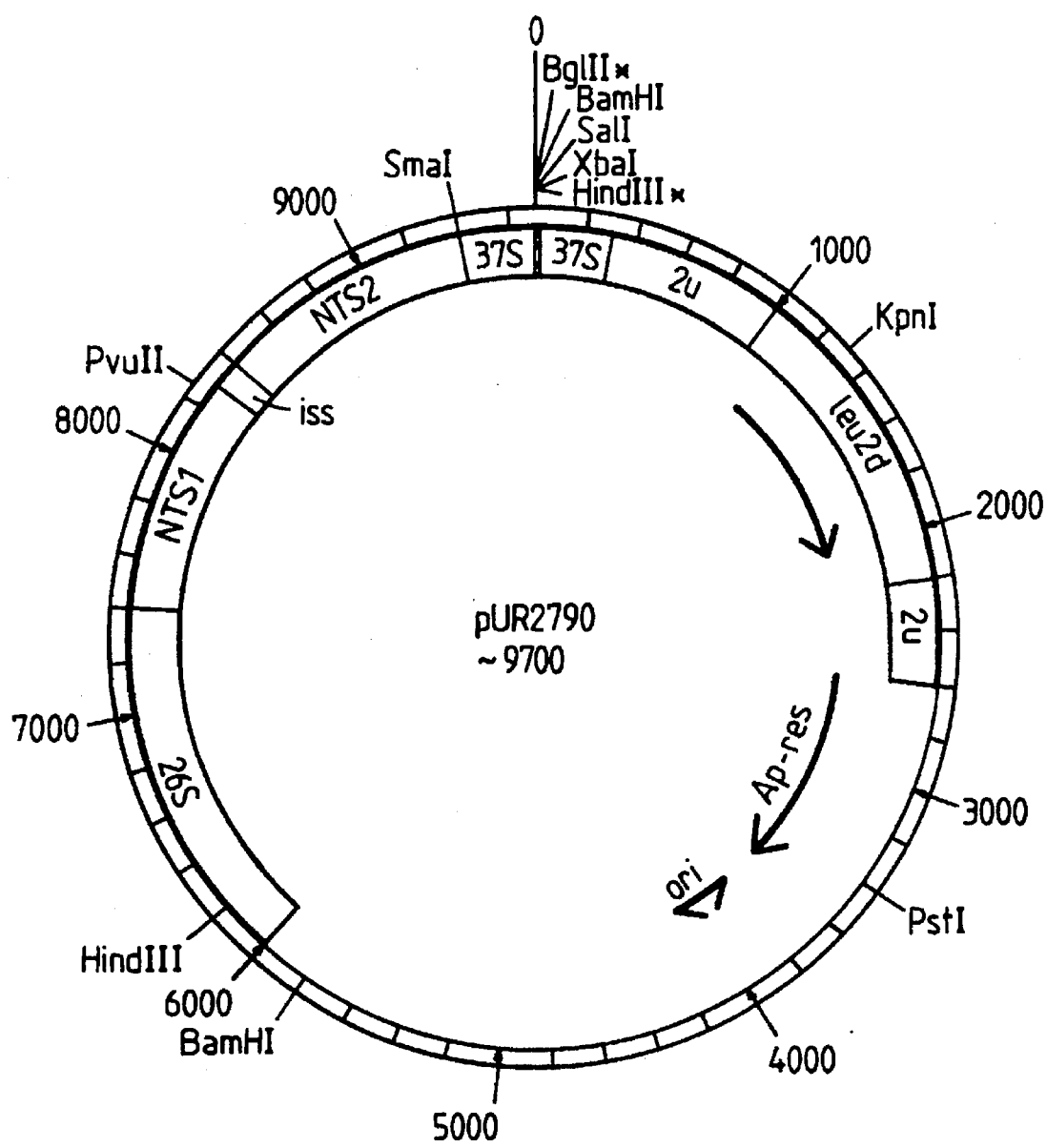
Figure 15C:
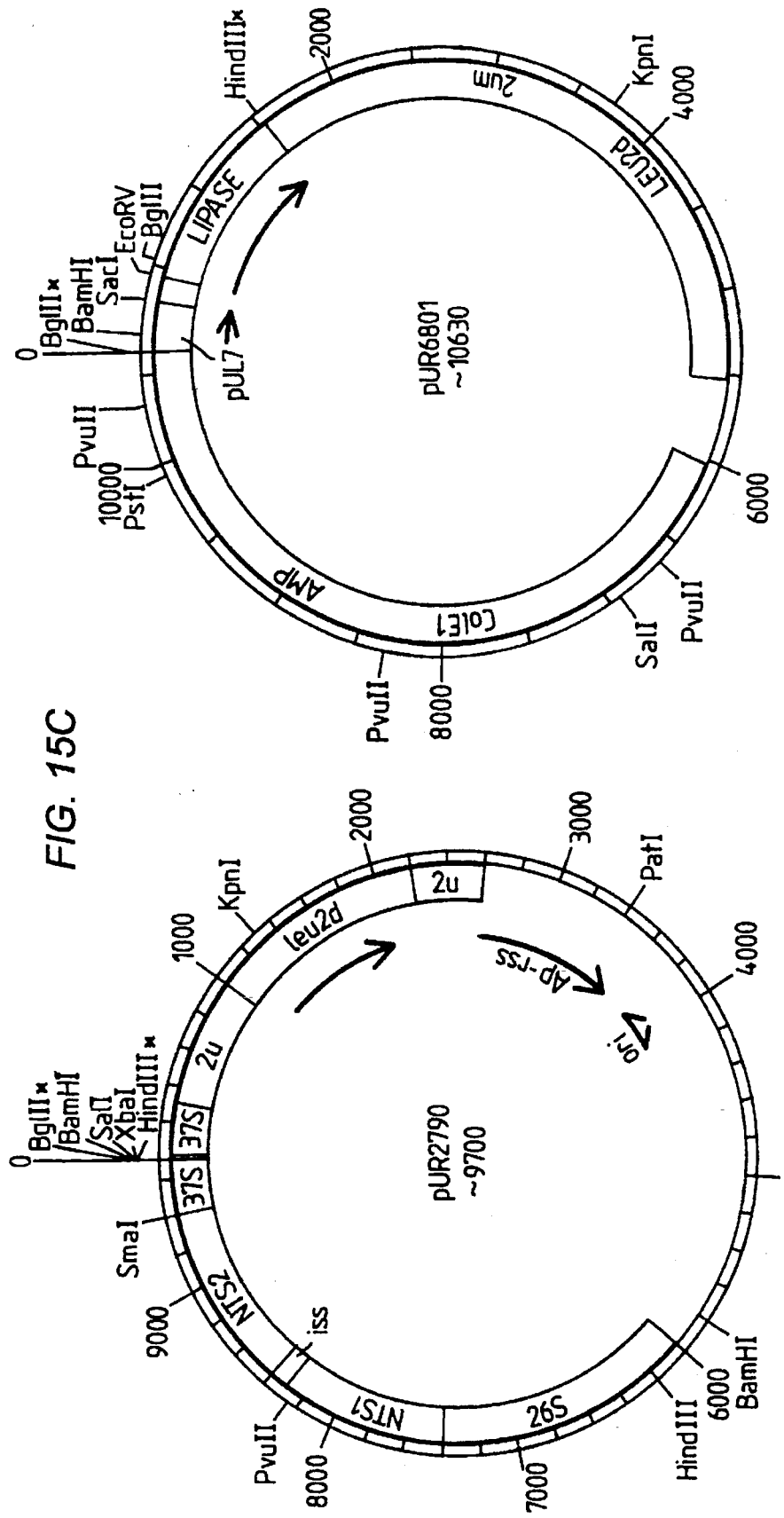
Figures 1, 15C:
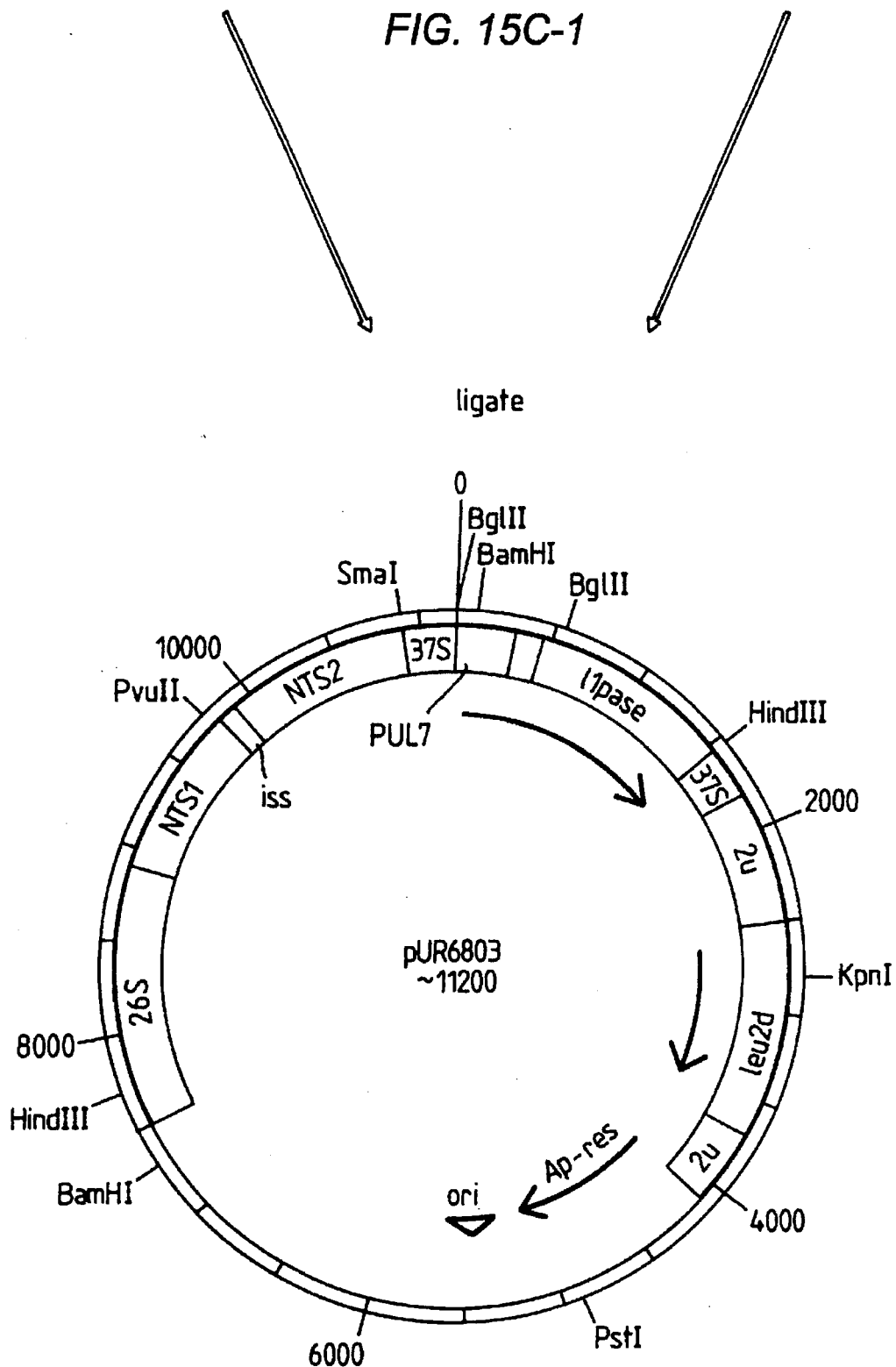

The multi-copy integration vector was derived from the plasmid pARES6 (19a) by replacing the 335 bp yeast RNA polymerase I promoter element with the 4.5 BglII B fragment of *S. cerevisiae* rDNA (19b). Also the 2 mm autonomously replicating sequence was removed and the BglII-HindIII DNA fragment with chloroplast DNA from *S. oligorhiza* was replaced by a polylinker DNA sequence. This resulted in plasmid pUR2790 from which a detailed picture is shown in FIG. 15b.

The essential sequences for multicopy integration in the yeast genome of pUR2790 are: 1. rDNA sequences for multicopy integration in the yeast genome, 2. the *S. cerevisiae* LEU2d gene (19c); this is the LEU2 gene with a deficient promoter.

Amongst others the following multicopy integration expression plasmids were constructed, encoding:

1. mature lipase preceded by the invertase signal sequence (pUR6803),
2. mature lipase preceded by a KEX2 cleavage site, a glycosylation site and the invertase signal sequence (pUR6804).

In order to obtain the above mentioned constructs, the routes followed were (FIG. 15c; the used restriction recognition sites are marked with an asterisk):

ad 1 and 2.

a. The plasmid pUR2790 was partially digested with HindIII. The linear plasmid was isolated and was digested to Completion with BglII and the HindIII-BglII vectorfragment was isolated by agarose gelelectrophoresis and electroelution.

b. The plasmid pUR6801 was digested partially with BglII and to completion with HindIII and the BglII-HindIII DNA fragment with the lipase gene was isolated (pUR6804 is constructed in the same way using plasmid pUR6802 instead of pUR6801).

c. The BglII-HindIII vectorfragment of pUR2790 and the BglII-HindIII fragment with the lipase gene were ligated (FIG. 15c), resulting in plasmid pUR6803.

d. The ligation mixture was transformed to *E. coli*. From single colonies, after cultivation, the plasmid DNA was isolated and the correct plasmids, pUR6803 and pUR6804, as judged by restriction enzyme analysis were selected and isolated in large amounts.

e. The plasmids pUR6803 and pUR6804 were transformed to *S. cerevisiae* strain YT6-2-1 L (19c) with the spheroplast procedure (18) using selection on the presence of the LEU2d geneproduct. The deficient promoter of the LEU2 gene is essential for multicopy integration of the plasmids in the yeast genome. The multicopy integration occurs at the rDNA locus of the yeast genome due to homologous recombination of the rDNA sequences of the plasmids and the rDNA sequences of the yeast genome.

In this way yeast strains have been obtained with a multicopy integration (up to 100 copies) of the plasmids pUR6803 and pUR6804 (including the lipase expression cassette) for the production of active *P. glumae* lipase. This multicopy integration system is stable even under non-selective conditions.

17. Overbeeke, N. et al., WO, 87/07641
18. Beggs J. D. Nature, (1978) vol. 275, p104–109
19. Verbakel et al., Gene, (1987) vol. 61, p207–215.
19a. Kempers-Veenstra, A. E. et al., EMBO J. (1984) vol. 3, 1377–1482.
19b. Szostak, J. W. et al., Plasmid, (1979) vol 2, 536–554.
19c. Erhart, E. et al., J. Bacteriology, (1983) vol 156, 625–633.

EXAMPLE 8

Expression of the synthetic lipase genes in *Hansenula polymorpha*.

Figure 16F:
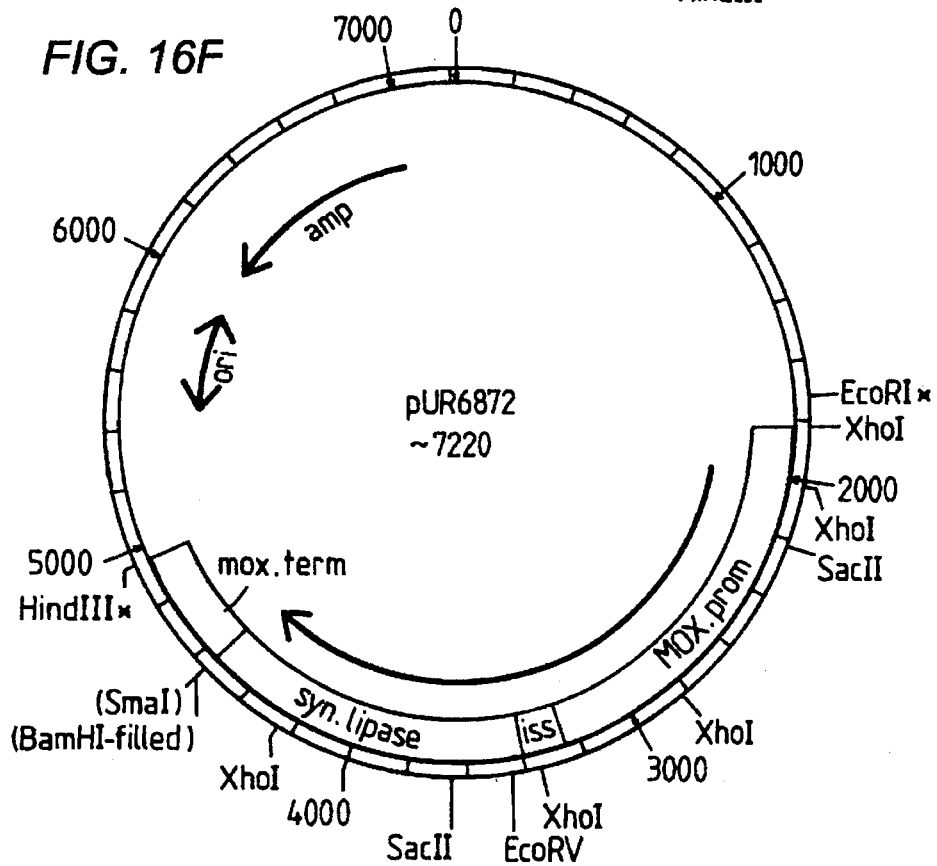
Figure 16G:
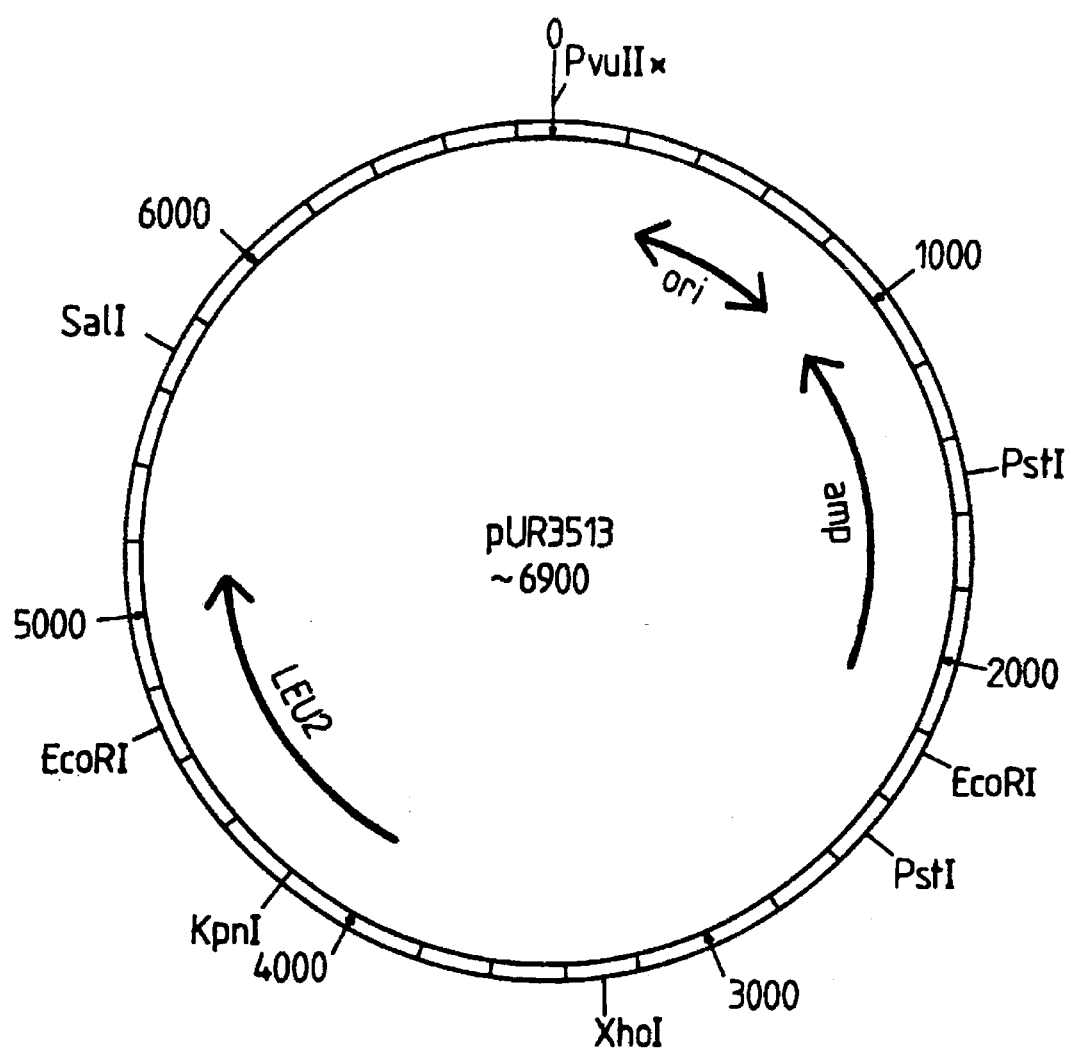
Figure 16H:
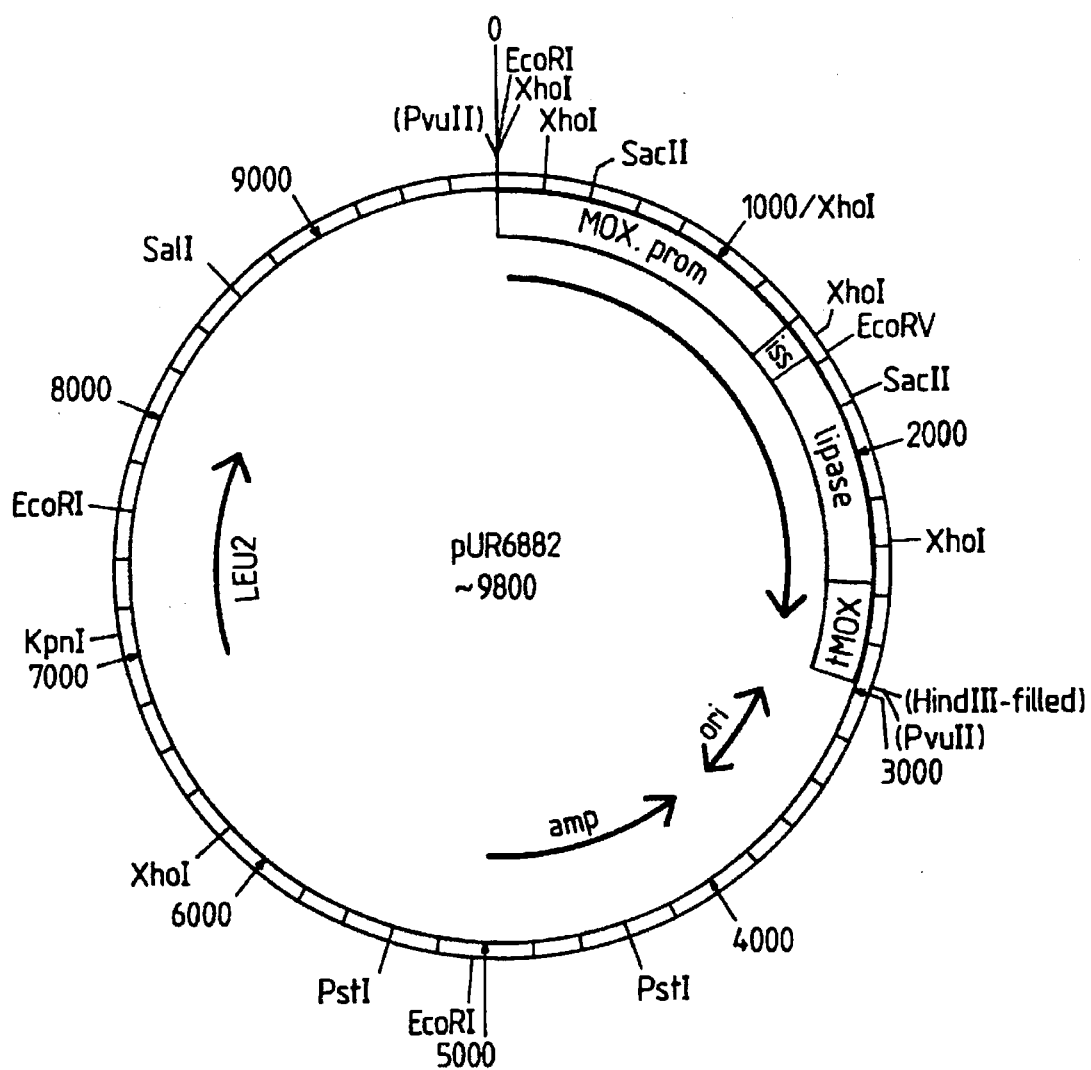

The synthetic lipase genes were integrated in the *H. polymorpha* genome using the following procedure (FIG. 16; in each figure of this example the used restriction recognition sites are marked with an asterisk; restriction recognition sites between brackets are removed due to the cloning procedure):

a. Plasmid pUR6038 (FIG. 16A) was digested to completion with the restriction enzymes EcoRI and EcoRV. After separation of the fragments by agarose gel electrophoresis the vector fragment was isolated as described in Example 2.

b. Several different .synthetic cassettes were assembled as described in Example 3. These cassettes encoded a number of amino acids necessary for a correct joining of the invertase signal sequence with different length of the pro-mature lipase gene. This was done to establish the most optimal construct with respect to expression, processing and export of the lipase enzyme. Furthermore these cassettes had EcoRI and EcoRV ends. typical examples are given in FIG. 16.

c. The assembled cassettes were ligated in the vector prepared under a.

d. The plasmids thus obtained (pUR6850, 6851 and 6852 FIG. 16B) were partially digested with the enzyme XhoI and the linear plasmid was isolated.

e. Plasmid pUR3501 (17, FIG. 16C) was partially digested with XhoI. After agarose gel electrophoresis a DNA fragment of approximately 1500 bp was isolated, containing the MOX promoter followed by the first amino acids of the invertase signal sequence (XhoI DNA fragment from position 0 to 1500 from pUR3501).

f. The 1.5 kb fragment of e. was ligated in the vector fragments as prepared in d resulting in plasmids pUR6860, 6861, 6862 FIG. 16D.

g. The ligation mixture was transformed to *E. coli*. From single colonies, after cultivation, the plasmid DNA was isolated and the correct plasmids, as judged by restriction enzyme analysis were selected and isolated in large amounts.

h. The correct plasmids obtained in step g. (eg. pUR6860, 6861, 6862 FIG. 16D) were digested to completion with BamHI, after which the sticky ends were filled in with Klenow polymerase (ex. 2). As the next step the linear plasmids were digested with EcoRI, and the filled in BamHI-EcoRI DNA fragments with the MOX promoter, invertase signal sequence and synthetic lipase of approximately 2.5 kb were isolated out of agarose gel.

i. Plasmid pUR3511 (the MOX terminator Cloned in the BamHI, HincII restriction sites of pEMBL9, FIG. 16E) was digested with SmaI and EcoRI, after which the vector was isolated out of an agarose gel.

j. The pUR3511 vector and the 2.5 kb fragments were ligated and cloned in *E. coli*. In the constructs obtained, the lipase gene is followed by the MOX transcription terminator. Typical examples of these constructs are pUR6870, 6871 and 6872 (FIG. 16F).

k. These plasmids were digested with EcoRI and HindIII, after which the fragments of approximately 3 kb. were isolated from an agarose gel. The sticky ends were filled in with Klenow polymerase.

l. Plasmid pUR3513; this is plasmid yEP13 (20) from which the 2 mm sequences have been deleted by a SalI digestion (FIG. 16G) was digested with PvuII.

m. The linear plasmid pUR3513 and the fragments obtained in k. were ligated to obtain the final constructs among which pUR6880, 6881 and 6882 (FIG. 16h).

Introduction of the expression cassettes in the *H. polymorpha* genome.

Transformation of plasmid DNA to the Hansenula cells can be performed as described by (17, 20a, 20b).

Analysis of the integrants can be performed using the Southern blot procedure (1).

20. Broach, J. et al., Gene (1979) vol 8, 121–133.
20a. Gleeson et al., Journal of General Microbiology (1986), vol 132, 3459–3465.
20b. Roggenkamp et al., Mol. Gen. Genet. (1986), vol 202, 302–308.

EXAMPLE 9

Expression of synthetic lipase genes in Aspergillus.

1. Construction of expression plasmids containing the gpdA promoter.

Figure 17:
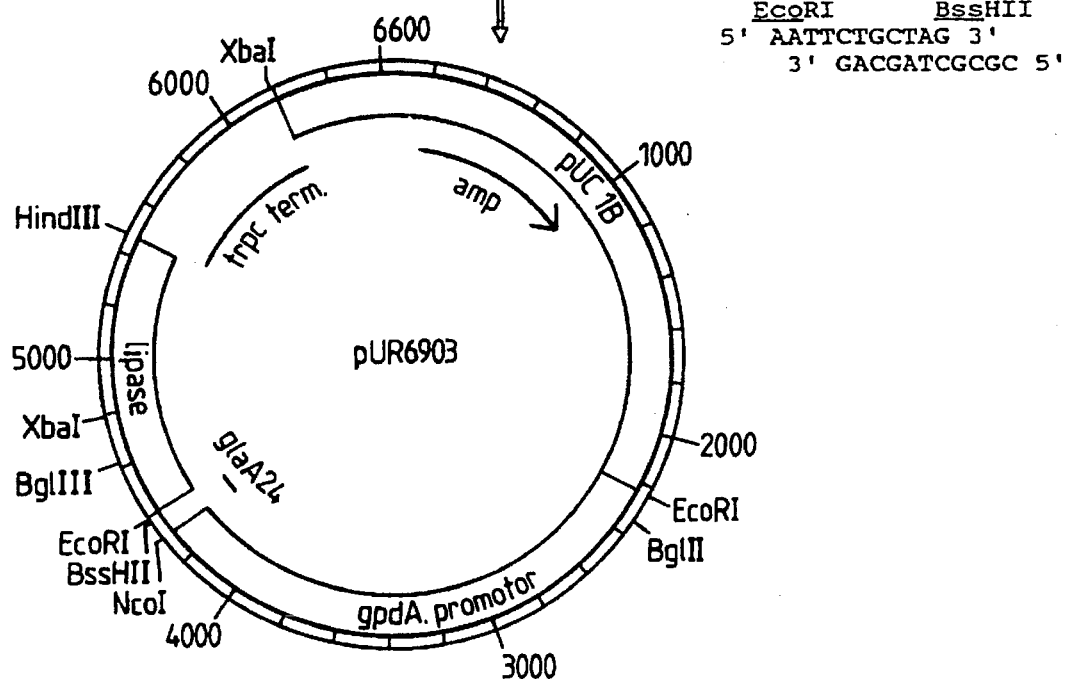
Figure 17A:
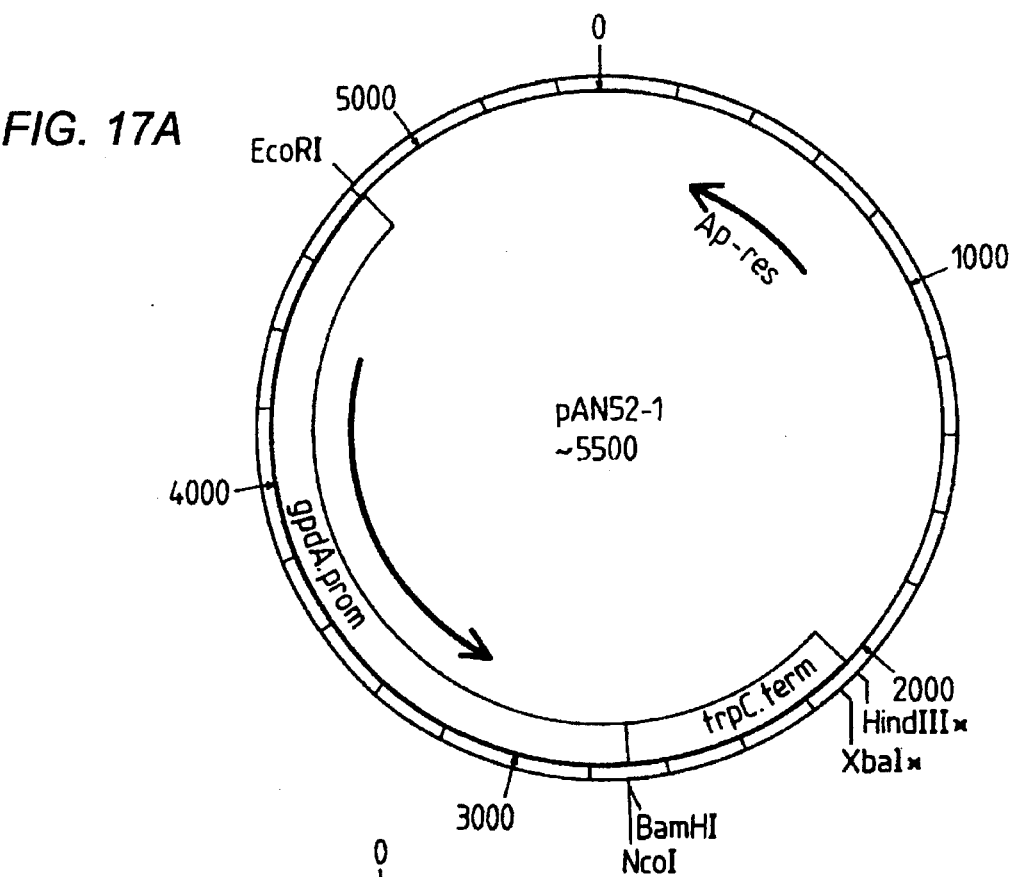
Figure 17B:
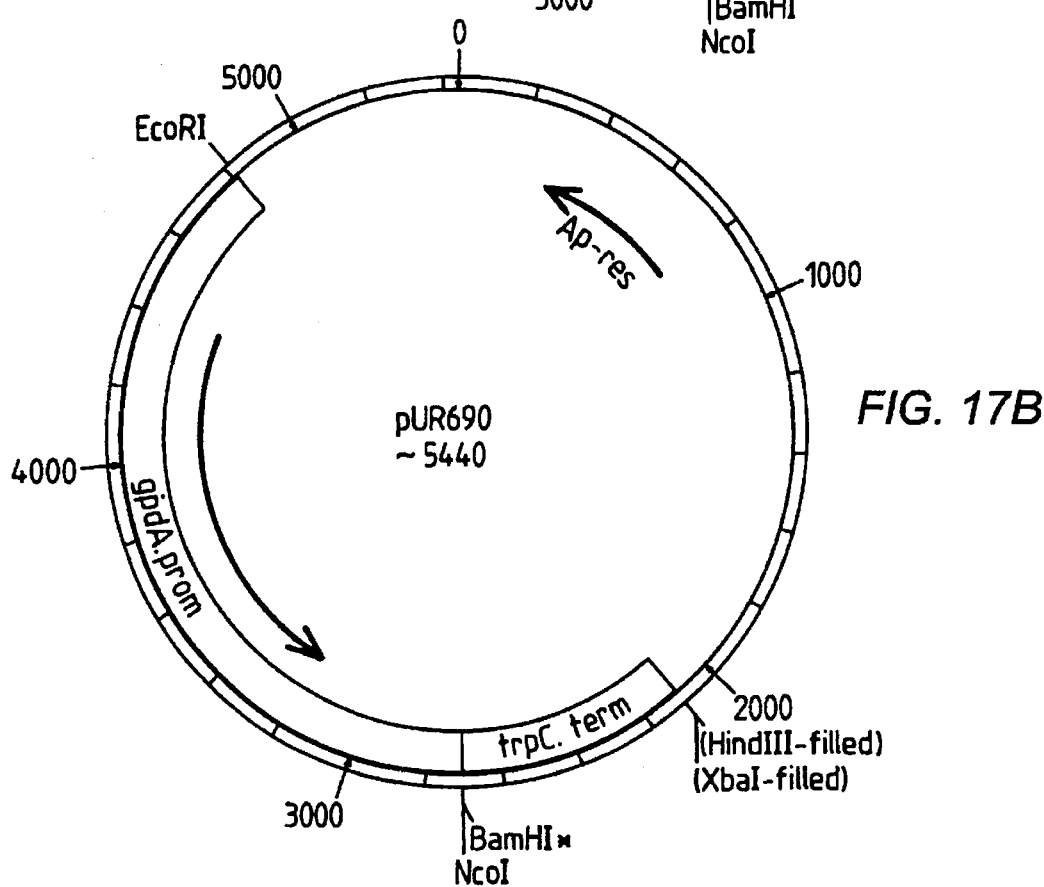
Figure 17C:
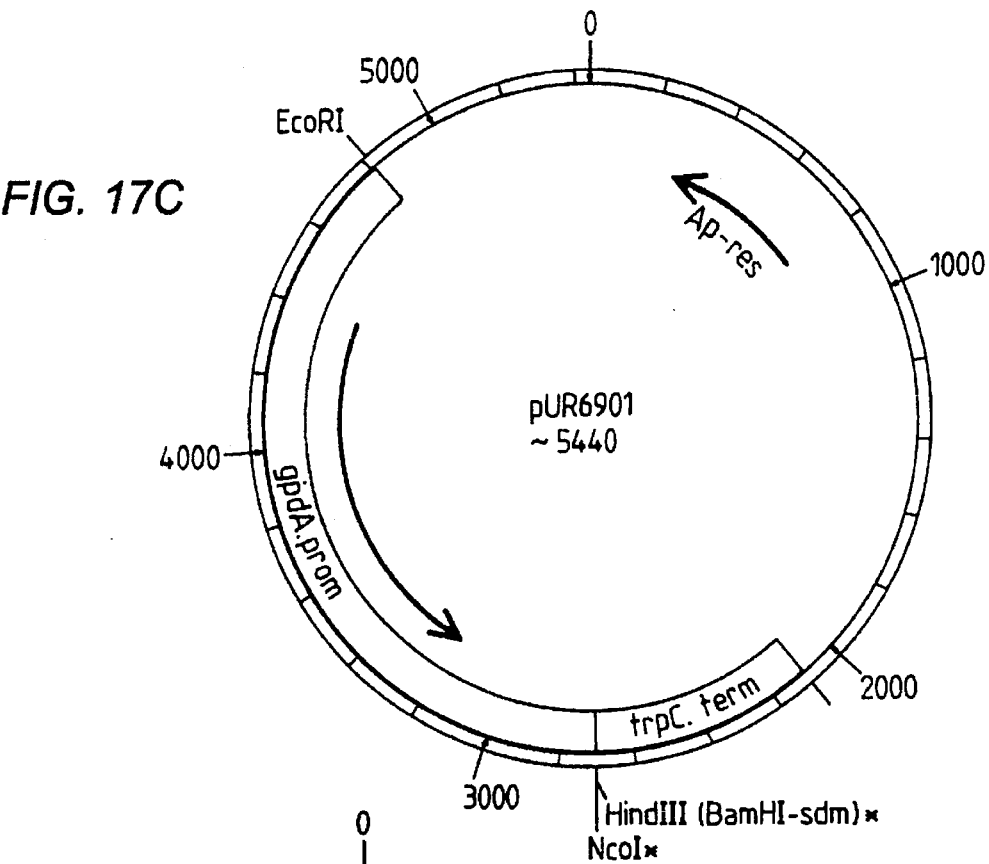
Figure 17D:
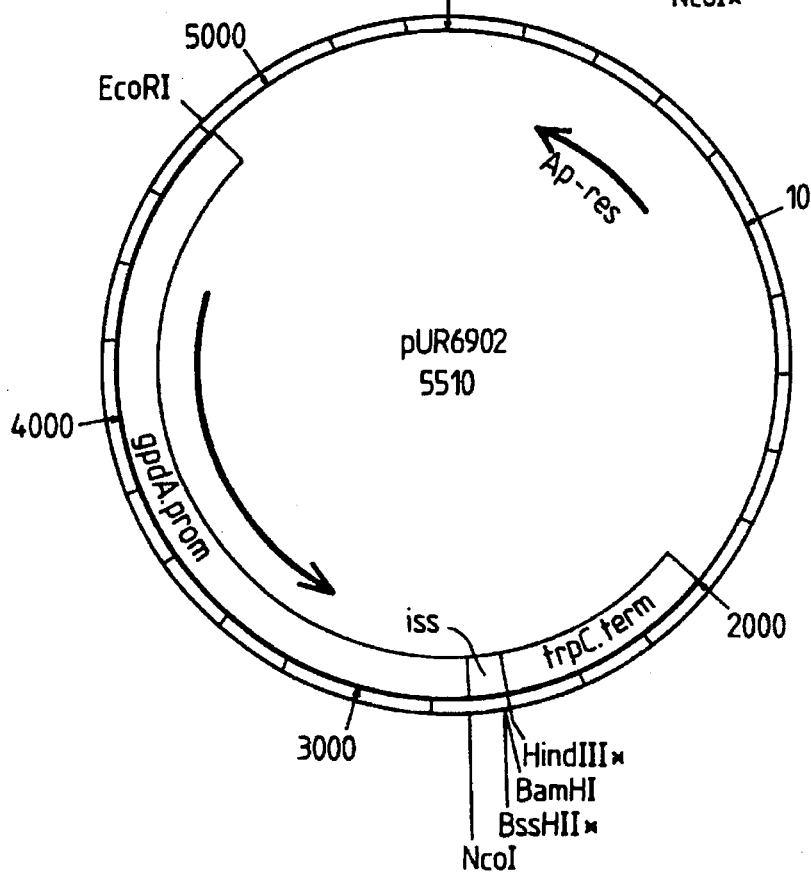

Plasmid pAN52-1 (21, FIG. 17a) containing the constitutive gpdA promoter (22) and the trpC transcription terminator (23) of *Aspergillus nidulans*, was used as the starting material for the construction of the Aspergillus expression plasmids (FIG. 17; in all the figures the used restriction recognition sites are marked with an asterisk; if a restriction recognition site has been removed it is placed between brackets).

a. pAN52-1 (FIG. 17a) was digested with XbaI and HindIII. After filling in the sticky ends with Klenow polymerase (1) the vector was religated. In this a XbaI/HindIII fragment of ~60 bp was deleted, the HindIII site was removed and pUR6900 (FIG. 17b) was obtained.

b. As a next step the BamHI site between the promoter and the terminator was removed, and a HindIII site was introduced. This was done via site-directed mutagenesis (SDM) as described by Kunkel (24) and resulted in plasmid pUR6901 (FIG. 17c). The only changes in nucleotide sequence are as follows:

| pUR6900 | BamHI |
| | ACCATGGATCC |
| | NcoI |
| pUR6901 | HindIII |
| | ACCATGGAAGCTTGAGATCC |
| | NcoI | c. Based on the sequence as described by Boel (25), a synthetic fragment encoding the first 24 aminoacids of the glucoamylase signal sequence was designed and assembled as described in Example 3. For cloning convenience a NcoI site was introduced by changing the second codon (TCG) encoding aminoacid serine into GGC, encoding glycine. It is obvious that it is possible to restore the correct sequence via site-directed mutagenesis at a later stage of the construction route. The sequence of the used fragment, having NcoI and HindIII sticky ends, is given in FIG. 17.

d. pUR6901 (FIG. 17c) was digested with NcoI and HindIII. After agarose gel electrophoresis the vector was isolated out of the gel. The synthetic fragment described above was ligated in the vector and in this way the plasmid pUR6902 (FIG. 17d) was obtained.

Figure 14:
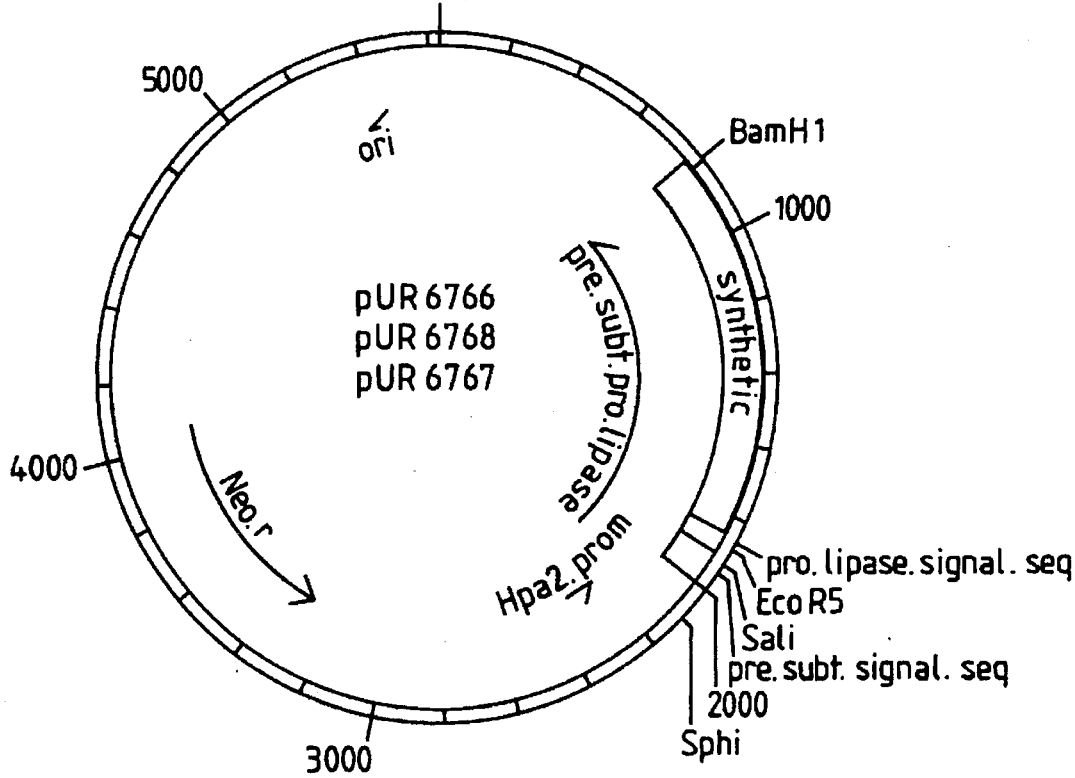
Figure 17E:
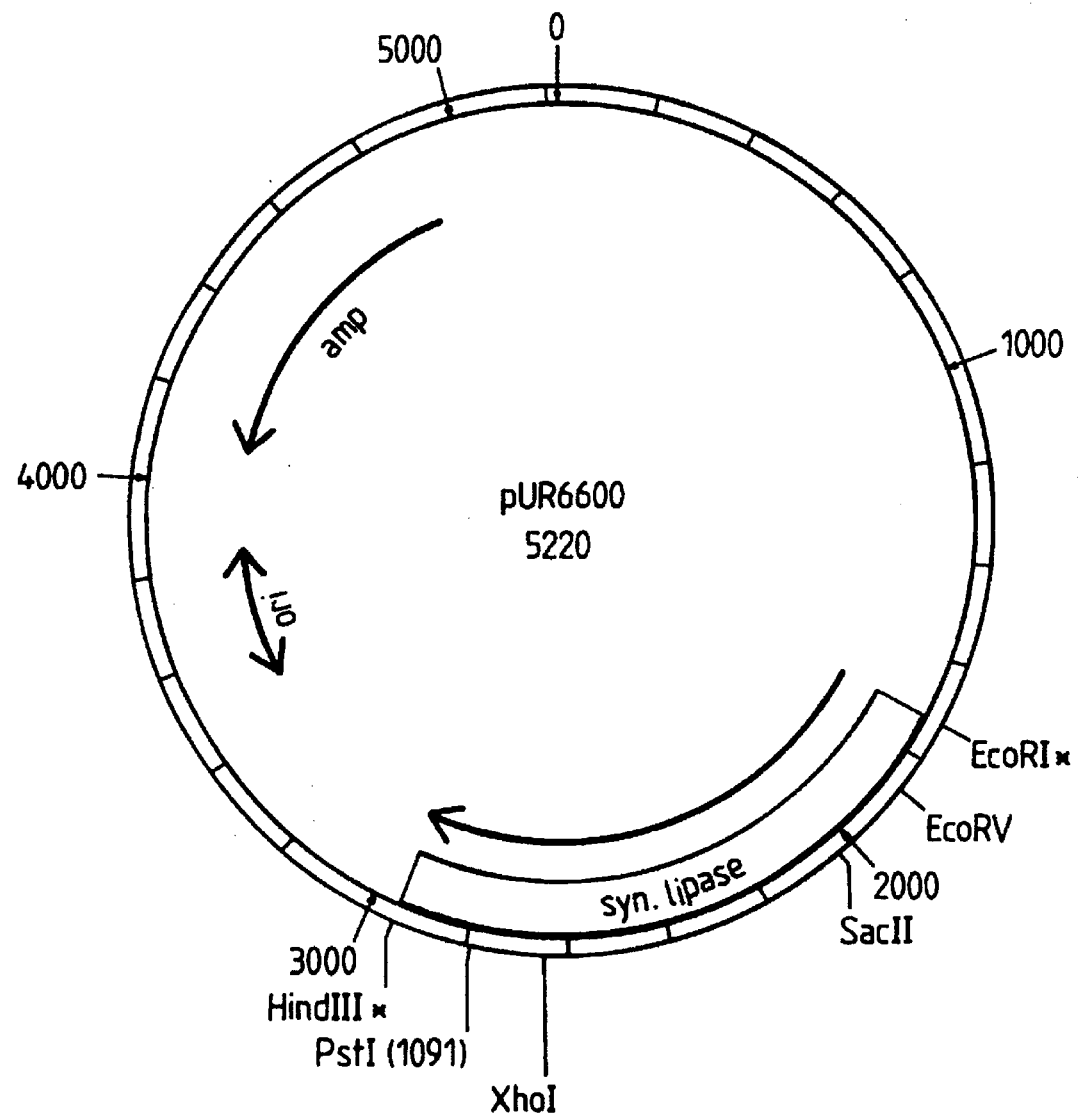
Figure 17F:
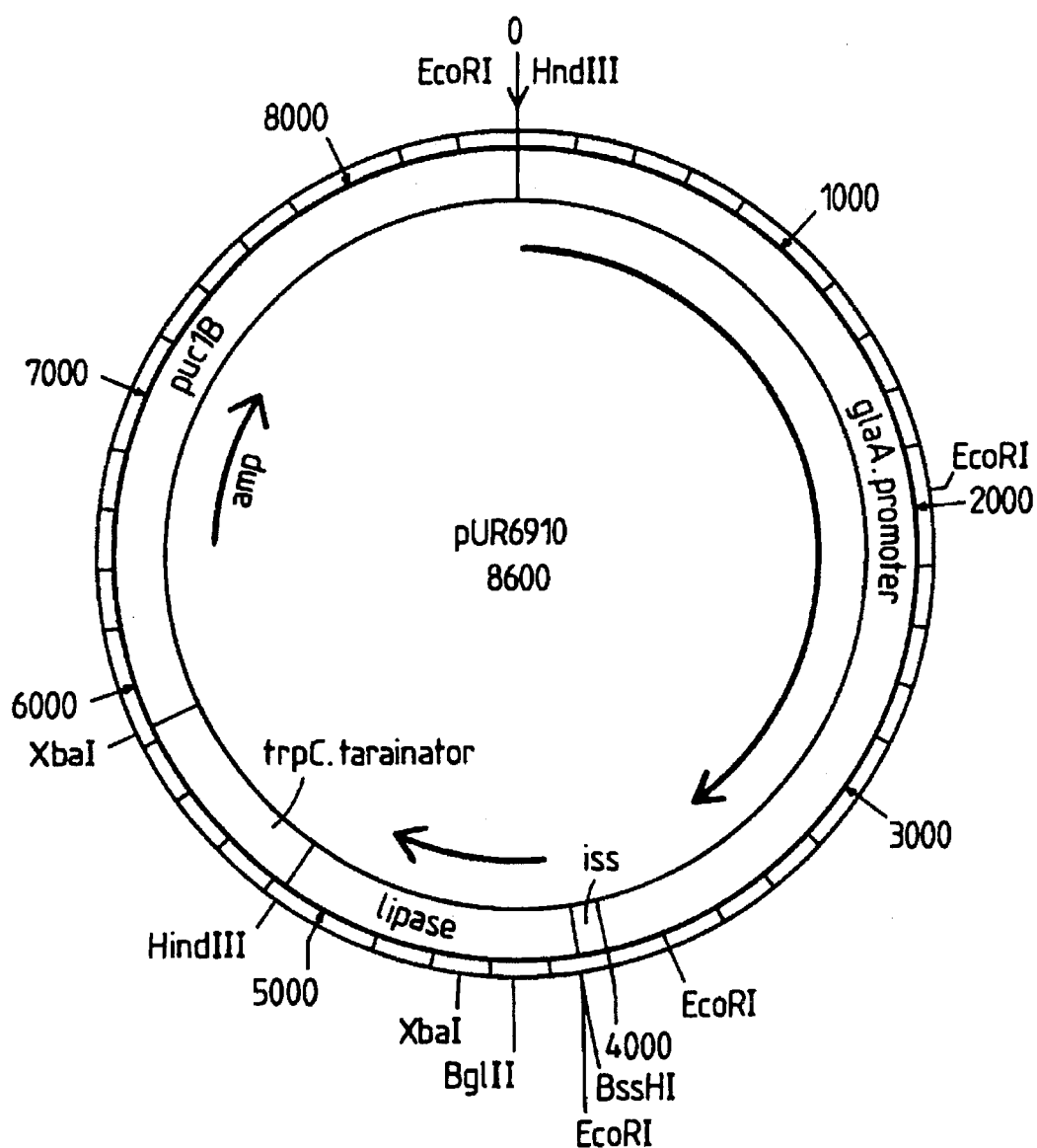

For integration of the synthetic lipase gene into the Aspergillus genome, the following constructions were made:

a. Expression plasmid pUR6902 (FIG. 17d), containing the constitutive gpdA promoter, the glaA24 signal sequence and the trp terminator, was digested to completion with BssHII and HindIII. After electrophoresis, the vector was isolated out of the agarose gel.

b. pUR6600 (FIG. 17e, see also FIG. 5) was digested with EcoRI and HindIII, after which the fragments were separated via agarose gel electrophoresis. A ~1090 bp fragment, containing the lipase gene, was isolated out of gel.

c. Two oligomers (see FIG. 17 for sequences) were ligated to the EcoRI sticky end of this fragment to obtain a BssHII sticky end.

d. The BssHII-HindIII fragment thus obtained, was ligated to the pUR6902 (FIG. 17d) vector, which resulted in pUR6903 (FIG. 17).

e. Via site directed mutagenesis (24), With synthetic oligomers, the lipase gene was joined to the gene fragment encoding (part of) the glaA signal sequence in different ways. This was done to establish the most optimal construct with respect to expression, processing and export of the lipase enzyme. A few of these constructs are described in more detail (FIG. 14).

1. pUR6905, containing a gene fragment coding for the first 18 amino acids of the glaA signal sequence followed by a pre-lipase gene fragment, encoding amino acid −13 to 319.

2. pUR6906, containing a gene fragment coding for the first 24 amino acids of the glaA signal sequence followed by a pre-lipase gene fragment (see 1).

3. pUR6907, like pUR6905 with mature lipase gene.

4. pUR6908, like pUR6906 with mature lipase gene.

In the constructs pUR6906 and pUR6908 the BssHII site remained present after the connection of the glaA signal sequence with the pre-lipase. EcoRI site, between the lipase gene and the glaA signal sequence was deleted in all four constructs.

In the route presented above we chose to use (part of) the gluco-amylase signal sequence as an export signal for the intra-cellular produced *glumae* lipase. It is obvious that other signal sequences could lead to the same results.

Another option would be to use not only the signal sequence of an exported (homologous) protein, but also (part of) the mature protein (eg gluco-amylase or Lipolase (trade name, NOVO)) and fuse this with the glumae lipase. When following this route it might be necessary to introduce a (unique) cleavage site (eg. KEX2, factor X or a Methionine (in combination with a mutation of Methionine at position 263 of the mature lipase) between the exported protein and the mature lipase. In this way it should be possible to release the mature lipase from the exported chimeric protein after its production.

Finally it might be possible to produce genes encoding chemaric lipases, starting with the Lipolase N-terminus followed by different Lipolase and glumae lipase fragments, resulting in the production and excretion of an optimized 2. Constructions containing the glaA-promoter.

a. Based on the restriction map and the nucleotide sequence as published by Boel (25) and Nunberg (25a), a synthetic DNA probe (23 bp) was prepared as described in example 1. The sequence of this synthetic probe was 5' TGCTGAGGTGTAATGATGCTGGG 3'. This probe was used in a standard cloning procedures as described in (1) in order to isolate the glucoamylase gene (glaA) of A. niger.

b. With this probe an *A. niger* gene bank made in phage lambda was screened for clones containing the glucoamylase promoter and (part of) the coding region.

c. From one of these clones a HindIII/BssHII fragment of _4.1 kb, containing the promoter-region of the glaA gene and the 5' part of the coding region till amino acid 24, was isolated out of agarose gel after digestion with said enzymes and gel electrophoresis.

d. By ligation of two oligomers (see below) to the HindIII sticky end, an EcoRI sticky end was introduced.

| EcoRI | AATTCTCTAGA | HindIII |
| | GAGTCTTGCA | |

In this way an EcoRI/BssHII fragment was obtained.

e. After complete digestion of pUR6906 and pUR6908 with EcoRI and BssHII, followed by gel-electrophoresis, the linear plasmids were isolated.

f. These vectors were ligated with the DNA fragment mentioned above (d.), and in this way pUR6910 and pUR6912 were obtained.

g. Again the lipase gene was joined in different ways to the glucoamylase signal sequence via site directed mutagenesis. This was done in essentially the same was as described above, using the same oligomers, and result in pUR6909 and pUR6911 respectively. The plasmids pUR6909 to pUR6912 differ from pUR6905 and pUR6908 in that the gpdA promoter is replaced by the glaA promoter.

3. Introduction of the expression cassette into the Aspergillus genome.

The introduction of the expression cassette into the Aspergillus genome has been realized in two different ways.

1. Via co-transformation: for this method the protocol as described in 27 was used.

2. Via transformation with expression cassettes in which a positive selection marker had been introduced.

Used selection marker were: - amdS (ex *A. nidulans*, 26) or - purG (ex *A. oryzae*, 27).

They were obtained as EcoRI fragment from pGW325 (Wernars, pHD thesis (1986) Agricultural University Wageningen, NL) and BamHI fragment from pAO4-2 (27), respectively.

Introduction of the amdS marker could be accomplished by (partially) digesting the above mentioned plasmids with EcoRI or HindIII, and ligating them in the presence of the EcoRI or (via adaptation with EcoRI-HindIII linkers) HindIII selection marker fragment. In the case of pyrG the introduction could be accomplished by (partially digesting the above mentioned plasmids with EcoRI or HindIII, and ligating them in the presence of a, with EcoRI-BamHI adapters created EcoRI selection marker fragment or; with HindIII-BamHI adapters created HindIII selection marker fragment. The correct plasmids, where the marker genes were ligated in the EcoRI or HindIII site at position _2200 of the plasmids pUR6915 oa., were isolated in large amounts and used for transformation experiments.

Transformation of plasmid DNA to *A. niger, A. awamori* and *A. oryze* (ao.) is performed as described by Wernars et al (28) and Kelly (29).

Analysis of the integrants can be performed with Southern blot procedure (1).

21. Punt P. J. et al, Gene 56 (1987) pp 117–124.
22. Punt P. J. et al, Gene 69 (1988) pp 49–57.
23. Mullaney E. J. et al, Mol Gen Genet 199 (1985) pp 37–45.
24. Kunkel T. A., Proc Nat Acad Sci USA 82 (1985) 488–492.
25. Boel E. et al, EMBO Journal 3 (1984) pp 1581–1585.
25a. Nunberg J. H. Mol Cell Biol 4 (1984) 2306–2315.
26. Hynes, Mol Cell Biol 3 (1983) 1430–1439.
27. De Ruiter-Jacobs et al, Curr Genet 16 (1989) 159–163.
28. Wernars et al, Current Genetics 9 (1985) 361–368.
29. Kelly et al, EMBO J 4 (1985) 475–479.

EXAMPLE 10

Expression of the *Ps. glumae* lipase gene in other Gram-negative bacteria.

In order to employ other Gram-negative bacteria for the efficient production of the *P. glumae* lipase, other plasmids have been constructed, using the inducible tac promoter and lac repressor from *E. coli* located on the broad host range expression plasmid pMMB67EH (30). For obvious reasons any other broad host-range plasmid comprising a regualtable promoter that functions in the species of interest would have been equally suitable.

A. Construction of pUR6500.

A BamHI fragment with a length of ~1.5 kb, comprising the gene that confers resistance to kanamycin, was taken from pCP13 (31), treated with Klenow polymerase to generate blunt ends and ligated into the blunt ended PvuI site of pMMB67EH, resulting in pUR6500 (FIG. 18).

B. Construction of pUR6502.

pUR6002 (ex *E. coli* KA817) was digested to completion with ClaI and EcoRI, after which a ~1750 bp fragment (comprising nearly the entire lipase gene and the 3' flanking region) could be isolated. This fragment was ligated to synthetic DNA linker molecules, having the following sequence:

| | | |
|---|---|---|
| EcoRI | AAT TCG ACG TAA CCG ATA ACG TAG -<br>GC TGC ATT GGC TAT TGC ATC -<br>- GAG ATA AAC ATG GTC AGA T<br>- CTC TAT TTG TAC CAG TCT AGC | ClaI |

After ligation, the fragments were redigested with EcoRI.

pUR6500 was digested to completion with EcoRI, after which it was ligated with the EcoRI fragment (~1780 bp, described above). After transforming *E. coli* HB101 (1) with the ligation mixture the obtained colonies were screened for the desired plasmid. Since the fragment could be inserted in two different orientations, the correct orientation (with respect to the tac promoter) had to be selected. For this purpose, the plasmids, containing the EcoRI fragment, were digested with BamHI. A construct bearing the EcoRI fragment in the desired orientation behind the tac promoter was designated pUR6502 (FIG. 19).

C. Construction of pUR6522

1. Plasmid pUR6006 (described in Example 1) was digested to completion with the restriction enzymes EcoRI and SalI, after which a DNA fragment of ~5 kb was isolated.
2. Plasmid pUR6502 was digested to completion with the restriction enzymes EcoRI and SalI, after which a DNA fragment of ~570 bp was isolated.
3. The fragments obtained in steps 1 and 2 were ligated and redigested with EcoRI after which a fragment of ~5.6 kb was isolated.
4. The ~5.6 kb fragment was ligated in vector pUR6500 digested with EcoRI. After transforming *E. coli* HB101 with the ligation mixture the obtained colonies were screened for the desired plasmid. Again the EcoRI fragment could have two different orientations, and again digestion with BamHI enabled us to select the construct with the EcoRI fragment in the proper orientation with respect to the tac promoter.

In this way we obtained pUR6522 (FIG. 20).

D. Transformation of *E. coli* S17-1 and *Ps. aeruginosa.*

Plasmids pUR6502, pUR6522 as Well as pUR6500 (as a negative control) were introduced separately into *E. coli* S17-1 and *Ps. aeruginosa* PAO25 (ref 32) via transformation of competent cells using the CaCl2 method described for *E. coli* in Maniatis et al (1).

E. Transformation of *Pseudomonas putida.*

Plasmids pUR6502, pUR6522 as well as pUR6500 (as a negative control) were introduced into *Ps. putida* WCS358 (ref 33) by biparental conjugations with *E. coli* S17-1 containing one of the mentioned plasmids.

F. Induction experiments.

Upon growing *E. coli* HB101(pUR6502) and *Ps. aeruginosa* PAO25(pUR6502) in LB-medium supplemented with Km (25 mg/ml and 100 mg/ml rep.) and in the presence of 0.2 mM IPTG (inducer of the tac promoter), no lipase activity was found in the culture broth. Upon disrupting the cells using a French press and storing the cell debris for 16 hours at 4 deg C., lipase activity could be demonstrated. The presence of intact lipase was confirmed by Western blot analysis of the cell debris (FIG. 21).

Upon growing *Ps. putida* WCS358(pUR6502) and (pUR6522) on BYPO plates with and without IPTG we found a surprising result. It appeared that *Ps. putida* WCS358 containing pUR6522 produced significant amounts of lipase (demonstrated by the large halo formation), whereas the first-mentioned produced hardly any lipase (FIG. 22). This finding strongly indicates the presence of a specific "helper-function" for lipase, encoded by the 3'-region of the lipase gene extending beyond the BamHI site. This "helper-function" seems to be involved in a proper and/or optimal production of extracellular active lipase.

REFERENCES

30. Fruste P. et al, Gene 48 (1986) 119–131.
31. Darzins et al, J Bact 159 (1984) 9–18.
32. Haas et al, Mol Gen Genet 144 (1976) 243–251.
33. Geels et al, Phytopath Z 108 (1983) 193–206 & 207–214.

EXAMPLE 11

Determination of the improved proteolytic resistance of modified lipase.

Several mutations were introduced in the *P. glumae* lipase gene (as described in example 5), resulting in amino acid Changes around the proteolytic cleavage site (described in example 10), in order to improve the stability of the lipase in the presence of detergent proteases. The benefit of the mutations was established as follows:

Modified lipase was produced by fed batch fermentation and isolated via cell removal, concentration, ethanol extraction and DEAE-cellulose anion exchange.

The lipase variant was dissolved in a concentration of 5 mg/l in 5 g/l detergent base powder containing sodiumtriphosphate and 3 mM calcium chloride, to which Savinase (TM) was added to a concentration of 20 GU/ml, whereafter residual lipase activity was followed with time, keeping the temperature at 30° C.

FIG. 23 shows the results for the lipases produced by the transconjugants PGL6 and PGL24, in which Val150 is changed to Asp and His154 to Pro respectively. These results indicate a significantly reduced susceptibility to proteolytic attack.

FIG. 24 shows the results for the lipase variants PGL27, 33 and 36 in which Ser153 and/or His154 are changed to Arg. It is clear that the replacement by these, at pH 9–10 positively charged, amino acids results in significantly improved stability.

FIG. 25 exemplifies that combinations of two mutations lead to further improved protease compatibility: In PGL24 (H154P) a new primary cleavage site was determined between residues 149 and 150. PGL56.combines H154P with V150P, and is shown to be improved when compared with PGL24. PGL57 combines the proline introduction with an increased (local) positive charge (H154P+S151R), and a comparable improvement is evidenced.

EXAMPLE 12

Improvement of the resistance of *P. glumae* lipase against oxidative degradation by replacement of its single methionine.

Decrease of lipase activity was followed in time during an incubation in the presence of hydrogen peroxide (3% H2O2, 60 lipase units/ml, 0.25% dodecylbenzene sulfonate, 50 mM borate pH 9).

Values were corrected for activity loss in the absence of peroxide and results were plotted in FIG. 26.

It is readily seen that the modified enzyme PGL63 (mutation Met 254 Ile) has a significantly improved stability under these conditions when compared with the original enzyme. This modification is important not only for increasing the stability of the lipase under conditions of actual wash wash systems and liquid detergents but also to make chimeric proteins in which a methionine residue can be introduced as the last aminoacid residue preceding the first aminoacid residue of the mature lipase (see Example 9).

EXAMPLE 13

Determination of site of cleavage in lipase by subtilisin.

In order to identify useful mutations for introduction into the aminoacid sequence of lipase enzymes, the site of primary cleavage of the lipase polypeptide under the action of subtilisin can be determined as follows. The details refer primarily to work carried out with the lipase of *Pseudomonas glumae,* and can be modified for other lipases.

*Ps. glumae* lipase was isolated from concentrated fermentation broth by Phenylsepharose (TM—Pharmacia) hydrophobic interaction chromatography, followed by acetone extraction and gel-permeation chromatography (Sephacryl-200, Pharmacia). The enzyme preparation obtained was essentially pure as judged by specific activity, UV absorption and presence of only one band at approx 34 kD in SDS polyacrylamide gel electrophoresis.

The lipase (5 mg/ml) was digested at 30 deg C. in a solution of Savinase (TM—Novo subtilisin), dodecylbenzene sulphonate 1 g/l, sodium triphosphate 0.7 g/l, sodium sulphate 0.7 g/l, sodium silicate 0.2 g/l and sodium perborate 0.7 g/l (pH 9.5). (A GU is a standard unit of protease activity which during 15 mins incubation at 40 deg C. at pH optimum produces from M-acetyl-casein as substrate an amount of primary amino-groups equivalent to 1 micromole of glycine.) Proteolysis was stopped after 30 mins by pH shock with phosphoric acid to pH 2.5.

SDS-PAGE of the proteolysis products showed essentially only two polypeptides formed with apparent mw 14 and 19 kD, together summing to the original mw of the lipase. To analyse the products for identification of the cleavage site, anionic detergent Was removed from the preparation with Extractigel D (Pierce), and the polypeptides separated on a Bakerbond wide pore 4.6×250 mm C4 RP-HPLC column, by elution with an acetonitrile gradient containing 0.1% trifluoroacetic acid. The resulting chromatogram contained three peaks, found to correspond to the 19 kD, 14 kD and 34 kD PAGE bands respectively.

Gas phase sequencing (ABI 470/120) of the separated products revealed the following N-terminal sequences: 1: His-Asn-Thr-Asp-; 2: Ala-Asp-Thr-Tyr-; 3: Ala-Asp-Thr-Tyr-. It was deduced that the lipase had been split by Savinase between Ser153 and His154 in the original aminoacid sequence of the lipase, and that the fragment containing 1–153 was peak 2, mw ~14 kD, containing the original N-terminal and the fragment containing 154–319 was peak 1, mw ~19 kD, containing the original C-terminal.

Corresponding treatment of lipase from *Pseudomonas cepacia* (of sequence published in EP 0 331 376 (Amano)) showed a primary subtilitic cleavage site between Ser152 and Ser153 of the mature lipase.

Mutations in lipase of *Pseudomonas glumae* to confer improved resistance to subtilisin degradation, and constructed by the methods described above, include the following examples: mutant PGL24, carrying mutation H154P, and mutant PGL6, carrying mutation V150D. In both these cases the mutant lipase enzyme has been tested and shown to have significantly reduced susceptibility to proteolytic attack. Correpending useful mutations in lipase of *Pseudomonas cepacia* include for example S153P.

The formulation of detergent compositions according to the invention is further illustrated by way of the following non-limitative Examples D1–D14, in each of which a lipase according to the invention is present at a level of 0.5% by weight except where otherwise provided:

EXAMPLE D1

A detergent powder according to an embodiment of the invention containing phosphate builder is formulated to contain: total active detergent about 16%, anionic detergent about 9%, nonionic detergent about 6%, phosphate-containing builder about 20%, acrylic or equivalent polymer about 3.5%, (alternatively down to about 2%), perborate bleach precursor about 6–18%, alternatively about 15–20%, amino-containing bleach activator about 2%, silicate or other structurant about 3.5%, alternatively up to about 8%, enzyme of about 8 glycine units/mg activity, with alkali to adjust to desired pH in use, and neutral inorganic salt, and enzymes (about 0.5% each protease and lipase).

The anionic detergent is a mixture of sodium dodecylbenzene sulphonate, alternatively sodium linear alkyl-benzene-sulphonate, 6%, and primary alkyl sulphate 3%. The nonionic detergent is an ethoxylate of an approx. C13–C15 primary alcohol with 7 ethoxylate residues per mole. The phosphate builder is sodium tripolyphosphate. The polymer is polyacrylic acid, alternatively acrylic/maleic copolymer. The perborate bleach precursor is sodium tetraborate tetrahydrate or monohydrate. The activator is tetra-acetyl-ethylene-diamine. The structurant is sodium silicate. The neutral inorganic salt is sodium sulphate.

EXAMPLE D1a

A detergent powder according to an embodiment of the invention containing phosphate builder is formulated to contain: total active detergent about 15%, anionic detergent about 7%, nonionic detergent about 6%, phosphate-containing builder about 25%, acrylic or equivalent polymer about 0.5%, perborate bleach precursor about 10%, amino-containing bleach activator about 2%, silicate or other structurant about 6%, protease enzyme of about 8 glycine units/mg grade, with alkali to adjust to desired pH in use, and neutral inorganic salt, and enzymes (about 0.5% each protease and lipase).

The anionic detergent is sodium linear alkyl-benzene-sulphonate. The nonionic detergent is an ethoxylate of an approx. C13–C15 primary alcohol with 7 ethoxylate residues per mole or a mixture of this with the corresponding alcohol ethoxylated to the extent of 3 residues per mole. The phosphate builder is sodium tripolyphosphate. The perborate or peracid bleach precursor is sodium tetraborate tetrahydrate. The activator is tetra-acetyl-ethylene-diamine. The structurant is sodium silicate. The neutral inorganic salt is sodium sulphate.

EXAMPLE D2

A detergent powder according to an embodiment of the invention containing zeolite builder is formulated to contain: total active detergent about 16%, anionic detergent about 9%, nonionic detergent about 6%, zeolite-containing builder about 20%, acrylic or equivalent polymer about 3.5%, perborate bleach precursor about 6–18%, amino-containing bleach activator about 2%, silicate or other structurant about 3.5%, alternatively down to about 2.5%, enzyme of about 8 (alternatively about 15) glycine units/mg grade, with alkali to adjust to desired pH in use, and neutral inorganic salt, and enzymes (about 0.5% each protease and lipase).

The anionic detergent is a mixture of sodium dodecylbenzene sulphonate, alternatively sodium linear alkyl-benzene-sulphonate, 6% and primary alkyl sulphate 3%. The nonionic detergent is an ethoxylate of an approx. C13–C15 primary alcohol with 7 ethoxylate residues per mole. The zeolite builder is type A zeolite. The polymer is polyacrylic acid. The perborate bleach precursor is sodium tetraborate tetrahydrate or monohydrate. The activator is tetraacetyl-ethylenediamine. The structurant is sodium silicate. The neutral inorganic salt is sodium sulphate.

EXAMPLE D2a

A detergent powder according to an embodiment of the invention containing zeolite builder is formulated to contain: total active detergent about 14%, anionic detergent about 7%, nonionic detergent about 7%, zeolite-containing builder about 25%, acrylic or equivalent polymer about 3%, perborate or peracid bleach precursor about 10%, amino-containing bleach ac-tivator about 2%, silicate or other structurant about 0.5%, enzyme of about 6 glycine units/mg grade, with alkali to adjust to desired pH in use, and neutral inorganic salt, and enzymes (about 0.5% each protease and lipase).

The anionic detergent is sodium linear alkyl-benzene-sulphonate, the nonionic detergent is a mixture of ethoxylates of an approx. C13–C15 primary alcohol with 7 and 3 ethoxylate residues respectively per mole. The zeolite builder is type A zeolite. The polymer is an acrylic/maleic copolymer. The perborate bleach precursor is sodium tetraborate monohydrate. The activator is tetra-acetyl-ethylene-diamine. The structurant is sodium silicate. The neutral inorganic salt is sodium sulphate.

EXAMPLE D3

An aqueous detergent liquid according to an embodiment of the invention is formulated to contain: Dodecylbenzene-sulphonic acid 16%, C12–C15 linear alcohol condensed with 7 mol/mol ethylene oxide 7%, monoethanolamine 2%, citric acid 6.5%, sodium xylenesulphonate 6%, sodium hydroxide about 4.1%, protease 0.5%, minors and water to 100%. The pH is adjusted to a value between 9 and 10. Lipase and protease are both present at about 0.5%.

EXAMPLE D4

A nonaqueous detergent liquid according to an embodiment of the invention is formulated using 38.5% C13–C15 linear primary alcohol alkoxylated with 4.9 mol/mol ethylene oxide and 2.7 mol/mol propylene oxide, 5% triacetin, 30% sodium triphosphate, 4% soda ash, 15.5% sodium perborate monohydrate containing a minor proportion of oxoborate, 4% TAED, 0.25% EDTA of which 0.1% as phosphonic acid, Aerosil 0.6%, SCMC 1%, and 0.6% protease. The pH is adjusted to a value between 9 and 10, e.g. about 9.8. Lipase and protease are both present at about 0.5%.

EXAMPLE D5

A detergent powder according to an embodiment of the invention is formulated in the form of a granulate having a bulk density of at least 600 g/l, containing about 20% by weight surfactant of which about 10% is sodium dodecylbenzene sulphonate, and the remainder is a mixture of Synperonic A7 and Synperonic A3 (about 5.5% to 4.5%), and zero neutral inorganic salt .(e.g. sodium sulphate), plus phosphate builder about 33% sodium perborate tetrahydrate about 16%, TAED activator about 4.5%, sodium silicate about 6%, and minors including sodium carbonate about 2%, and moisture content about 10%. Enzymes (about 0.5% each of protease and lipase enzyme) are included.

EXAMPLE D6

A detergent powder according to an embodiment of the invention is formulated in the form of a granulate having a bulk density of at least 600 g/l, alternatively about 550 g/l, containing about 20%, alternatively down to about 16%, by weight surfactant of which about 9%, alternatively about 7%, is sodium dodecylbenzene sulphonate, alternatively sodium linear alkyl benzene sulphonate, and the remainder is a mixture of Synperonic A7 and Synperonic A3 (or similar ethoxylates) (respectively about 5% & 6%, alternatively about 4% and 7%), and zero neutral inorganic salt (e.g. sodium sulphate), plus zeolite builder about 30%, alternatively about 25%, sodium perborate tetrahydrate, alternatively monohydrate, about 14% or 15%, TAED activator about 3.6%., and minors including sodium carbonate about 9%, or up to 15%, Dequest 2047 (™) about 0.7%, and moisture content about 10%. Enzymes (about 0.5% each of protease and lipase, or about 0.2% lipase and about 0.7% protease) are included.

EXAMPLE D6a

A detergent powder according to an embodiment of the invention is formulated in the form of a granulate having a bulk density of at least 600 g/l, containing about 15% by weight surfactant of which about 7% is sodium linear alkyl benzene sulphonate, 2% primary alcohol sulphate, and the remainder Synperonic A7 or similar ethoxylate, and zero neutral inorganic salt (e.g. sodium sulphate), plus zeolite builder about 22%, sodium perborate tetrahydrate about 15%, TAED activator about 7%, and minors including sodium carbonate about 15%, Dequest 2047 (™). about 0.7%, and moisture content about 10%. Enzymes (protease and lipase to about 1.2% in aggregate) are present.

EXAMPLE D7

A detergent powder according to an embodiment of the invention is formulated to contain: Dodecylbenzenesulphonic acid 6%, C12–C15 linear alcohol condensed with 7 mol/mol ethylene oxide 5%, fatty acid soap 3%, Sokolan CP5 polymer (™) 3%, zeolite A 22%, sodium carbonate 10%, sodium 'sulphate 17%, clay particles 8%, sodium perborate tetrahydrate 13%, tetraacetyl-ethylenediamine 2%, protease 0.5%, minors and water to 100%. The pH is adjusted to a value between 9 and 10. Lipase and protease are both present at about 0.5%.

EXAMPLE D8

A detergent (soap) bar according to an embodiment of the invention is formulated as follows: soap based on pan-saponified 82% tallow, 18% coconut oil, neutralised with 0.15% orthophosphoric acid, mixed with protease (about 8 GU/mg of the bar composition) and mixed with sodium formate 2%, borax 2%, propylene glycol 2% and sodium sulphate 1%, is then plodded on a soap production line. Lipase and protease are both present at about 0.5%.

EXAMPLE D9

Structured liquid detergents can contain, in addition to a protease (about 0.5%). and lipase as described herein (about 0.5%), 2–15% nonionic surfactant, 5–40% total surfactant, comprising nonionic and optionally anionic surfactant, 5–35% phosphate-containing or non-phosphate-containing builder, 0.2–0.8% polymeric thickener, e.g. cross-linked acrylic polymer with m.w. over 10^6, at least 10% sodium silicate, e.g. as neutral waterglass, alkali (e.g. potassium-containing alkali) to adjust to desired pH, preferablu in the range 9–10 or upwards, e.g. above pH 11, with a ratio sodium cation: silicate anion (as free silica) (by weight) less than 0.7:1, and viscosity of 0.3–30 Pas (at 20 deg C. and 20 s-1).

Suitable variants of this example contain about 5% non-ionic surfactant C13–15 alcohol alkoxylated with about 5 EO groups per mole and with about 2.7 PO groups per mole, 15–23% neutral waterglass with 3.5 weight ratio between silica and sodium oxide, 13–19% KOH, 8–23% STPP, 0–11% sodium carbonate, 0.5% Carbopol 941 (™).

EXAMPLE D10

A structured, viscous, aqueous liquid detergent suitable for laundry use is formulated as follows (% by weight):

| | |
|---|---|
| Citric acid | 2.5 |
| Borax (10 aq) | 4 |
| NaOH | 2 |
| Glycerol | 5 |
| C14–C15 Linear alkyl-benzene-sulphonate or C14–15 primary alcohol sulphate | 6.5 |
| Synperonic A3 Nonionic C12–C15 3 EO | 1.2 |
| Synperonic A7 Nonionic C12–C15 7 EO | 3.6 |
| Zeolite | 20 |
| Protease | 0.5 |
| Amylase (Termamyl 300LDX) | 0.2 |
| minors and water | to 100% |

The pH can be adjusted to a value between 9 and 10. The enzyme comprises lipase (about 0.5%).

EXAMPLE D11

An isotropic aqueous liquid detergent suitable for laundry use is formulated as follows (% by weight):

| | |
|---|---|
| Citric acid | 2 |
| Boric acid | 1 |
| NaOH | 3 |
| KOH | 4.5 |
| Glycerol | 10 |
| Ethanol | 6.5 |
| Nonionic surfactant (C12-alcohol 6.5 EO ethoxylate groups/mol) or sodium primary alcohol sulphate | 10 |
| Oleic acid | 16 |
| Coconut oil (C12) soap | 11 |
| Protease | 0.5 |
| minors and water | to 100% |

The pH can be adjusted to a value between 9 and 10. The enzyme comprises lipase (about 0.5%).

EXAMPLE D12

An aqueous liquid detergent composition is formulated to contain:

| | |
|---|---|
| sodium alkyl-benzene-sulphonate | 14.5 |
| C18 sodium soap | 2 |
| Nonionic detergent (C12–15 6 EO) | 9 |
| Fatty acid (oleic acid) | 4.5 |
| sodium alkenyl succinate | 11 |
| propanediol | 1.5 |
| ethanol | 3.6 |
| sodium citrate | 3.2 |
| Complexing agent e.g. Dequest 2060 | 0.7 |
| Protease | 0.5 |
| Amylase | 0.1 |
| Sodium chloride | 6.5 |
| minors and water | to 100% |

The pH can be adjusted to a value between 9 and 10. The enzyme comprises lipase (about 0.5%).

EXAMPLE D13

An aqueous liquid detergent composition is formulated to contain:

| | |
|---|---|
| sodium alkyl-benzene-sulphonate | 8 |
| nonionic detergent 6.5 EO | 10 |
| Oleic diethylamide | 10 |
| Fatty acid (C12/C18 75:25) | 18 |
| sodium citrate | 1 |
| triethanolamine | 5 |
| propanol | 7 |
| ethanol | 5 |
| Dequest 2060 | 0.5 |
| Protease | 0.5 |
| Amylase | 0.1 |
| minors and water | to 100% |

The pH can be adjusted to a value between 9 and 10. The enzyme comprises lipase (about 0.5%).

EXAMPLE D14

A non-aqueous liquid detergent composition is formulated to contain (% by weight):

| | |
|---|---|
| Liquid nonionic detergent (C10–12, 6.2 EO) | 41% |
| triacetin | 5 |
| linear alkylbenzenesulphonic acid | 6 |
| magnesium oxide stabiliser | 1 |
| Sodium carbonate builder/base | 18 |
| Calcium carbonate builder | 8 |
| bleach activator TAED | 3.5 |
| bleach precursor perborate monohydrate | 10.5 |
| partly-hydrophobic silica | 2 |
| protease | 0.4 |
| lipase (Lipolase) | 0.3 |
| minors or additional | to 100% |
| liquid nonionic surfactant (no water) | |

In formulating this composition, the liquid nonionic surfactant and triacetin are added first, followed by the magnesium oxide, then the other ingredients except enzyme. The mixture is milled in a colloid mill and cooled, and finally the enzyme(s) and any other heat-sensitive minors are added. Protease (about 0.5%) and lipase (about 0.5%) are added at this stage.

Also usable are any of the detergent formulations described and exemplified in EP 0 342 177, with addition of lipase (about 0.5%).

The invention described herein is susceptible of numerous modifications and variations which will be accessible to the skilled reader in the light of the present description, drawings and claims given below, and the documets referred to herein, and the present disclosure extends to all such modifications and to every combination and subcombination of the features mentioned described and illustrated in the description, the documents referred to, the claims and the drawings.

We claim:

1. A substantially pure Pseudomonas lipase mutein produced from a microorganism by recombinant DNA technique, and maintaining an amino acid substitution at a position within its amino acid sequence homologous to position 150 in the corresponding sequence of the mature, secreted lipase of *Pseudomonas glumae*, wherein said mutation confers improved stability against attack by a subtilisin protease.

2. A Pseudomonas lipase mutein as claimed in claim 1, which shows immunological cross-reactivity with an antiserum raised against lipase from *Chromobacter viscosum* var *lipolyticum* NRRLB-3673, or against lipase from Alcaligenes PL-679, ATCC 31371 or FERM-P 3783, or against lipase from *Pseudomonas fluorescens* IAM 1057.

3. A Pseudomonas lipase mutein as claimed in claim 1, in which the aminoacid sequences have been modified by recombinant DNA technique in such a way that loop structures of the lipase are stabilized against physical or chemical denaturation or enzymic cleavage.

4. A Pseudomonas lipase mutein as claimed in claim 1, with aminoacid sequence modification(s) chosen to improve stability of lipase against attack by subtilisin protease, by (i) modifying the sequence at a subtilisin cleavage site in the sequence within five residues on either side of a bond susceptible in the parent enzyme to subtilisin cleavage by deletion of one to three aminoacid residues forming part of such a site as it existed before mutation, or (ii) by introducing by insertion or substitution at least one basic aminoacid residue, or at least one proline residue, at such a cleavage site, or (iii) modifying the electrostatic potential at such a site by introduction of positively charged aminoacids or removal of negatively charged aminoacids at such a site.

5. A Pseudomonas lipase mutein as claimed in claim 4, wherein (i) the aminoacid residue that would become a new N-terminal upon cleavage of the bond susceptible in the parent enzyme to subtilisin cleavage, is replaced by proline; and/or (ii) an aminoacid residue two or four positions from the susceptible bond is replaced by a charged or more polar aminoacid residue.

6. A substantially pure lipase mutein as claimed in any of claims 1 to 5, with aminoacid sequence modification(s) chosen to increase the net positive charge of the lipase and its pI.

7. A Pseudomonas lipase according to claim 2, and in which part of the nucleotide sequence has been replaced by a substantially corresponding part of a nucleotide sequence encoding another lipase, immunologically related to the first.

8. A substantially pure Pseudomonas lipase mutein as claimed in any of claims 1, 2, 3, 4, 5, 6 or 7, with one or more of the following aminoacid sequence modification(s) relative to the sequence of *Ps. glumae* lipase or a homologue thereof:

V150A; V150S; V150D; V150K; V150P+H154P; V150P+S152P+H154P.

9. A substantially pure Pseudomonas lipase mutein according to claim 1, having an amino acid sequence substantially as shown in FIG. 2 or a functional equivalent thereof, and derived from an artificially modified microorganism containing a modified gene substantially corresponding to a prepro-lipase sequence also as shown in FIG. 2 or a functional equivalent thereof.

10. A detergent composition comprising a Pseudomonas lipase mutein or protein according to claim 1, and optionally a subtilisin protease enzyme, wherein the remainder of the detergent composition is either:

(a) formulated as a detergent powder containing phosphate builder, anionic surfactant, nonionic surfactant, acrylic or equivalent polymer, perborate or peracid bleach precursor, amino-containing bleach activator, silicate or other structurant, alkali to adjust to desired pH in use, and neutral inorganic salt; or (b) formulated as a detergent powder containing zeolite builder, anionic surfactant, nonionic surfactant, acrylic or equivalent polymer, perborate or peracid bleach precursor, amino-containing bleach activator, silicate or other structurant, alkali to adjust to desired pH in use, and neutral inorganic salt; or (c) formulated as an aqueous detergent liquid comprising anionic surfactant, nonionic surfactant, humectant, organic acid or other builder, caustic alkali, with a pH adjusted to a value between 9 and 10; or (d) formulated as a nonaqueous detergent liquid comprising a liquid nonionic surfactant consisting essentially of linear alkoxylated primary alcohol, triacetin, sodium triphosphate, caustic alkali, perborate monohydrate bleach precursor, and tertiary amino bleach activator, with a pH adjusted to a value between about 9 and 10; or (e) formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, phosphate builder, perborate or peracid bleach precursor, tertiary amine bleach activator, sodium silicate, and minors and moisture; or (f) formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, zeolite builder, perborate or peracid bleach precursor, tertiary amino bleach activator, sodium silicate, and minors and moisture; or (g) formulated as a detergent powder containing anionic surfactant, nonionic surfactant, acrylic polymer, fatty acid soap, sodium carbonate, sodium sulphate, clay particles, perborate or peracid bleach precursor, tertiary amine bleach activator, sodium silicate, and minors and moisture; or (h) formulated as a soap or synthetic detergent bar containing either soap based on pan-saponified mixture of tallow and coconut oil, neutralized with orthophosphoric acid, or C6–C16 alkylbenzenesulphonate, sodium tripolyphosphate, calcium and sodium carbonate and carboxymethylcellulose, mixed with protease, also mixed with sodium formate, borax, propylene glycol and sodium sulphate, and then plodded on a soap production line.

11. A detergent composition, as claimed in claim 10, wherein the detergent composition is formulated to give a wash liquor pH of 9 or less when used at a rate corresponding to 0.14–0.8 g/l surfactant.

12. A detergent composition, as claimed in claim 10, wherein the detergent composition is formulated to give a wash liquor ionic strength of 0.03 or less, e.g., 0.02 or less, e.g. 0.01 or less, when used at a rate corresponding to 0.4–0.8 g/l surfactant.

13. A detergent composition, as claimed in claim 10, wherein the detergent composition is formulated to give a wash liquor pH of 8.5 or more when used at a rate corresponding to 0.4–0.8 g/l surfactant.

14. A detergent composition, as claimed in claim 10, wherein the detergent composition is formulated to give a wash liquor ionic strength of 0.01 or more, e.g., 0.02 or more, when used at a rate corresponding to 0.04–0.8 g/l surfactant.

\* \* \* \* \*